United States Patent [19]
Guengerich et al.

[11] Patent Number: 5,886,157
[45] Date of Patent: Mar. 23, 1999

[54] EXPRESSION AND PURIFICATION OF HUMAN CYTOCHROME P450

[75] Inventors: F. Peter Guengerich; Zuyu Guo; Punam Sandhu, all of Nashville, Tenn.; Elizabeth M. J. Gillam, Queensland, Australia

[73] Assignee: Vanderbilt University, Nashville, Tenn.

[21] Appl. No.: 194,981

[22] Filed: Feb. 10, 1994

[51] Int. Cl.$^6$ ............................. C07K 1/14; C07K 1/16; C07K 1/36; C12N 9/02

[52] U.S. Cl. .................... 530/412; 530/417; 530/422; 530/425; 435/189

[58] Field of Search ................. 435/184, 69.1, 435/252.3, 252.33, 320.1; 530/417, 412, 422, 425; 536/23.2

[56] References Cited

U.S. PATENT DOCUMENTS

5,240,831  8/1993  Barnes ........................... 435/69.1

FOREIGN PATENT DOCUMENTS

WO 91/13156  9/1991  WIPO.

OTHER PUBLICATIONS

Umeno, M., et al., Biochemistry, vol. 27, "Human ethanol-inducible P450 IIEI: Complete gene sequence, promoter characterization, chromosome mapping and cDNA–directed expression", pp. 9006–9013, 1988.

Richardson, T. H., et al., Archives of Biochemistry and Biophysics, vol. 300, "Purification and characterization of recombinantly–expressed cytochrome P450 2C3 from *Escherichia coli*: 2C3 encodes the 6beta–hydroxylase deficient form of P5403b", pp. 510–, 1993.

Gillam, E. M. J., et al., Archives of Biochemistry and Biophysics, vol. 305, "Expression of modified human cytochrome P450 3A4 in *Escherichia coli* and purification and reconstitution of the enzyme", pp. 123–131, 1993.

Imai, T., et al., The Journal of Biological Chemistry, vol. 268, "Expression and purification of functional human 17 alpha–hydroxylase/17,20–lyase (P450c17) in *Escherichia coli*", pp. 19681–19689, 1993.

(List continued on next page.)

*Primary Examiner*—Charles L. Patterson, Jr.
*Assistant Examiner*—William W. Moore
*Attorney, Agent, or Firm*—Needle & Rosenberg PC

[57] ABSTRACT

The invention provides a nucleic acid encoding a human cytochrome P450 2E1 comprising a 5' terminal deletion of 63 nucleotides, thereby encoding methionine at the first codon position of the 5' terminus, the codon ATG in the second codon position of the 5' terminus, and silent adenine and thymine nucleotide substitutions in the 5' region. The invention also provides a nucleic acid encoding a human cytochrome P450 2C10 comprising a 5' terminal deletion of nucleotides 7 through 60, thereby encoding methionine at the first codon position and alanine at the second position of the 5' terminus, and silent adenine and thymine nucleotide substitutions in the 5' region. The present invention also provides a method of purifying a recombinant cytochrome P450 protein from a host cell culture comprising the steps of: a. fractionating the host cells to prepare their membranes; b. adding a non-ionic detergent in a concentration of between 0.8% to 2% (w/v) and in a detergent to protein ratio of between 4:1 to 10:1 to the membranes; c. adding an ionic detergent in a concentration of between 0.4% to 0.8% (w/v) and in a detergent to protein ratio of between 2:1 to 4:1 to the membranes; d. centrifuging the membrane detergent mixture to remove insoluble materials; and, e. purifying the protein in the following order: i) through a diethylaminoethyl-beaded column; ii) through a carboxymethyl-beaded column; and iii) through a hydroxylapatite column. The invention also provides a purified recombinant human cytochrome P450 1A1 which has retained its catalytic activity, such as catalyzing 7-ethoxyresorufin O-deethylation and benzo(a)pyrene 3-hydroxylation.

9 Claims, 42 Drawing Sheets

OTHER PUBLICATIONS

Sandhu, P., et al., Archives of Biochemistry and Biophysics, vol. 306, "Expression of modified cytochrome P450 2C10 (2C9) in *Escherichia coli*, purification, and reconstitution of catalytic activity", pp. 443–450, 1993.

Larson et al., "Alcohol–inducible Cytochrome P–450IIE1 Lacking the Hydrophobic $NW_2$–terminal Segment Retains Catalytic Activity and is Membrane–bound When Expressed in *Escherichia coli*", *J. Biol. Chem.*, 266:7321–7324 (1991).

Larson et al., "Purification and properties of a shortened form of cytochrome P–450 2E1: Deletion of the $NH_2$–terminal membrane–insertion signal peptide does not alter the catalytic activities", *Proc. Natl. Acad. Sci. USA*, 88:9141–9145 (1991).

Pernecky et al., "Expression of truncated forms of liver microsomal P450 cytochromes 2B4 and 2E1 in *Escherichia coli*: Influence of $NH_2$–terminal region on localizaion in cytosol and membranes", *Proc. Natl. Sci. USA*, 90:2651–2655 (1993).

Li et al., The Expression of a Catalytically Active Cholesterol 7α–Hydroxylase Cytochrome P450 in *Escherichia coli*, *J. Biol. Chem.*, 266:19186–19191 (1991).

Sami et al., "Effect of changes in 5' coding sequence on level of expression of ovine growth hormone cDNA in *Escherichia coli*", *Biochem. Soc. Trans.*, 18:567–568 (1990).

Barnes et al., "Expression and enzymatic activity of recombinant cytochrome P450 17α–hydroxylase in *Escherichia coli*", *Proc. Natl. Acad. Sci. USA*, 88:5597–5601 (1991).

Wada et al., "Expression of Functional Bovine Cholesterol Side Chain Cleavage Cytochrome P450 (P450scc) in *Escherichia coli*", *Arch. Biochem. Biophy.*, 290:376–380 (1991) provide a bacterial expression system.

Fisher et al., "High–level expression of functional human cytochrome P450 1A2 in *Escherichia coli*", *FASEB J.*, 6:759–764 (1992).

|              |       | 1            5            10           15           20           25           30           35 |
|---|---|---|
| SEQ ID NO:7  | NF1:  | M A L I P D L A M E T W L L L A V S L V L L Y L Y G T H S H G L F K K K |
| SEQ ID NO:8  | NF10: | M A — — — — — — — — — — — — — — — — — — — — — — — Y G T H S H G L F K K K |
| SEQ ID NO:9  | NF12: | M A — — — — — — — — — — — — L L L A V — — — — — — — — — — — — — — F K K K |
| SEQ ID NO:10 | NF13: | M A L I P D L A M E T W L L L A V S L V L L Y L Y G T H S H G L F K K K |
| SEQ ID NO:11 | NF14: | M A — — — — — — — — — — — — L L L A V F L V L L Y L Y G T H S H G L F K K K |

FIG.1

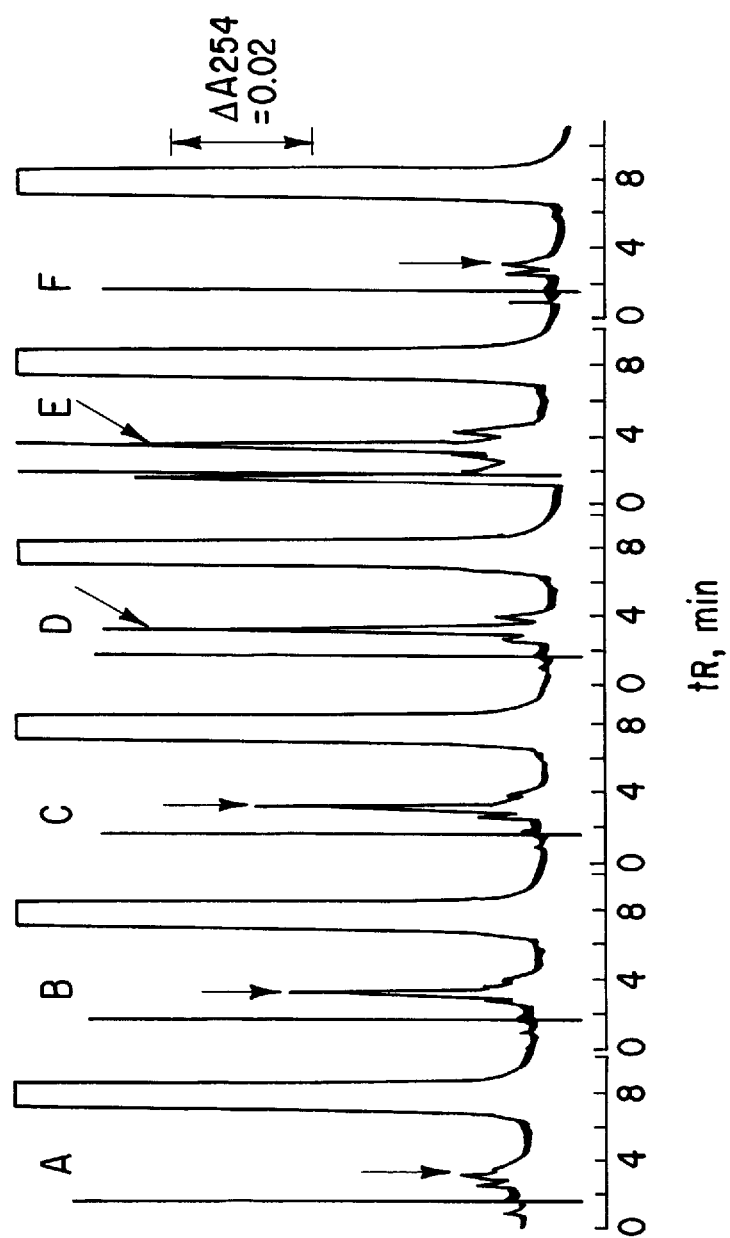

Amino acid sequences

```
                       1       5        10       15       20       25       30       35    40
SEQ ID NO:14 (native) 1027   MDSLVVLVLCLSCLLLLSLWRQSSGRGKLPPGPTPLPVIG...
SEQ ID NO:15           987   MALLAVFLCLSCLLLLSLWRQSSGRGKLPPGPTPLPVIG...
SEQ ID NO:16           988   MA
SEQ ID NO:17          1028   M ALLAVFVLCLSCLLLLSLWRQSSGRGKLPPGPTPLPVIG...
SEQ ID NO:18          1029   MA                   LLAVFLPVIG...
                                                 RQSSGRGKLPPGPTPLPVIG...
```

Nucleotide/amino acid sequences

```
SEQ ID NO:19 (native) 1027   ATG GAT AGC CTA GTG GTC CTT GTG
                              M   D   S   L   V   V   L   V SEQ ID NO:20          1028   ATG GCT CTG TTA TTA GCA GTT TTT
                              M   A   L   L   L   A   V   F SEQ ID NO:21          1029   ATG GCT CGA CAA TCT TCT GGA CGA
                              M   A   R   Q   S   S   G   R
```

FIG.10

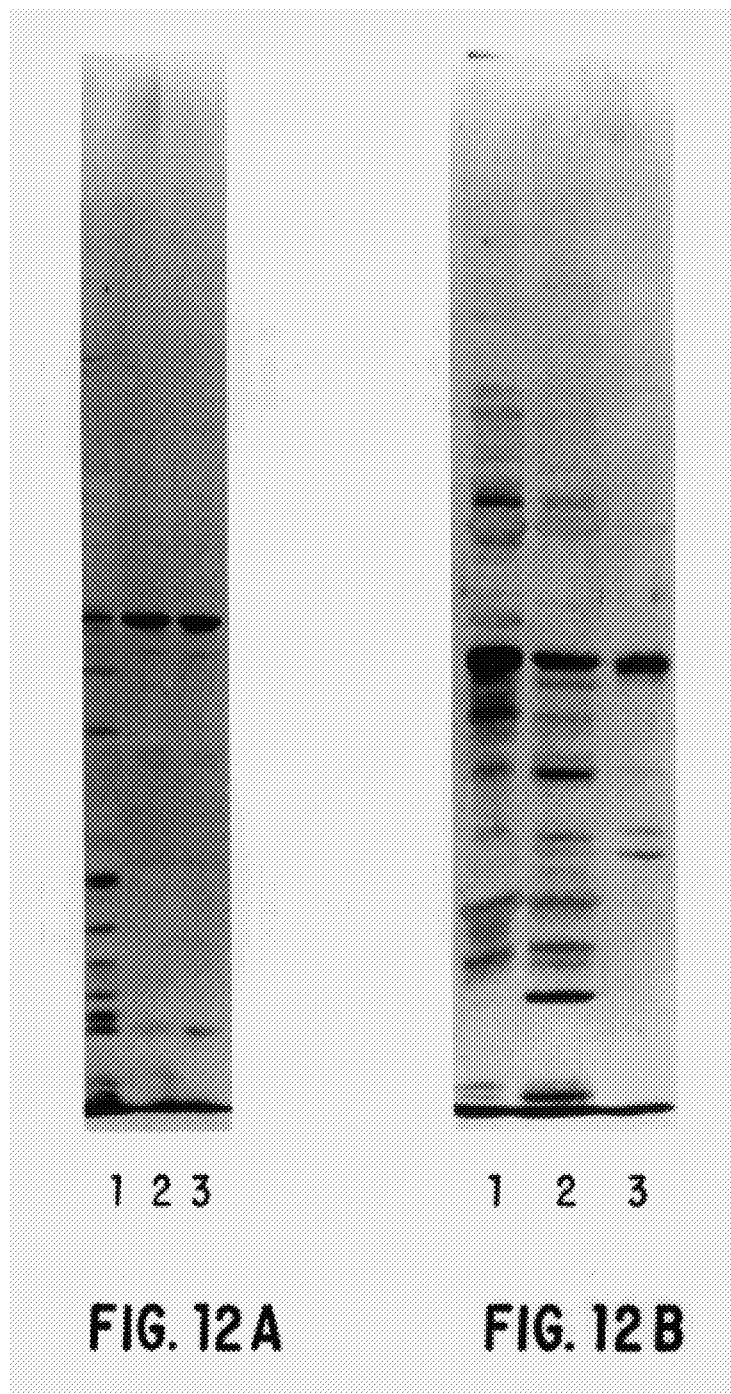

2C1028

2C1029

```
                        1                10                  20                  30            40
SEQ ID NO:25    1023 (native)   MALSQSVPFSATELLLASAIFCLVFWVLKGLRPRVPKGLK...
SEQ ID NO:26     963            MALLLAVFFSATELLLASAIFCLVFWVLKGLRPRVPKGLK...
SEQ ID NO:27     964            MA                LLLAVFKGLRPRVPKGLK...
SEQ ID NO:28    1024            MA          LLLAVFLFCLVFWVLKGLRPRVPKGLK...
SEQ ID NO:29    1025            MA                       KGLRPRVPKGLK...
```

FIG.14A

```
                        1    2   14  15  16  17  18  19  20
SEQ ID NO:30  1024 (original)  ATG GCA CTT CTC CTG GCC TCT GCC ATC
                                M   A   L   L   L   A   S   A   I
SEQ ID NO:31  1024 (modified)  ATG GCT CTG CTG TTA TTA GCA GTT TTT CTG
                                M   A   L   L   L   L   A   V   F   L 1    2   29  30  31  32  33  34
SEQ ID NO:32  1025 (original)  ATG GCT AAG GGT TTG AGG CCT CGG
                                M   A   K   G   L   R   P   R
SEQ ID NO:33  1025 (modified)  ATG GCT AAA GGA TTA CGA CCA CGA
                                M   A   K   G   L   R   P   R
```

FIG.14B

N-TERMINAL AMINO ACID SEQUENCES

```
                          1       5        10       15       20      25
SEQ ID NO:39   2E1 #1     MSALGVTVALLVWAAFLLLVSMMRQVHSS
SEQ ID NO:40   2E1 #11                                  MMRQVHSS
SEQ ID NO:41   2E1 #14    M AL      LL   AVFLLLVSMMRQVHSS
SEQ ID NO:42   2E1 #15    MSALGVTVALLVWAAFLLLVSMMRQVHSS
SEQ ID NO:43   2E1 #16                                  MMRQVHSS
SEQ IS NO:44   2E1 #17    MAALGVTVALLVWAAFLLLVSMMRQVHSS
SEQ ID NO:45   2E1 #18                                  MARQVHSS
```

5' PCR primers used for amplification of various constructs

```
SEQ ID NO:46   2E1 #1    5' cc agc ggc cat atg tct gcc ctc gga 3'
SEQ ID NO:47   2E1 #11      ctg ctg gtg cat atg tgg agg ca
SEQ ID NO:48   2E1 #14      gga ggt cat atg gct ctg tta gca gtt ttt ctg ctg gtg tcc atg tgg cgc cag gtg
SEQ ID NO:49   2E1 #15      tta gga ggt cat atg tct gct gga ta act gtt gct ctg
SEQ ID NO:50   2E1 #16      tta gga ggt cat atg tgg cgt caa gtt cat tct tct tgg aat ctg ccc
SEQ ID NO:51   2E1 #17      tta gga ggt cat atg gct gct gta act gtt gct ctg
SEQ ID NO:52   2E1 #18      tta gga ggt cat atg gct cgt caa gtt cat tct tct tgg aat ctg ccc
```

```
BclI/BamHI linker for construct #1
SEQ ID NO:53  5' GGC TGC ATC CAT CGA TGC TTA GGA GGT 3'
SEQ ID NO:54  3' CCG ACC TAG GTA GCT ACG AAT CCT CCA CTA G 5'

BamHI/NdeI linker for modification of pCW:
SEQ ID NO:55  5' TAG GAT CCT GCC TGC CA 3'
SEQ ID NO:56  3'   C CTA GGA CGG ACG GTA T 5'

NdeI/NcoI linker for construct #11:
SEQ ID NO:57  5' T ATG GCT TCA AGA CCT CAG GTC CAG CCC AAA GGC CTG AAG AAT CCA CCA GGG C 3'
SEQ ID NO:58  3'   AC CGA AGT TCT GGA GTC CAG GGG TTT CCG GAC TTC TTA GGT CCC GGT AC 5'

3' PCR primer for constructs #14-17:
SEQ ID NO:59  5' GCC AGC CCC ATG GCC CTG GTG GAT 3'

5' PCR primer for constructs #14-17:
SEQ ID NO:60  #14  5' TTA GGA GGT CAT ATG GCT CTG TTA TTA GCA GTT TTT TGT CTG GTA TTC 3'
SEQ ID NO:61  #15  5' TTA GGA GGT CAT ATG CAT ATG TTG TTT CCA ATT TCA ATG TCA GCA ACG 3'
SEQ ID NO:62  #16  5' TTA GGA GGT CAT ATG GCT TCA CGT CCACAA GTA CCA AAA GGC 3'
SEQ ID NO:63  #17  5' TTA GGA GGT CAT ATG GCT TTT CCA ATT TCA ATG TCA GCA ACG 3'
```

| | | |
|---|---|---|
| SEQ ID NO:64 | #1: | MLFPISMSATEFLLASVIFCLVFWVMRASRPQV |
| SEQ ID NO:65 | #11: | M ASRPQV |
| SEQ ID NO:66 | #14: | MA LLLA V FCLVFWVMRASRPQV |
| SEQ ID NO:67 | #15: | MLFPISMSATEFLLASVIFCLVFWVMRASRPQV |
| SEQ ID NO:65 | #16: | M ASRPQV |
| SEQ ID NO:68 | #17: | MAFPISMSATEFLLASVIFCLVFWVMRASRPQV |

FIG.38

EXPRESSION AND PURIFICATION OF HUMAN CYTOCHROME P450

This invention was made with government support under grant nos. CA44353, ES00267 and GM36590 awarded by the National Institutes of Health. The government has certain rights in the invention.

BACKGROUND OF THE INVENTION

The cytochrome P450 proteins are the major enzymes catalyzing the oxidation of drugs in the body, as well as steroids, carcinogens, pesticides, and numerous other compounds. Since there are at least 30 different cytochrome P450 enzymes, it is of considerable interest in the pharmaceutical and other fields to identify which of these enzymes are most important in the metabolism of individual compounds. There are now numerous examples of adverse drug-drug interactions and side effects that can now be understood in terms of the cytochrome P450 enzymes.

In many cases there are considerable differences between these enzyme systems in experimental animal models and humans, and there has been an increasing emphasis on the use of human enzymes in drug development, toxicity testing, and related fields. However, the isolation of enzymes from human tissues has been a problem because of the limited supply of tissue (esp. liver) and the difficulty involved in separation. With the availability of cDNA clones for several of these cytochrome P450s, it has become possible to express the proteins in artificial vector systems. Work with mammalian cell systems has been fairly extensive in recent years. However, these systems are expensive and the concentrations of the enzymes produced are very low. Alternative strategies involve expression in yeast and in baculovirus (insect cells). These systems are capable of producing higher concentrations of cytochrome P450 proteins but have some inherent problems. Yeast cells are very difficult to break. Baculovirus systems are sensitive to heme concentrations and also expensive to use. A presentation of articles on various systems is set forth in *Methods in Enzymology*, Vol. 206, Academic Press (1991).

In many respects, expression of cytochrome P450 proteins in bacteria is the most useful system because of the potentially high yields and low cost. However, the membraneous nature of the cytochrome P450 enzymes and other factors have been problematic in the use of most of the typically available vector systems. However, some progress has been made since 1990.

Larson et al. (*J. Biol. Chem.* 266, 7321–7324, 1991) found that rabbit cytochrome P450 2E1 could be expressed in *Escherichia coli* using the commercially available vector pKK233-2. In the course of these and subsequent investigations, they found that the protein was still catalytically active even if a 26–45 amino acid segment was removed. They pursued this strategy with the hope of producing a protein that would be soluble because of the deletion of the hydrophobic tail (see also Pernecky et al. *Proc. Natl. Acad. Sci.* 90, 2651–2655, 1993). Li and Chiang (*J. Biol. Chem.* 266, 19186–19191, 1991) also reported that rat cytochrome P450 7A could be produced in *E. coli* using a pKK vector. They changed the second codon to alanine and also found that deletion of 23 residues of the N-terminus raised the level of production. Another key study was that Barnes et al. (*Proc. Natl. Acad Sci. USA* 88, 5597–5601, 1991), who did not delete residues but changed the N-terminus of bovine cytochrome P450 17A to MALLLAVFL . . . (SEQ. ID. NO.: 6) and found considerable expression, using the vector called pCW (tac/tac promoter). This same sequence was inserted at the end of human cytochrome P450 1A2 to achieve high expression levels (in the pCW vector) (Fisher et al., *FASEB J.* 6, 759–764, 1992). Some purification of cytochrome P450s expressed in bacteria had been done (see the Larson et al. and Li and Chiang references), although numerous column steps were employed and the practicality is difficult to establish.

The inventions concerning various human cytochrome P450s provided herein are based in part on five factors: (1) some modification of the 5' terminus has been necessary in every case, (2) the presence of an alanine in the second position (GCT codon) is useful but not always sufficient, (3) the MALLLAVFL (SEQ. ID. NO.: 6) sequences (Barnes et al.) works well in some cases but not others, (4) commercially available vectors, including pKK, are not very useful, and (5) there is not a universal conclusion involving the effect of deletion of a large segment of the 5'-terminus on protein expression.

The present invention greatly improves on the state of the art by providing improved vectors for expression of various cytochrome P450 proteins. Also provided are improved strategies for the facile purification of recombinant human cytochrome P450 proteins utilizing novel combinations of detergents and enzyme inhibitors, as well as a novel purified recombinant P450 1A1, which is catalytically active.

SUMMARY OF THE INVENTION

The invention provides a nucleic acid encoding a human cytochrome P450 2E1 comprising a 5' terminal deletion of 63 nucleotides, thereby encoding methionine at the first codon position of the 5' terminus, the codon ATG in the second codon position of the 5' terminus, and silent adenine and thymine nucleotide substitutions in the 5' region. The invention also provides a nucleic acid encoding a human cytochrome P450 2C10 comprising a 5' terminal deletion of nucleotides 7 through 60, thereby encoding methionine at the first codon position and alanine at the second position of the 5' terminus, and silent adenine and thymine nucleotide substitutions in the 5' region.

The present invention also provides a method of purifying a recombinant cytochrome P450 protein from a host cell culture comprising the steps of: a. fractionating the host cells to prepare their membranes; b. adding a non-ionic detergent in a concentration of between 0.8% to 2% (w/v) and in a detergent to protein ratio of between 4:1 to 10:1 to the membranes; c. adding an ionic detergent in a concentration of between 0.4% to 0.8% (w/v) and in a detergent to protein ratio of between 2:1 to 4:1 to the membranes; d. centrifuging the membrane detergent mixture to remove insoluble materials; and, e. purifying the protein in the following order: i) through a diethylaminoethyl-beaded column; ii) through a carboxymethyl-beaded column; and iii) through a hydroxylapatite column.

The invention also provides a purified recombinant human cytochrome P450 1A1 which has retained its catalytic activity, such as catalyzing 7-ethoxyresorufin O-deethylation and benzo(a)pyrene 3-hydroxylation.

BRIEF DESCRIPTION OF THE FIGURES

FIG. 1. P450 3A4-derived amino terminal sequences used in this work. The native sequence is that of NF1 except that in liver the terminal Met is cleaved, as shown earlier (Bork et al, 1989) and again in this work.

FIG. 8. Effect of GSH concentration in the reconstitution system (preincubation) on testosterone 6B-hydroxylation by P450 3A4/NF14. The HPLC traces are shown with the following GSH concentrations in the preincubation: A, 0; B, 1.0 mM; C, 2.0 mM; D, 3.0 mM; E, 3.5 mM; F, 4.0 mM. The 6b-hydroxytestosterone peak is indicated with an arrow in each case.

FIG. 10. Amino acid and nucleotide sequences used in constructs and relevant to this work.

FIG. 12. $NaDodSO_4$-polyacrylamide gel electrophoresis of P450 2C10 fractions expressed in *E. coli*. (A) P450 2C1029: lane 1, solubilized membrane fraction (1.5 μg protein, 0.1 pmol P450); lane 2, DEAE-Sephacel eluate (0.9 μg protein, 1.8 pmol P450); lane 3, hydroxylapatite fraction (0.2 μg, 2.2 pmol P450). (B) P450 2C1028: lane 1, solubilized membrane fraction (16 μg protein, 0.5 pmol P450); lane 2, DEAE-Sephacel void fraction (10 μg protein, 2 pmol P450); lane 3, DEAE-Sephacel gradient eluate fraction (1.4 μg protein, 2 pmol P450).

FIG. 14. N-Terminal amino acid sequences of constructs used in this work. (A) Amino acid sequences of the various constructs. (B) Constructs 1024 and 1025, with nucleotide and amino acid sequences shown.

FIG. 24. N-Terminal amino acid and 5' PCR primer nucleotide sequences of constructs used in this work.

FIG. 37. Oligonucleotide sequences used in construction of N-terminal variants of P450 1A1 for expression in pCW.

FIG. 38. N-Terminal amino acid sequences of constructs used in this work.

DETAILED DESCRIPTION OF THE INVENTION

Figure 2:
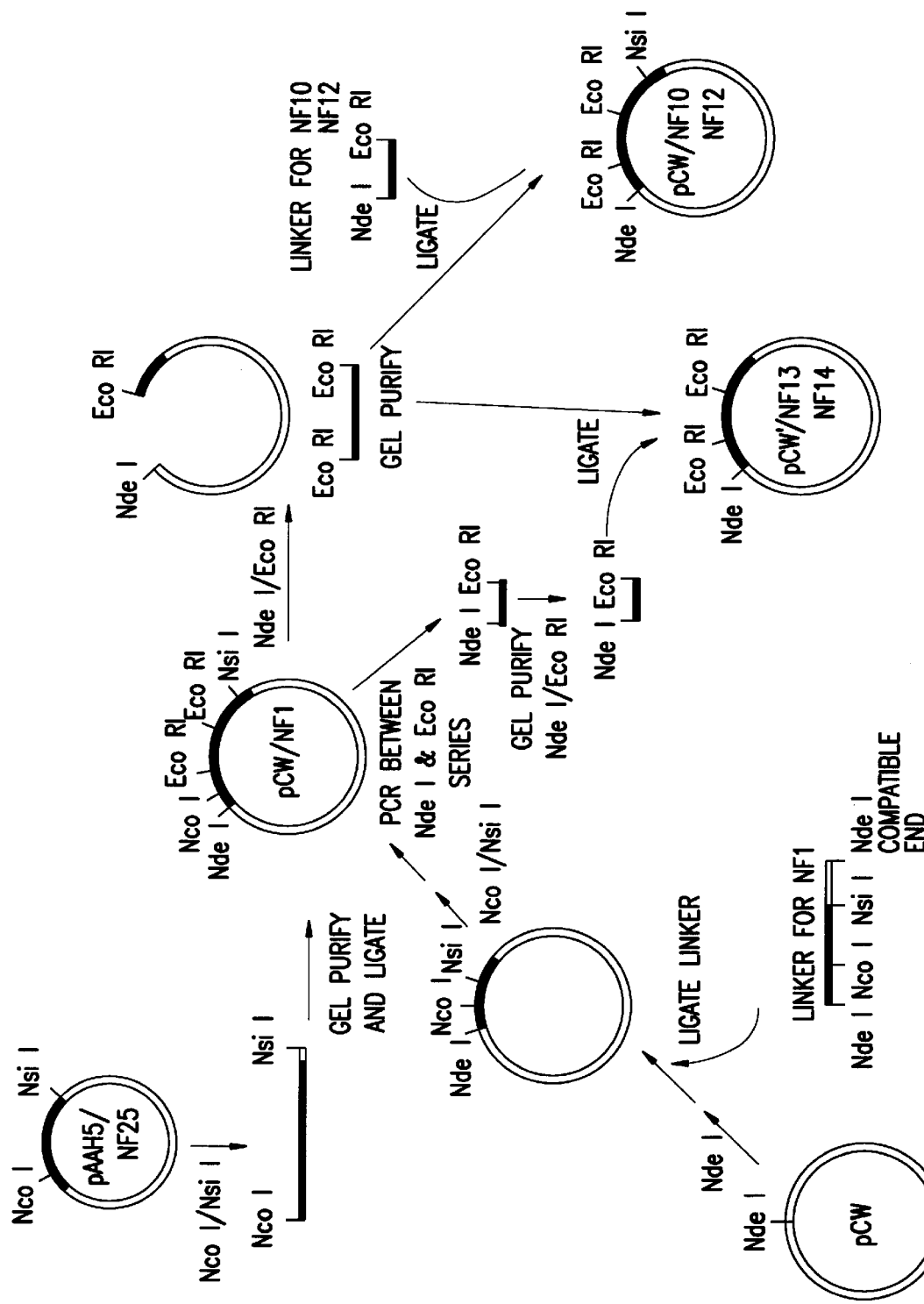
FIG. 2. Scheme depicting construction of P450 3A4 plasmids used in this work.

The invention provides a nucleic acid encoding a human cytochrome P450 2E1 comprising a 5' terminal deletion of 63 nucleotides, thereby encoding methionine at the first codon position of the 5' terminus. The nucleic acid may further comprise the codon ATG in the second codon position of the 5' terminus. The nucleic acid further comprises a silent adenine and thymine nucleotide substitution in the 5' region. "A" as used in the claims can mean one or more. The silent AT substitutions are incorporated in order to minimize the possibility of secondary structure formations without changing the encoding amino acid. Various silent adenine and thymine nucleotide substitutions in the 5' region are set forth in SEQ ID NO: 2. SEQ ID NO: 2 shows the nucleotide sequence for P450 2E1 as expressed in the efficient construct of the present invention, as compared with SEQ ID NO: 1, which shows the naturally occurring form of human cytochrome P450 2E1. The various substitutions, additions and deletions can be determined by comparing SEQ ID NOS: 1 and 2.

The invention also provides a nucleic acid encoding a human cytochrome P450 2C10 comprising a 5' terminal deletion of nucleotides 7 through 60, thereby encoding methionine at the first codon position and alanine at the second position of the 5' terminus. The nucleic acid may further comprise a silent adenine and thymine nucleotide substitution in the 5' region. Various silent adenine and thymine nucleotide substitutions in the 5' region are set forth in SEQ ID NO:4. SEQ ID NO: 4 shows the nucleotide sequence for P450 2C10 as expressed in the efficient construct of the present invention, as compared with SEQ ID NO: 3, which shows the naturally occurring form of human cytochrome P450 2C10. The various substitutions, additions and deletions can be determined by comparing SEQ ID NOS:3 and 4.

One can construct the claimed sequences by various routine methods (Sambrook et al., Molecular Cloning, Latest Edition). An example of a nucleic acid encoding a particular nucleotide sequence is set forth herein. It should be recognized that the novel aspects of the present sequences occur in the amino terminal end. Therefore, one could make changes in the nucleic acid and it would remain a nucleic acid encoding a human cytochrome P450 protein so long as the enzymatic activity of the protein was maintained.

The nucleic acid constructs for cytochrome P450 may also be transfected into a vector, for example pCW, for expression of the nucleic acid. The vector may also be placed in a host suitable for expression of the nucleic acid, such as *E. coli*. Additional routine cloning techniques can be utilized (Sambrook et al.).

The present invention also provides a method of purifying a recombinant cytochrome P450 protein from a host cell culture comprising the steps of: a. fractionating the host cells to prepare their membranes; b. adding a non-ionic detergent in a concentration of between 0.8% to 2% (w/v) and in a detergent to protein ratio of between 4:1 to 10:1 to the membranes; c. adding an ionic detergent in a concentration of between 0.4% to 0.8% (w/v) and in a detergent to protein ratio of between 2:1 to 4:1 to the membranes; d. centrifuging the membrane detergent mixture to remove insoluble materials; and, e. purifying the protein in the following order: i) through a diethylaminoethyl-beaded column; ii) through a carboxymethyl-beaded column; and iii) through a hydroxylapatite column.

The non-ionic detergent is preferably in a concentration of about 1.25% (w/v) and in a detergent to protein ratio of about 6:1. The non-ionic detergent may be selected, for example, from the group consisting of TRITON N-101, EMULGEN-911, EMULGEN-913, TERGITOL-NP10, and LUBROL-PX. The ionic detergent is preferably in a concentration of about 0.6% (w/v) and in a detergent to protein ratio of about 3:1. The ionic detergent may be, for example, sodium cholate.

The above method of purifying a recombinant cytochrome P450 protein from a host cell culture involving all three purification columns has been shown to be particularly effective wherein the protein is a cytochrome P450 2C10, 2E1 or 1A1. When the recombinant protein is cytochrome P450 3A4 it is preferable to omit the second step of the column purification, i.e. the carboxymethyl-beaded column. When the recombinant protein is cytochrome P450 1A2 it is preferable to omit the third step of the column purification, i.e. the hydroxylapatite column.

When the protein is a P450 1A2 or 1A1, the invention provides that a strong inhibitory ligand, e.g. α-naphthoflavone (7,8-benzoflavone), may be added to the membranes before adding the detergents to the fractionated cells. This helps to stabilize the cells and to maintain catalytic activity. Other suitable inhibitory ligands can be determined by comparison to α-naphthoflavone and screened for stabilization activity by the methods set forth in the Examples. Thus, analogs of α-naphthoflavone are included in the invention. When the protein is a human cytochrome P450 3A4, it is helpful to add the final step of preincubating the purified protein with glutathione, in order to help stabilize catalytic activity.

The invention also provides a purified recombinant human cytochrome P450 1A1 which has retained the catalytic activity of catalyzing 7-ethoxyresorufin O-deethylation and benzo(a)pyrene 3-hydroxylation. A particular recombinant human cytochrome P450 1A1 protein is shown in the amino acid sequence of SEQ ID NO: 5.

These and other aspects of the invention will become apparent to one with skill in the art, especially in view of the following examples. All references cited herein are incorporated by reference.

EXAMPLE 1

Expression of Modified Human Cytochrome P450 3A4 in *Escherichia coli* and Purification and Reconstitution of the Enzyme

MATERIALS AND METHODS

Contruction of expression plasmids. The expression vector pCW was obtained from Prof F. W. Dahlquist, Univ. of Oregon, Eugene, Oreg. The yeast expression plasmid pAAH5/NF25 was used as the source of the cDNA for P450 3A4, originally isolated in this laboratory (Brian et al. *Biochemistry* 29:11280–11292, 1990, Beune et al. *Proc. Natl. Acad. Sci USA* 83:8064–8068, 1986). Subcloning was performed in *E. coli* strains UT481 and MC1060. All manipulations were checked by diagnostic restriction digests and the successful construct (NF14) was sequenced (Sanger et al. *Proc. Natl Acad. Sci. USA* 74:5463–6467, 1977) to confirm changes made to the NF25 cDNA, using T7 polymerase (Sequenase Version 2.0, U.S. Biochemical, Cleveland, Ohio) according to the supplier's instructions. pCW/NF1, containing the native P450 3A4 nucleotide and coding sequence (FIG. 1), was constructed by cloning the NcoI-NsiI restriction fragment of P450 3A4 into the NdeI site of pCW using oligonucleotide linkers (FIG. 2). The 5' (NdeI-NcoI) linker contained the sequence for the first eight codons of NF25 (Brian et al, 1990), which are lost upon NcoI digestion; the NdeI site coincided with the initiator ATG so that latter was suitably positioned with respect to the ribosomal binding site and tandem tac promoter sequences of pCW. The 3' (NsiI-NdeI*) linker contained an NdeI complementary end but lacked terminal bases of the recognition sequence for this enzyme; the 3' NdeI site was thus abolished in the resultant construct pCW/NF1. The CheW gene of pCW, which follows the NdeI cloning site and is unnecessary for expression, was excised by a subsequent NsiI/SalI digestion of pCW/NF1 followed by S1 nuclease trimming and religation of the blunt-ended, linearized plasmid.

Constructs pCW/NF10 and NF12, containing truncated native and truncated modified amino terminal sequences (FIG. 1), were derived by replacement of the NdeI-EcoRI fragment from pCW/NF1 with oligonucleotide linkers containing the required modifications. pCW/NF13 (native amino acid sequence, modified nucleotide sequence) and NF14 (modified amino acid and nucleotide sequence; FIG. 1) were constructed similarly (FIG. 2); however, the modified NdeI-EcoRI fragment was derived from PCR amplification using Pfu polymerase and primers coding for the required sequence changes. PCR primers for NF14 were as follows: sense-5'TTA GGA GGT CAT ATG GCT CTG TTA TTA GCA GTT TTT CTG GTG CTC CTC 3' (SEQ ID NO: 12); antisense-5' GAG GTG TGG GCC CTG GAA TTC CAA GCT TCT TAA AAA 3' (SEQ ID NO: 13).

Expression of plasmids in *E. coli*. For comparison of expression levels, *E. coli* DH5αF'IQ™ Max Efficiency Competent cells (Gibco-BRL, Grand Island, N.Y.) were transformed with each plasmid and selected on LBamp plates (Sambrook et al. *T. Molecular Cloning. A Laboratory Manual*, 2nd Ed., Cold Spring Harbor, N.Y.: Cold Spring Harbor Laboratory Press, 1989). Single isolated colonies were grown shaking at 37° C. overnight in LBamp media and then diluted 1:100 in modified TB media [12 g bactotryptone, 24 g yeast extract, 2 g bactopeptone, and 4 ml glycerol (liter)$^{-1}$] containing 100 mg ampicillin liter$^{-1}$, 1.0 mM IPTG, and 1.0 mM thiamine and supplemented with trace elements (Fisher et al. *Proc. Natl. Acad. Sci USA* 89:10817–10821, 1992). For preliminary assessments of expression levels with different constructs, cells were shifted to 30° C. and harvested after 6, 24, or 48 h. For large scale preparations of P450 3A4/NF14, induction was carried out at 32° C. for 24 h before harvest, since these conditions were found optimal for expression with this construct.

Harvested cultures were chilled on ice and centrifuged at $5 \times 10^3 \times g$ (4° C., 10 min). The cell pellet was weighed and resuspended in 100 mM Tris-acetate buffer (pH 7.6) containing 500 mM sucrose and 0.5 mM EDTA (15 ml buffer/g wet weight cells). Lysozyme was then added with gentle mixing (to 300 μg/g cells), and the suspension was diluted 2-fold with chilled $H_2O$ prior to incubation on ice for 30 min. The resulting spheroplasts were sedimented at $10^4 \times g$ (4° C., 10 min), resuspended in 100 mM potassium phosphate buffer (pH 7.6) containing 6 mM magnesium acetate, 20% glycerol (v/v), and 0.10 mM DTT, and frozen at −70° C. Spheroplast preparations were subsequently thawed in a water bath at room temperature and supplemented with protease inhibitors: 1.0 mM PMSF, 2.0 μM leupeptin, 0.04 U aprotinin ml$^{31\ 1}$, and 1.0 μM bestatin. Suspensions were sonicated on ice-salt baths with the tip of a Branson instrument (Branson Sonic Power Co., Danbury, Conn.) and centrifuged at $10^4 \times g$ (4° C., 20 min). Supernatants were carefully removed and centrifuged at $1.8 \times 10^5 \times g$ (4° C., 65 min). Membrane fractions sedimented by this spin were resuspended in 50 mM Tris-acetate buffer (pH 7.6) containing 250 mM sucrose and 0.25 mM EDTA using gentle homogenization. For determination of the distribution of P450 3A4/NF14 between membrane and soluble fractions, the supernatant from a $1.8 \times 10^5 \times g$ spin was further centrifuged at $2.25 \times 10^5 \times g$ (4° C., 60 min).

Characterization of P450 expression. Subcellular fractions from *E. coli* expressing P450 3A4 constructs or the vector PCW alone were diluted in 100 mM potassium phosphate buffer (pH 7.4) containing 20% glycerol (v/v) and 0.20% Emulgen 913 (w/v) and assayed for P450 by the spectral method of Omura and Sato (*J. Biol. Chem.* 239:2370–2378, 1964). P450 spectra in whole cells were estimated in a similar way, but cells were sedimented and resuspended in 100 mM potassium phosphate buffer (pH 7.4) containing 6 mM magnesium acetate and 10 mM dextrose.

Analysis of P450 3A4 apoprotein levels was made by immunoblotting. Proteins in the subcellular fractions of *E. coli* expressing the NF constructs or pCW vector alone were separated by electrophoresis on 7.5% gels (w/v) according to the method of Laemmli (*Nature* 227:680–685, 1970) and transferred to nitrocellulose (Towbin et al. *Proc. Natl. Acad.*

Sci USA 76:4350–4354, 1979, Guengerich et al. *Biochemistry* 21:1698–1706, 1982). [Pellets from the $10^4 \times g$ centrifugation step were resuspended in 5% NaDodSO$_4$ (w/v) prior to electrophoresis.] Immunoblotting was carried out as described previously (Guengerich et al., 1982) except that the rabbit anti-P450 3A4 (Guengerich et al. *J. Biol. Chem.* 261:5051–5060, 1986a) was preadsorbed against cell lysate from bacteria expressing only pCW vector. Lysate was incubated for 4–24 h at 4° C. with an appropriate amount of antibody and then centrifuged at $10^4 \times g$ (4° C., min) and used in immunoblotting work.

Enzyme Assays. Nifedipine oxidation (Guengerich et al., 1986a), testosterone 68,3β-hydroxylation (Brian et al., 1990) and AFB$_1$ 8,9-epoxidation and AFQ$_1$ formation (Raney et al. *Chem. Res. Toxicol.* 5:470–478, 1992) were assayed as described previously. Reconstitutions with purified P450 3A4/NF14 were undertaken using various combinations of 100 pmol P450 3A4/NF14 with the following reaction components, in a final volume of 1.0 ml of 50 mM potassium phosphate buffer (pH 7.4):NADPH-P450 reductase (usually 200 pmol), cytochrome b$_5$ (100 pmol), 200 μg sodium cholate, 20 μg of a 1:1:1 mixture of L-α-dilauroyl- and L-α-dioleyl-sn-glycero-3-phosphocholines and phosphatidyl serine (Imaoka et al. *Biochemistry* 31:6063–6069, 1992), GSH (3.0 μmol or as otherwise indicated, and either AFB$_1$ (0.05 μmol), nifedipine (0.2 μmol), or testosterone (0.2 μmol). Modifications of this procedure are presented in legends to figures as appropriate.

Predictions of relative secondary structure formation potential in mRNA. The MFOLD program adapted for Macintosh computers (Zuker, M. *Science* 244:48–52, 1989, Jaeger et al. *Proc. Natl. Acad. Sci. USA* 86:7706–7710, 1989, Jaeger et al. *Methods Enzymol.* 183:281–306, 1989) was used to predict the tendency of each N-terminal construct to form stable secondary structure around the translation start site in pCW. Specifically, bases −26 to +27 (with reference to the ATG start codon) were considered, including the Shine-Dalgarno sequence contained in pCW and the first nine codons of each coding sequence.

Purification of modified P450 3A4. Bacterial membranes from the NF14 construct were prepared as described above and then fractionated through either of two schemes (Table I). The longer procedure (Table IA) yielded an apparently homogenous preparation; the shorter procedure yielded a preparation that was ~70% pure but appears to be suitable for many uses such as catalytic activities, etc. (Table IB).

In the longer procedure [adapted from (Guengerich et al., 1986a, Yun et al. *Carcinogenesis* 13:217–222, 1992, Imaoka et al. *J. Biochem.* 102:843–851, 1987), Table IA] the bacterial membrane fraction was diluted to a protein concentration of 2 mg ml$^{-1}$ in 0.10M potassium phosphate buffer (pH 7.25) containing 1.0 mM EDTA, 20% glycerol (v/v), 0.10 mM DTT, and 0.10 mM PMSF (added directly from a stock solution in 1-propanol kept at −20° C.). Sodium cholate was added to a concentration of 0.60% (w/v) [prepared from recrystallized cholic acid and kept as a 20% aqueous solution, w/v (Guengerich, F. P. *Principles and Methods of Toxicology* (Hayes, A. W., Ed.), pp. 777–814, Raven Press, New York, 1989)]. The solubilized material was centrifuged at $10^5 \times g$ for 60 min at 4° C. and the supernatant was loaded onto a 2.5×15 cm column of n-octylamino-Sepharose 4B (Guengerich, 1989) that had been equilibrated with 0.10M potassium phosphate buffer (pH 7.25) containing 1.0 mM EDTA, 20% glycerol (v/v), 0.10 mM DTT, and 0.40% sodium cholate (at 4° C.). After the column was washed extensively with the equilibration buffer, P450 was eluted by the addition of 0.50% Emulgen 911 (Kao-Atlas, Tokyo) to the buffer. The fraction containing the P450 (assayed by A$_{417}$ measurements, NaDodSO$_4$ gel electrophoresis, and Fe$^{2+}$—CO vs Fe$^{2+}$ difference spectra) was concentrated 10-fold with the use of an Amicon PM-30 membrane device (Amicon, Danvers, Mass.) and dialyzed against several changes of 20 mM Tris-acetate buffer (pH 7.5) containing 20% glycerol (v/v), 1.0 mM DTT, and 0.40% Emulgen 911 at 4° C. The material was applied to a 20×100 mm Cosmogel DEAE FPLC column (JM Science, Buffalo, N.Y.) equilibrated with the above dialysis buffer; the P450 eluted in the void volume (done at 23° C.). The material was applied directly to a KB Type S hydroxylapatite FPLC column (6.5×100 mm, KB-Regis, Morton Grove, Ill.) equilibrated with the same buffer plus 0.20% sodium cholate. P450 3A4/NF14 was eluted (at ~350 mM phosphate) when a linear 20 to 400 mM potassium phosphate buffer gradient was applied (at 23° C.). The pooled fractions were concentrated with the use of an Amicon PM-30 membrane and dialyzed against several changes of 20 mM potassium phosphate buffer (pH 6.5) containing 20% glycerol (v/v), 0.40% Emulgen 911, and 1.0 mM DTT. This material was applied to a 7.5×75 mm Cosmogel CM FPLC column (JM Science, Buffalo, N.Y.) equilibrated with the latter dialysis buffer, and P450 3A4/NF14 was eluted with a linear gradient of 0–500 mM sodium acetate, at ~200 mM (at 23° C.). These fractions were apparently electrophoretically homogeneous; detergent was removed by applying the pool (at 4° C.) to a small (1×2 cm) column of HTP hydroxylapatite (Bio-Rad, Richmond, Calif.) equilibrated with 10 mM potassium phosphate buffer (pH 7.4) containing 20% glycerol (v/v), 0.10 mM DTT, and 0.05% sodium cholate (w/v). The column was washed extensively to remove Emulgen 911 (monitored by A$_{280}$) and then P450 was eluted with the same buffer containing 300 mM potassium phosphate. The eluted material was dialyzed against the column equilibration buffer devoid of cholate.

A shorter procedure (Table IB) was used to prepare P450 3A4/NF14 for applications that did not require complete homogeneity. The bacterial membrane fraction was suspended in 20 mM Tris-acetate buffer (pH 7.5) containing 20% glycerol (v/v), 0.40% Emulgen 911, and 1.0 mM DTT, solubilized by the addition of sodium cholate as in the case of the longer procedure, and applied directly (at 4° C.) to a 2.5×10 cm DEAE-Sephacel column (Pharmacia-LKB, Piscataway, N.J.) equilibrated with the solubilization buffer, devoid of cholate. The P450 3A4/NF14 was eluted with the equilibration buffer, slightly later than the turbid void volume fractions. The HTP hydroxylapatite procedure described above was used to remove detergent.

Purification of other enzymes. Rabbit liver NADPH-P450 reductase was purified as described by Yasukochi and Masters (*J. Biol. Chem.* 251:5337–5344, 1976) as modified by Shimada et al. (*J. Biol. Chem.* 261:909–921, 1986). Human liver samples were obtained from organ transplant donors from Tennessee Donor Services. Human liver P450 3A4 was purified from microsomes (liver sample HL104) in the same manner (longer procedure, as in Table IA) as described for the bacterial P450 3A4/NF14 product (vide supra); the specific content was 19 nmol P450 (mg protein)$^{-1}$ and N-terminal sequence analysis was identical to that reported earlier (Bork et al. *J. Biol. Chem.* 264:910–919, 1989). Cytochrome b$_5$ was purified from human liver sample HL104 using FPLC techniques as described by Funae and Imaoka (*Biochim. Biophys. Acta* 841:119–132, 1985). The purified material was electrophoretically homogeneous and spectral analysis (Spatz and Strittmatter *Proc. Natl. Acad. Sci. USA* 68:1042–1046, 1971, Omura and Takasue *J. Bio-* chem. 67:249–257, 1970) indicated 50 nmol cytochrome $b_5$ (mg protein)$^{-1}$.

Other methods. NaDodSO$_4$-polyacrylamide gels were stained with ammonical silver as described by Wray et al. (Anal. Biochem. 118:197–203, 1981). P450 concentrations were estimated spectrally using the method of Omura and Sato, 1964. N-Terminal sequence analysis was done in the Vanderbilt facility using a modified Applied Biosystems 470A instrument (Applied Biosystems, Foster City, Calif.). Yields at each cycle were estimated by comparison with external standards.

RESULTS AND DISCUSSION

Choice of sequence constructions. N-Terminal modifications were designed in light of the results of earlier studies on P450 expression in E. coli: truncation of the hydrophobic tail (Larson et al. Proc. Natl. Acad. Sci. USA 88:9141–9145, 1991) and modification of the N-terminus to include GCT as the second codon, increase AT richness, and reduce the potential of self-hybridization of the mRNA transcript (Barnes et al. Proc. Natl. Acad. Sci. USA 88:5597–5601, 1991) have facilitated P450 2E1 and P450 17A expression respectively. Five constructs (FIG. 2) were made and tested in E. coli DH5a cells; NF1 contained the native nucleotide sequence of P450 3A4; NF10 contained a sequence truncated by removal of codons 3–24; NF12 was truncated and had the Barnes et al., 1991 P450 17A N-terminus supplied; the native amino acid sequence was retained in NF13, however the nucleotide sequence was modified to minimize the potential for secondary structure formation in the transcript; NF14 had the P450 17A N-terminus (Barnes et al., 1991) aligned optimally with the original 3A4 sequence.

Figure 3:
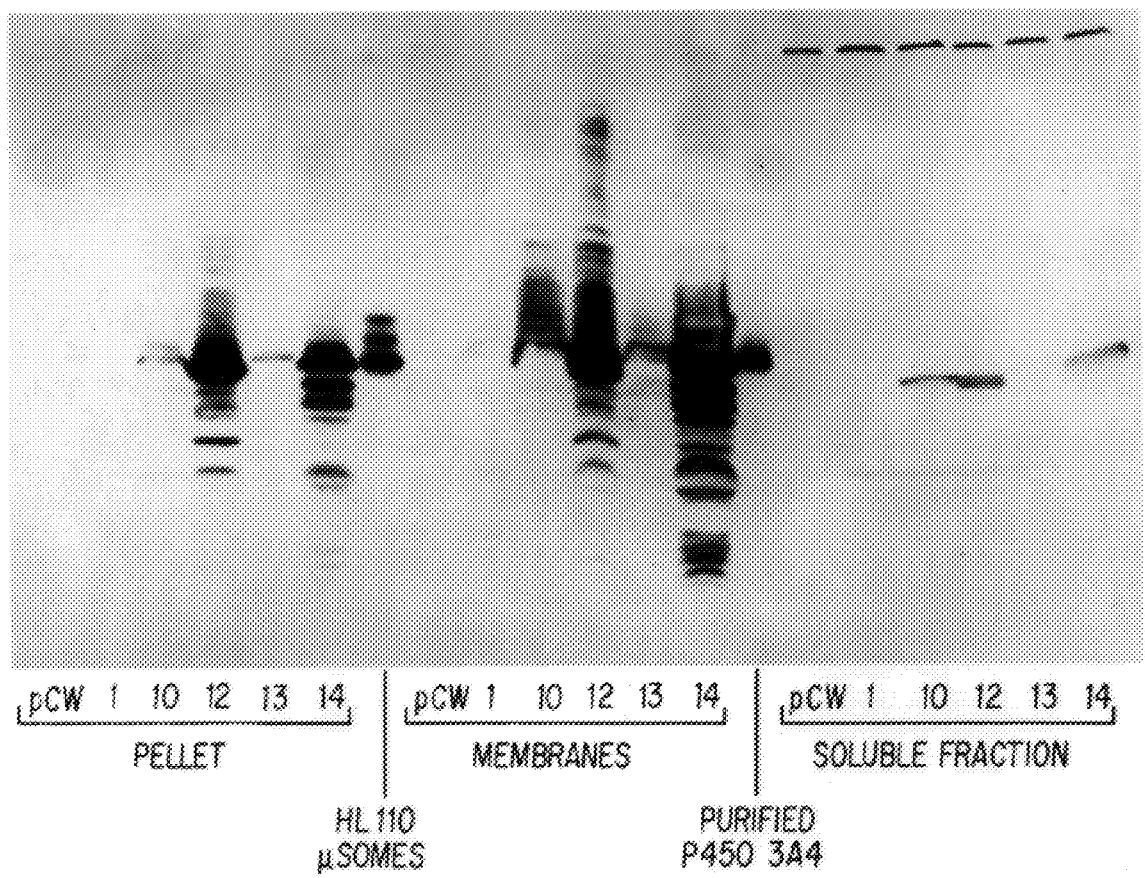
FIG. 3. Immunoblot of *E. coli* cells and cell fractions after expression of modified P450 3A4 constructs. The various constructs in the inclusion bodies ($10^4 \times g$ pellet), membrane fractions ($10^5 \times g$ pellet), and cytosol ($10^5 \times g$ supernatant) are labeled directly on the electrophoretogram. Each sample lane included material derived from 7.5 μg wet weight of cells; 1.2 pmol of the purified human liver P450 3A4 standard was applied and 7 μg of HL 110 human liver microsomal protein was used where indicated.
Figure 4:
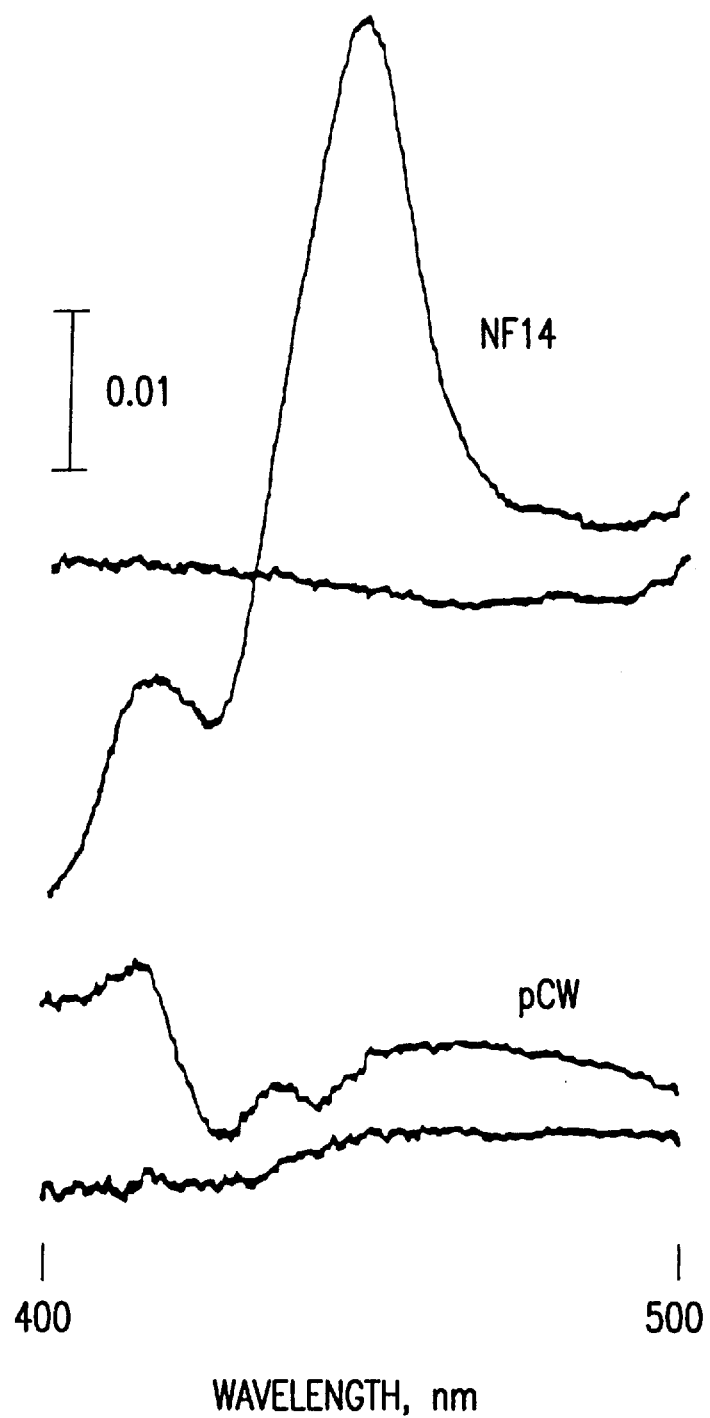
FIG. 4. $Fe^{2+}$—CO vs $Fe^{2+}$ difference spectra of *E. coli* membranes. (A) With the P450 3A4/NF14 construct; (B) with the unmodified pCW vector. Baselines ($Fe^{3+}$ vs. $Fe^{3+}$) are also shown.

Although apoprotein production was observed to some degree with all constructs, truncation of the N-terminus (NF10) led to some enhancement of apoprotein expression (FIG. 3). Significantly higher levels were obtained in conjunction with the P450 17A sequence (Barnes et al., 1991) (e.g., NF12, NF14, FIG. 3). Optimization of the nucleotide sequence without altering the coding sequence (NF13) also enhanced expression of apoprotein over the native nucleotide sequence. Apoprotein levels were generally inversely correlated with the potential for secondary structure formation of the transcript (Table II), but hemoprotein production was only detected with construct NF14 (FIG. 4). Such correlation of self-hybridization potential with expression levels has not been observed with other P450s expressed in similar systems to date in this laboratory (unpublished observations). It is of particular interest to note the lack of spectrally detectable P450 with construct NF12.

Subcellular localization and enzyme yields. Apoproteins could be detected for all constructs in the 10$^4$×g pellet ('pellet'), 10$^4$×g supernatant, 1.8×10$^5$×g supernatant ('cytosol') and 1.8×10$^5$×g pellet ('membranes') fractions (FIG. 3). Approximately equal levels of protein were sequestered in the 'pellet' fraction (representing material in inclusion bodies and unbroken cells, recoverable only by solubilization with NaDodSO$_4$) as in membranes. For the NF14 construct a typical P450 spectrum could be observed in the 10$^4$×g supernatant and membrane fractions; assay of intact cells also revealed a Fe$^{2+}$—CO peak at 450 nm. Further fractionation of the 1.8×10$^4$×g supernatant by centrifugation at 2.25×10$^5$×g resulted in complete sedimentation of both apoprotein and spectrally detectable hemoprotein, suggesting negligible expression in the soluble fraction.

Optimization of expression of the P450 3A4/NF14 construct included an assessment of induction temperature (28°–37° C.) and time (8–48 h) as well as supplements to the culture medium (1.0 mM NaCl, 1.0 mM MgCl$_2$, 2.5 mM NH$_4$SO$_4$, 50 μM FeCl$_3$). The best induction time was 24 h and the best temperature was 32° C.; however, none of these supplements enhanced P450 or cell yield significantly over normal intra-batch variation. Cell mass was found to be the most significant factor determining P450 yield. The inclusion of protease inhibitors in addition to PMSF alone was found to significantly enhance recovery of P450 during fractionation.

Yields of spectrally determined P450 3A4/NF14 hemoprotein ranged from 200–370 nmol (liter culture)$^{-1}$ measured in whole cells, 60–100 nmol (liter culture)$^{-1}$ measured in 10$^4$×g supernatants, and 40–110 nmol (liter culture)$^{-1}$ measured in the membranes after fractionation.

Figure 5A:
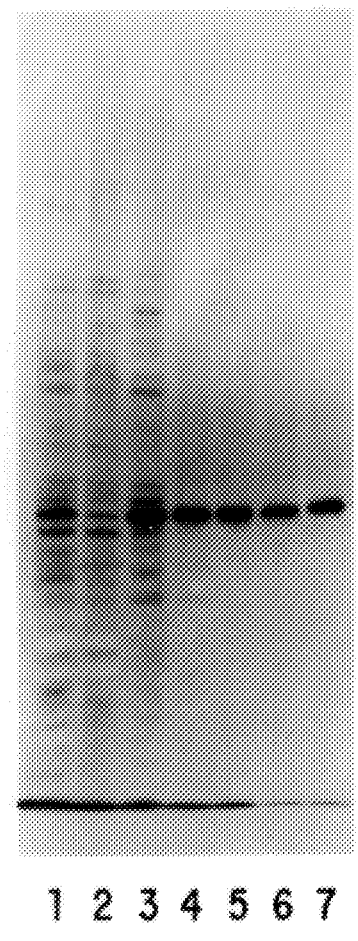
FIG. 5. $NaDodSO_4$-polyacrylamide gel electrophoresis of P450 3A4/NF14 fractions. Staining was with ammonical silver (Wray et al., 1981). Panel A: fractions from the long procedure of Table IA. Lane 1, solubilized membrane fraction (2.2 μg protein, 0.7 pmol P450); 2, n-octylamino-Sepharose void fraction (1.8 μg protein, 0.1 pmol P450); 3, n-octylamino-Sepharose eluate fraction (1.2 μg protein, 3.7 pmol P450); 4, Cosmogel DEAE void fraction (1.1 μg protein, 2.8 pmol P450); 5, KB Type-S hydroxylapatite fraction (0.7 μg protein, 3.2 pmol P450); 6, Cosmogel CM fraction [1.8 μg protein (nominal), 3.0 pmol P450]; 7, Bio-Rad HTP hydroxylapatite fraction (0.16 μg protein, 3.7 pmol P450). Panel B: fractions from the short procedure of Table IB. Lane 1, solubilized membrane fraction (8.9 μg protein, 2.1 pmol P450); 2, DEAE-Sephacel void fraction [3.0 μg protein (nominal), 1.2 pmol P450]; 3, Bio-Rad HTP hydroxylapatite fraction (0.3 μg protein, 5.0 pmol P450).
Figure 5B:
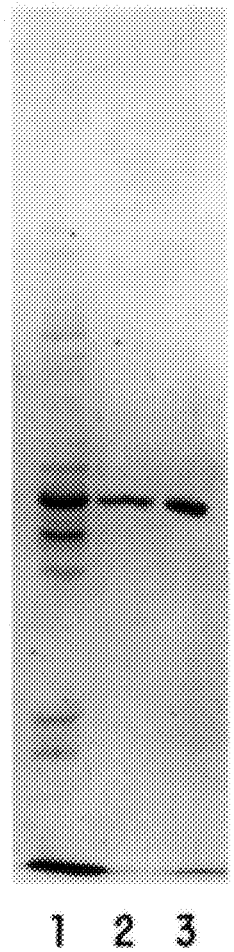
Figure 6:
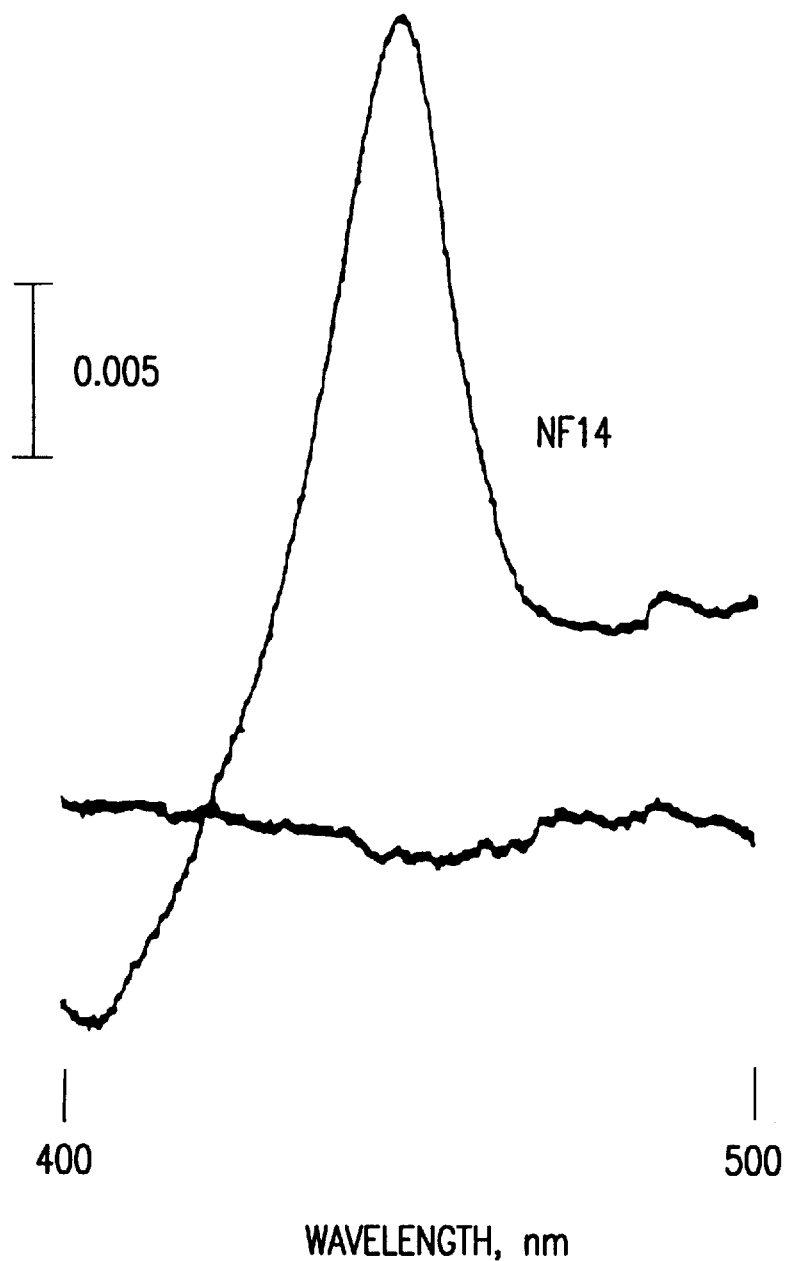
FIG. 6. $Fe^{2+}$—CO vs $Fe^{2+}$ difference spectrum of P450 3A4/NF14 purified from *E. coli* DH5α. The procedure of Table IB was used.

Purification of P450 3A4/NF14. The modified P450 3A4/NF14 was purified to electrophoretic homogeneity using a procedure employing n-octylamino-Sepharose chromatography and FPLC that had been developed for the purification of P450 3A4 from liver microsomes (Yun et al. 1992) (Table IA). Electrophoretograms of the fractions recovered at individual steps are shown in FIG. 5A. The overall yield of P450 was only 5%, however, with the greatest loss coming in the first step, n-octylamino-Sepharose chromatography (Table IA). The most effective step in the procedure was DEAE chromatography, which gave high recovery (Table IA) and extensive purification (FIG. 5A). This information was used to develop a more convenient procedure for the isolation of a highly purified preparation of P450 3A4/NF14. Solubilized bacterial membranes were applied directly to an open DEAE column (DEAE-Sephacel). The material that eluted just after the void volume under these conditions was highly purified (FIG. 5B). After removal of detergent by hydroxylapatite chromatography (Table IB), the material showed typical near-UV spectral properties (FIG. 6, similar to spectra for longer procedure) and was catalytically active (vide infra). The specific content was 15 nmol P450 (mg protein)$^{-1}$ (Table IB); that value and the electrophoretogram (FIG. 5) indicate that this preparation is ~70% pure.

N-Terminal amino acid sequence analysis. Five separate attempts were made to obtain the N-terminal sequence of purified P450 3A4/NF14, using amounts in the range of 50–100 pmol. In every case no products were obtained in the Edman procedure. However, similar analysis of P450 3A4 isolated from human liver (19 pmol used) yielded the expected N-terminal sequence, with the sequence beginning with Ala (Bork et al., 1989), and a repetitive yield of 90% over the first 20 cycles. Treatment of the intact protein with acylamino acid releasing enzyme (Boehringer-Mannheim, Indianapolis, Ind.) in buffer or buffer containing 4M urea did not result in any product in the Edman degradation. At this time we conclude that the N-terminus is blocked but have not determined the nature of the conjugate.

Figure 7A:
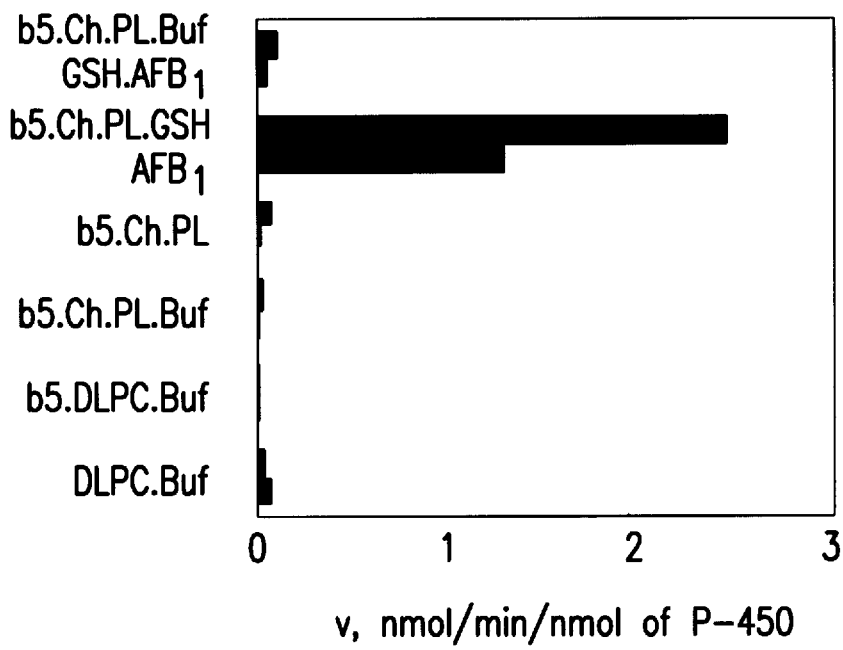
FIG. 7. Effects of reconstitution conditions on catalytic activity of P450 3A4/NF14. The various mixtures used in the preincubation with P450 3A4/NF14 and NADPH-P450 reductase (2-fold excess over P450) are indicated [$b_5$, cytochrome $b_5$ (equivalent to P450 concentration)]; Ch, cholate; PL, phospholipid mixture according to (29); DLPC, L-α-dilauroyl-sn-glycero-3-phosphocholine; NF, nifedipine; Buf, potassium phosphate buffer to the final volume. Enzyme velocity (v) is shown as nmol product formed $(min)^{-1}(nmol\ P450)^{-1}$. (A) AFB1 oxidation: 3α-hydroxylation ($AFQ_1$); 8,9-epoxidation (monitored as trapped GSH conjugate). (B) Nifedipine oxidation. When GSH is shown in parentheses, it was added (3.0 mM) after the preincubation in the concentrated mixture.
Figure 7B:
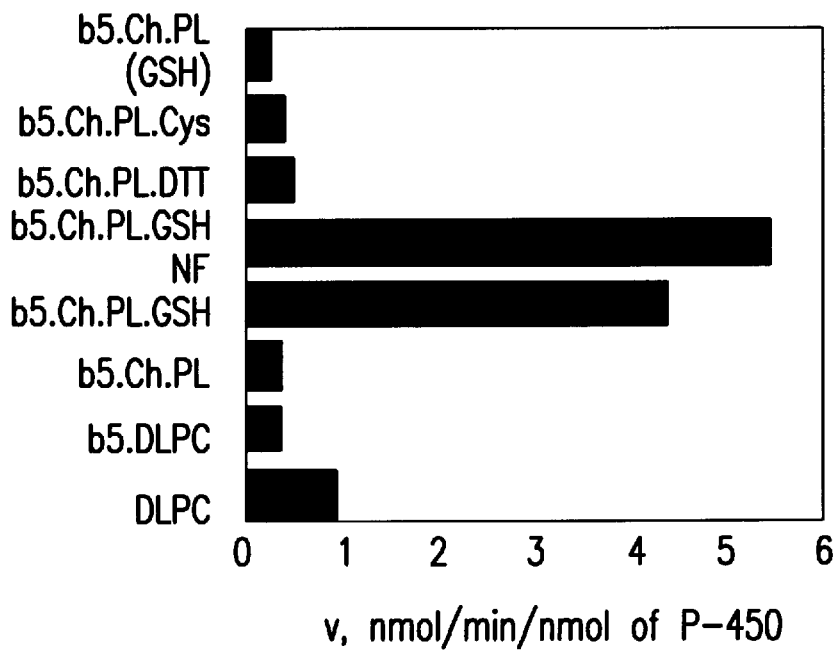
Figure 9A:
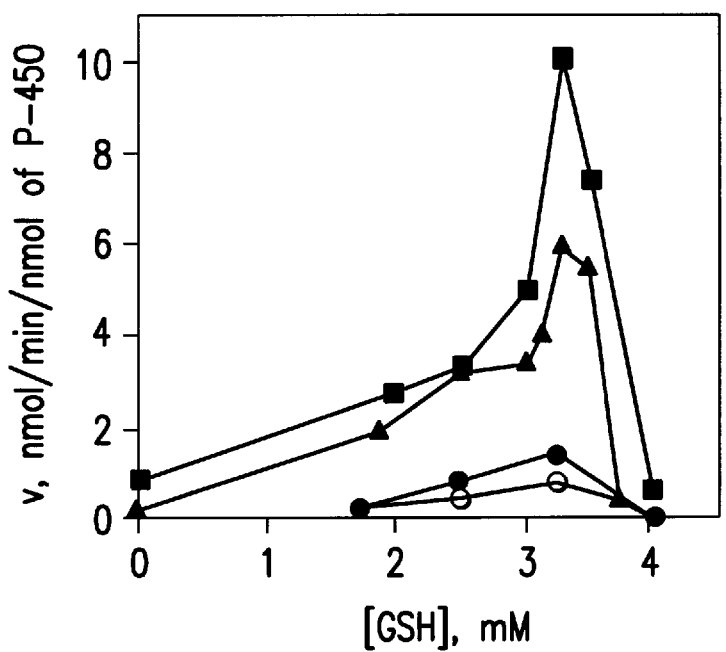
FIG. 9. Effects of GSH concentration in preincubation on oxidation of $AFB_1$, nifedipine, and testosterone. (A) Reconstitution experiments were done with P450 3A4/NF14 and rabbit NADPH-P450 reductase as described (FIG. 7 legend) in the presence of the indicated concentrations of GSH., $AFB_1$ 3α-hydroxylation; $AFB_1$ 8,9-epoxidation; nifedipine oxidation; testosterone 6B-hydroxylation. (B) Varying concentrations of GSH were added to human liver microsomal sample HL110 and nifedipine oxidation was measured following preincubation as in the case of the reconstituted system (without the addition of other detergents or lipids).
Figure 9B:
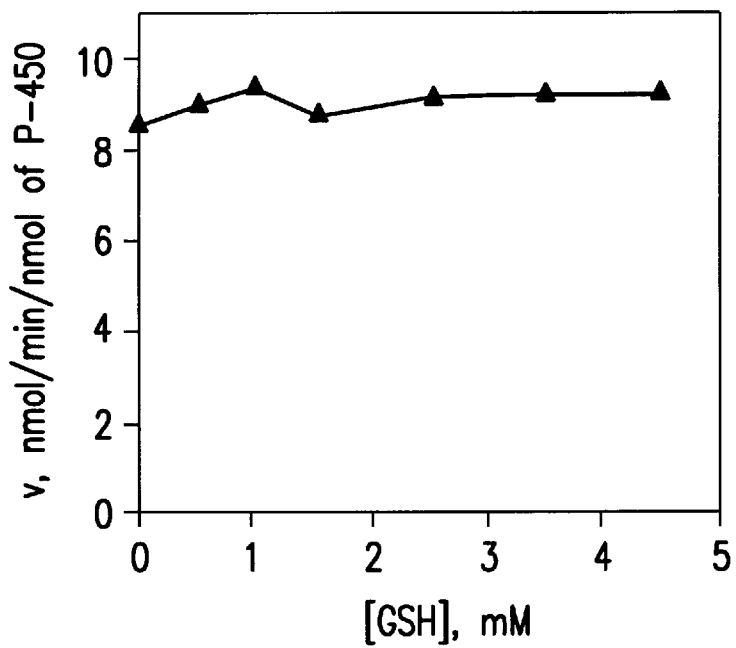

Reconstitution of catalytic activity. P450 3A4 (Guengerich et al., 1986a) and the P450 3A family enzymes from experimental animals are notorious for low catalytic activity in typical lipid systems that are effective for other P450s (Elshoubagy and Guzelian J. Biol. Chem. 255:1279–1285, 1980, Schwab et al. Mol. Pharmacol. 33:493–499, 1988, Halvorson et al. Arch. Biochem. Biophys. 277:166–180, 1990, Eberhard and Parkinson Arch. Biochem Biophys 291:231–240, 1991, Imaoka et al., 1992). We examined the procedure recommended for P450 3A enzymes by Imaoka et al., 1992 and still found low activity for the oxidation of AFB$_1$. However, during the course of further investigations with the components of the conjugating system used to trap the 8,9-epoxide (Raney et al., 1992), we found a strong effect of GSH in stimulating the catalytic activity of the enzyme (FIG. 7A). This effect was seen for both formation of $AFQ_1$ and the GSH-conjugate (of the 8,9-epoxide). Optimal activity required both GSH and the phospholipids, cholate, and cytochrome $b_5$ recommended by Imaoka et al. (Imaoka et al., 1992); the GSH had to be included in the pre-incubation mixture, although the time after mixing these materials (before the reaction was diluted and proceeded) was not a factor. The same pattern of GSH dependence was seen for nifedipine oxidation and testosterone 6β-hydroxylation, two prototypic reactions of P450 3A4 (Guengerich et al., 1986a) (FIGS. 7B, 8, 9). The presence of $\geq 4$ mM GSH was inhibitory (FIGS. 8, 9). Neither DTT, Cys (FIG. 7B), nor Cys methyl ester could substitute for GSH in stimulating the reaction but N-acetylCys could (at the same concentrations as GSH). P450 3A4 isolated from liver microsomes was stimulated in the same way as the recombinant P450 3A4/NF14 protein (results not shown). However, the addition of GSH to human liver microsomes had no effect on the nifedipine oxidation activity (FIG. 9B). The GSH effect was unexpected and further studies on the mechanism of this enhancement are in progress.

Conclusions. A relatively simple and reproducible system for the expression and use of human P450 3A4 is presented here. A slightly shortened version of the protein can be produced at a relatively high level in *E. coli* under simple growth conditions. The protein can be purified to ~70% homogeneity in one basic step (DEAE-Sephacel chromatography), adaptable to batch conditions, with removal of detergent in a second step. The enzyme shows good catalytic activity towards several known P450 3A4 substrates in a reconstitution system that has been reproducible and yields turnover numbers almost as high as seen in liver microsomes. The activity of this enzyme was shown for $AFB_1$, testosterone, and nifedipine. We have also found such a reconstituted enzyme active in cyclosporin oxidation (results not presented). It is conceivable that the modification of the N-terminus might alter the catalytic specificity of the enzyme but no obvious changes have been detected yet. In summary, it appears to be possible to use the procedures we have described to isolate P450 3A4 without access to human tissues and to use the expressed enzyme in biochemical and other studies. Ultimately this approach may be of use in areas such as generation of drug and steroid metabolites, preparation of antigen for antibody production, and even biodegradation and large-scale synthesis applications.

TABLE I

Purification of P450 3A4/NF14 from *E. coli* membrane fraction

| Purification Step | Protein (mg) | P450 (nmol) | Specific Content (nmol/mg) | Yield (%) |
|---|---|---|---|---|
| A. Long Procedure | | | | |
| Solubilized membranes | 145 | 47.5 | 0.3 | 100 |
| Octylamino Sepharose | 6.1 | 15.4 | 2.5 | 32 |
| Cosmogel DEAE | 6.0 | 15.0 | 2.5 | 31 |
| KB Type-S | 2.0 | 9.5 | 4.8 | 20 |
| Cosmogel CM | 2.3[a] | 3.9 | 1.7[a] | 8 |
| Hydroxylapatite | 0.10 | 2.3 | 23 | 5 |
| B. Short Procedure | | | | |
| Solubilized membranes | 408 | 90 | 0.2 | 100 |
| DEAE-Sephacel | 84[a] | 31 | 0.4[a] | 34 |
| Hydroxylapatite | 1.3 | 20 | 15 | 22 |

[a]These values are probably unreliable because the protein concentration seems overestimated due to detergent interference (see also FIG. 3).

TABLE II

Calculated potential free energy for RNA secondary structure formation (base region of −26 to +27, with respect to ATG start codon) and P450 3A4 yields in *E. coli* membranes.

| Construct | Secondary structure formation, potential $\Delta G$[b] | Approx. expression yield (relative to NF14) |
|---|---|---|
| P450 17A (modified) | −4.8—5.0 | |
| NV1 (native P450 3A4 nt and aa sequence)[a] | −9.2 | 2 |
| NF10 (shortened P450 3A4, aa #3-#24 removed) | −6.9 | 20 |
| NF12 (shortened P450 3A4, aa #3-#32 removed) + P450 17A N-terminus, not aligned optimally) | −4.8—5.0 | 88 |
| NF13 (optimized P450 3A4 nt sequence, native aa sequence) | −5.4—5.6 | 16 |
| NF14 (P450 3A4 with P450 17A N-terminus aligned, shortened only to position of best alignment) | −4.8—5.0 | 100 |

[a]nt = nucleotide, aa = amino acid
[b]As calculated by MFOLD program.

EXAMPLE 2

Expression of Modified Cytochrome P450 2C10 (2C9) in *Escherichia coli*, Purification, and Reconstitution of Catalytic Activity Materials and Methods Construction of expression plasmids. The expression vector pCW was obtained from Prof. F. W. Dahlquist, Univ. of Oregon, Eugene, Oreg. The yeast expression plasmid pAAH5/MP-8 (Brian et al. *Biochemistry* 28:4993–4999, 1989) was used as the source of the cDNA for P450 2C10, a clone originally isolated in this laboratory (Umbenhauer et al. *Biochemistry* 26:1094–1099, 1987). Subcloning was performed in *E. coli* strain DH5αF'IQ™ max efficiency competent cells (Gibco-BRL, Grand Island, N.Y.). The N-terminal of the P450 2C10 cDNA was modified for maximal expression (see FIG. 10). All modifications were introduced by PCR mutagenesis. The constructs were incorporated into the pCW vector by introducing an NdeI site (CATATG) to include the start codon and an XbaI site (TCTAGA) following the stop codon. The native P450 2C10 sequence was modified in two ways. In one instance, the N-terminal of P450 2C10 was aligned with that of bovine P450 17A and the amino acid sequence MALLLAVF (SEQ ID NO: 6) (Barnes et al., 1991) was introduced at the N-terminal. The 5' PCR primer for this construct contained the sequence CATATGGCTCTGTTATTAG-CAGTTTTTGTGCTCTGTCTC (SEQ ID NO: 22) (construct 2C1028). In another construct (2C1029) the hydrophobic segment of the N-terminal (i.e., amino acid residues 3–20) were removed and codons 21–26 were optimized for expression without changing the amino acid sequence. The sequence of the 5' PCR primer for this construct (2C1029) was CATATGGCTCGACAATGT-TCTGGACGAGGAAAACTCCCT (SEQ ID NO: 23).

Abbreviations used are: P450, cytochrome P450 [also termed heme thiolate protein P450 (Palmer and Reedijk *J. Biol. Chem.* 267:665–677, 1992); for current guide to nomenclature see (Nebert et al. *DNA Cell Biol.* 10:397–398, 1991)]; PCR, polymerase chain reaction; PMSF, phenylmethyl-sulfonyl fluoride (α-toluenesulfonyl fluoride); DTT, dithiothreitol; FPLC, fast protein liquid chromatography; $NaDodSO_4$, sodium dodecyl sulfate.

Expression of plasmids in *E. coli*. A single ampicillin resistant colony of either *E. coli* JM109 (Invitrogen, San Diego, Calif.) or DH5α cells transformed with plasmid DNA was grown overnight at 37° C. in Luria-Bertani (LB) medium containing 100 mg ampicillin $ml^{-1}$. A 10 ml aliquot was used to inoculate 1 liter of Terrific Broth (TB) containing 0.20% bacto-peptone (w/v). The TB media was supplemented with ampicillin (100 mg $ml^{-1}$), 1 mM thiamine, and trace elements [0.25 ml of stock preparation (liter of culture)$^{-1}$-composition: 27 g $FeCl_3.6H_2O$, 2 g $ZnCl_2.4H_2O$, 2 g $CoCl_2.6H_2O$, 2 g $Na_2MoO_4.2H_2O$, 1 g $CaCl_2.2H_2O$, 1 g $CuCl_2$, 0.5 g $H_3BO_3$, and 100 ml con HCl (liter)$^{-1}$]. Induction of the tac promoters was initiated by the addition of 1 mM isopropyl β-D-thiogalactopyranoside and allowed to proceed for 24 h at 30° C. with vigorous shaking. The cells were chilled at −20° C. for 1 h and harvested by centrifugation at $4\times10^3\times g$ for 10 min. All subsequent steps were carried out at 0°–4° C. The pelleted cells were resuspended in 100 mM Tris-acetate buffer (pH 7.6) containing 500 mM sucrose and 0.5 mM EDTA [70 mg wet weight cells $(ml)^{-1}$]. Following the addition of lysozyme (0.2 mg $ml^{-1}$), the cells were gently shaken for 30 min following the addition of an equal volume of $H_2O$. The resulting spheroplasts were pelleted at $4\times10^3\times g$ for 10 min and the pellet was resuspended (0.5 g $ml^{-1}$) in 100 mM potassium phosphate buffer (pH 7.4) containing 6 mM magnesium acetate, 20% glycerol (v/v), and 0.10 mM DTT. The spheroplasts were frozen at −70° C. until further use, when they were thawed at room temperature in a water bath. The protease inhibitors leupeptin, PMSF (in 2-propanol), and aprotinin were added to final concentrations of 2 mM, 1 mM, and 0.040 U $ml^{-1}$, respectively, during thawing. Cells were lysed twice with two 20 s bursts (at 70% full power) of a Branson sonicator (Branson Sonic Power, Danbury, Conn.) while the cells were in an ice-salt bath. The resulting lysate was centrifuged at $10^4\times g$ for 10 min and the resulting supernatant was then centrifuged at $1.8\times10^5\times g$ for 65 min; the pellet (i.e., membranes) was resuspended in 50 mM Tris-acetate buffer (pH 7.6) containing 0.5 mM EDTA and 0.25M sucrose and stored at −70° C.

Characterization of P450 expression. Membranes were diluted 5-fold in 100 mM potassium phosphate buffer (pH 7.4) containing 20% glycerol (v/v) and 0.20% Emulgen 913. $Fe^{2+}$ vs $Fe^{2+}$.CO difference spectra were measured according to Omura and Sato, 1964, using a Varian Cary 210 spectrophotometer in the automatic baseline correction mode. Expression of contructs was also measured by coupled $NaDodSO_4$ polyacrylamide gel electrophoresis-immunoblotting (Guengerich et al., 1982), using rabbit anti-human P450 2C preparations described elsewhere (Shimada et al, 1986), which had been treated with *E. coli* extracts to reduce the level of antibody reaction with constitutive bacterial proteins.

Purification of recombinant P450 2C10-derived proteins. The bacterial membrane fraction was diluted to a protein concentration of 2.0 mg protein $ml^{-1}$ in 20 mM Tris-acetate buffer (pH 7.5) containing 20% glycerol (v/v), 0.40% Emulgen 911, and 1.0 mM DTT. Sodium cholate was added to a concentration of 0.60% (w/v) [prepared from recrystallized cholic acid and kept as a 20% aqueous solution, v/v (Guengerich, 1989)].

The solubilized material was centrifuged at $10^5\times g$ for 60 min at 4° C. and the supernatant was loaded onto a 2.5×10 cm DEAE-Sephacel column (Pharmacia LKB, Piscataway, N.J.) equilibrated with the dilution buffer described above. After the column was washed with equilibration buffer (~100 ml), P450 was eluted with a linear gradient of 0 to 0.20M sodium acetate in the equilibration buffer. P450 2C1029 was eluted from the column at ~25 mM sodium acetate, while P450 2C1028 was eluted at ~50 mM sodium acetate (some was also recovered in the void fraction).

Detergent was removed from these eluted fractions by application to small columns (1×2 cm) of hydroxylapatite (HTP, Bio-Rad, Richmond, Calif.) equilibrated with 10 mM potassium phosphate buffer (pH 7.4) containing 20% glycerol (v/v), 0.1 mM DTT, and 0.05% sodium cholate (w/v). Columns were washed extensively to remove Emulgen 911 (monitored by $A_{280}$), and then P450 was eluted with the same buffer containing 300 mM potassium phosphate (pH 7.4). The eluates were dialyzed against the column equilibration buffer devoid of sodium cholate.

Purification of other enzymes. Human liver samples were obtained from organ transplant donors through Tennessee Donor Services (Nashville, Tenn.). Three preparations of P450 2C9/10 were obtained from human liver microsomes (#1 and #2 from sample HL 104 and #3 from sample HL 134) according to the general method of Shimada et al., 1986. The coding sequences of the genes termed CYP 2C9 and CYP 2C10 differ in only two amino acids, 358 and 417 (Ged et al., 1987, Srivastava et al., 1991). The CYP 2C10 sequence corresponds to the first cDNA clone we isolated from this family (Umbenhauer et al., 1987). We reported that the two cDNAs now termed 2C9 (MP-4) and 2C10 (MP-8) differed considerably in their 3' non-coding sequences, and oligonucleotide probes were used to identify both groups of sequences in the mRNA of a single liver sample (Ged et al., 1988). It is conceivable that the existence of the two cDNA clones (within an expression library generated from a single individual human) is an artifact of the library construction, or that the sequences recognized by the probes are parts of other genes. Nevertheless, P450 2C9 and P450 2C10 are treated here as the products of individual genes. When proteins purified from liver are considered here, they are designated P450 2C9/10 because no amino acid sequence analysis was done in the regions where differences occur (Ged, 1988, Srivastava et al., 1991). These preparations were apparently electrophoretically homogeneous and their nominal specific contents were 17.5, 17.9 and 12.4 nmol P450 (mg protein)$^{-1}$, respectively. Cytochrome $b_5$ was purified from human liver sample HL 104 utilizing FPLC techniques (Funae and Imaoka, 1985). The purified material was electrophoretically homogeneous and spectral analysis (Spatz and Strittmatter, 1971, Omura and Takasue, 1970) indicated 50 nmol cytochrome $b_5$ (mg protein)$^{-1}$. Rabbit liver NADPH-P450 reductase was purified as described by Yasukochi and Masters, 1976, as modified by Shimada et al., 1986.

Synthesis of hydroxytolbutamide. Hydroxytolbutamide, the product of the oxidation of tolbutamide, was prepared using a procedure revised from earlier (Knodell et al. *J. Pharmacol. Exp. Ther.* 241:1112–1119, 1987). 4-Carboxybenzenesulfonamide (20 g, 0.10 mol, Aldrich) was dissolved in 300 ml of absolute $C_2H_5OH$ and the solution was purged with HCl gas. The solution was heated under reflux overnight and then concentrated to dryness in vacuo. The residue was dissolved in water and the solution was made alkaline by the addition of $Na_2CO_3$; the ethyl ester was extracted into $CH_2Cl_2$ (3 times) and the combined extracts were dried over $Na_2SO_4$, filtered through paper, and concentrated in vacuo. The product 4-carboxyethylbenzenesulfonamide (15.5 g, 68% yield) crystallized from $CH_2Cl_2$: mp 97°–99° C., fast atom bombardment (+) mass spectrum (glycerol, $(CH_3)_2SO$) (relative abundance in parentheses) m/z 230 ($[M+H]^+$, 100), 202

(M-28, 32), 184 (m-46, 84); elemental analysis—cald. for $C_9H_{11}NO_4S$: C 47.16%, H 4.80%, N 6.11%; found: C 47.33%, H 5.04%, N 6.06%. A portion of the ethyl ester (12.0 g, 60 mmol) was dissolved in 100 ml of distilled tetrahydrofuran (from LiAlH$_4$) containing NaH (4.8 g of a 60% dispersion in mineral oil, 120 mmol) at −10° C. and butyl isocyanate (6.0 g, 60 mmol) was added dropwise, with stirring, over 30 min. The reaction was allowed to come to room temperature and stirred for 2 h more, after which it was quenched by the addition of solid NH$_4$Cl and then H$_2$O. The solution was added to 200 ml of 0.5N NaOH, which was washed three times with CH$_2$Cl$_2$ (to remove residual butyl isocyanate) and then stirred at room temperature overnight to hydrolyze the ethyl ester. The pH of the solution was adjusted to <2 by the addition of 6N HCl and the resulting white precipitate was collected on a filter and washed with H$_2$O. This product, carboxytolbutamide, was dissolved in absolute C$_2$H$_5$OH to yield 9.5 g of crystals (three crops, 53% yield): mp 216°–218° C., $^1$H NMR [(C$^2$H$_3$)$_2$SO] δ 0.80 (t, 3H, CH$_3$), 1.43 (m, 2H, —CH$_2$CH$_3$), 1.30 (m, 2H, —CH$_2$CH$_2$CH$_3$), 2.93 (m, 2H, —NHCH$_2$—), 6.57 (bt, 1H, NHCH$_2$—) 8.01 (d, 2H, phenyl), 8.14 (d, 2H, phenyl). An aliquot of the carboxytolbutamide (2.0 g, 6.3 mmol) was stirred in 50 ml of distilled tetrahydrofuran under N$_2$ at 0° C. and 50 ml of a 1M solution of BH$_3$ in tetrahydrofuran (Aldrich) was added dropwise over 30 min. The solution was allowed to come to room temperature and stirred for 3 h more. Thin layer chromatography (silica gel G, Whatman LK6DF, CHCl$_3$—CH$_3$OH—conc NH$_4$OH/80-20-1/v-v-v) indicated that the reaction was essentially complete, as judged by the migration of UV-detectable material near tolbutamide (R$_f$ 0.4). H$_2$O (50 ml) was added slowly to the reaction and the pH was lowered to <2 with 6N HCl. The product, hydroxytolbutamide, was extracted into CH$_2$Cl$_2$ three times. The pooled extracts were dried with Na$_2$SO$_4$, filtered through paper, and concentrated in vacuo and the product was crystallized from C$_2$H$_5$OH/H$_2$O (1.2 g from three crops, 67% yield): mp 104.5°–106° C. [lit 98.5°–100° C. (44) and 101°–102° C. (Knodell et al., 1987)]; UV (CH$_3$OH) ε$_{228}$ 13.0 mM$^{-1}$ cm$^{-1}$ and ε$_{267}$ 2.85 mM$^{-1}$ cm$^{-1}$; fast atom bombardment (+) mass spectrum (glycerol/(CH$_3$)$_2$SO) m/z 287 ([M+H]$^+$, 100); $^1$H NMR [(C$^2$H$_3$)$_2$SO] δ 0.82 (t, 3H), —CH$_3$), 1.18 (m, 2H, —CH$_2$CH$_3$), 1.30 (m, 2H, —CH$_2$CH$_2$CH$_3$), 2.94 (m, 2H, —NHCH$_2$—), 4.59 (d, 2H, —CH$_2$OH), 5.44 (t, 1H, —OH), 6.46 (t, 1H, NH—CH$_2$—), 7.51 (d, 2H, o-phenyl, o to CH$_2$OH), 7.84 (d, 2H, m-phenyl, m to —CH$_2$OH), 10.5 (sb, 1H, —SO$_2$NH—); el. anal., cald. for C$_{12}$H$_{18}$N$_2$O$_4$S: C 50.35%, H 6.29%, N 9.79%, found: C 50.45%, H 6.36%, N 9.20%.

Other methods. NaDodSO$_4$-polyacrylamide gels were stained with ammonical silver as described by Wray et al. (Anal. Biochem. 118:197–203, 1981). Protein concentrations were estimated using a bicinchoninic acid (BCA) method (Pierce Chemical Co., Rockford, Ill.) according to the manufacturer's directions. P450 concentrations were estimated spectrally using the method of Omura and Sato, 1964. Elemental analyses were done by Galbraith Laboratories, Knoxville, Tenn. N-Terminal sequence analysis was done in the Vanderbilt facility using a modified Applied Biosystems 470A instrument (Applied Biosystems, Foster City, Calif.). Yields at each cycle were estimated by comparison with external standards.

Enzyme assays. Tolbutamide(methyl) hydroxylation (Knodell et al., 1987), (S)-mephenytoin 4'-hydroxylation (Srivastava et al. Mol. Pharmacol. 40:69–70, 1991), and (±) hexobarbital 3'-hydroxylation (Knodell et al. J. Pharmacol. Exp. Ther. 245:845–849, 1988) were assayed as described previously. (S)-[Methyl-$^{14}$C]-mephenytoin (Srivastava et al., 1991, Shimada et al. Anal. Biochem. 147:174–179, 1985) was prepared as described elsewhere. 4'-Hydroxymephenytoin was provided by Prof. G. R. Wilkinson and 3'-hydroxyhexobarbital by Prof. I. A. Blair and S. Saleh of Vanderbilt University. Incubations included either human liver microsomes containing 500 pmol of P450 or else a mixture of 50–100 pmol purified human liver P450 or purified recombinant P450 2C10 (expressed in E. coli), 250 pmol of rabbit liver NADPH-P450 reductase, and 15 nmol of L-α-dilauroyl-sn-glycero-3-phosphocholine. In the reconstituted system, the individual components were mixed in a minimal volume (<100 μl) and incubated for 3 min at 37° C. When indicated, human liver cytochrome b$_5$ was added with these components (300 pmol). The incubations were then made up (to V$_T$=0.50 ml) with the addition of (final concentrations) 50 mM Tris-HCl (pH 7.4), 0.15M KCl, 5 mM MgCl$_2$, the substrate (2.5 mM tolbutamide, 0.20 mM (S)[N-methyl-$^{14}$C]-mephenytoin, or 1.0 mM (±) hexobarbital), and an NADPH-generating system (Guengerich, 1989). Reactions proceeded for 30 min at 37° C.

Results and Discussion

Modification of P450 2C10 sequence in constructs used for expression. High levels of expression of eukaryotic P450s in E. coli have been observed following modifications to the N-terminus (Larson et al. J. Biol. Chem. 266:7321–7324, 1991b, Li and Chiang J. Biol. Chem. 266:19186–19191, 1991, Barnes et al., 1991). These modifications have included removal of the hydrophobic segment, minimization of secondary structure formation, replacement of second codon with GCT, and enhancement of AT richness (Larson et al. 1991b, Li and Chiang, 1991, Barnes et al., 1991, Zauker, M. Science 244:48–52, 1989, Jaeger et al. Proc. Natl. Acad Sci. USA 86:7706–7710, 1989a, Jaeger et al. Methods Enzymol. 183:281–306, 1989b). These factors were taken into consideration in the modification of the P450 2C10 N-terminus. Clones 2C1028 and 2C1029 were constructed for expression in E. coli DH5α cells and 2C987 and 2C988 for expression in JM109 cells (FIG. 10). The bovine P450 17A sequence containing the nucleotide sequence shown by Barnes et al., 1991, was substituted for part of the 5' sequence of construct 2C1028 to yield higher levels of expression. Construct 2C1029 was truncated by removal of residues 3–20; the second codon was changed to GCT, and AT richness was maximized for residues 21–26. The amino acid sequence of residues 21–26 was conserved but codons used were those which indicated lowest potential of self-hybridization of the mRNA transcript. It should be noted, however, that hemoprotein production was not correlated with the potential for secondary structure formation (Table I). Both constructs 2C987 and 2C988 contained the MALLLAVF (taken from SEQ ID NO: 6) sequence (Barnes et al., 1991) at the N-terminus. Residues 3–29 were truncated in construct 2C988.

Figure 11:
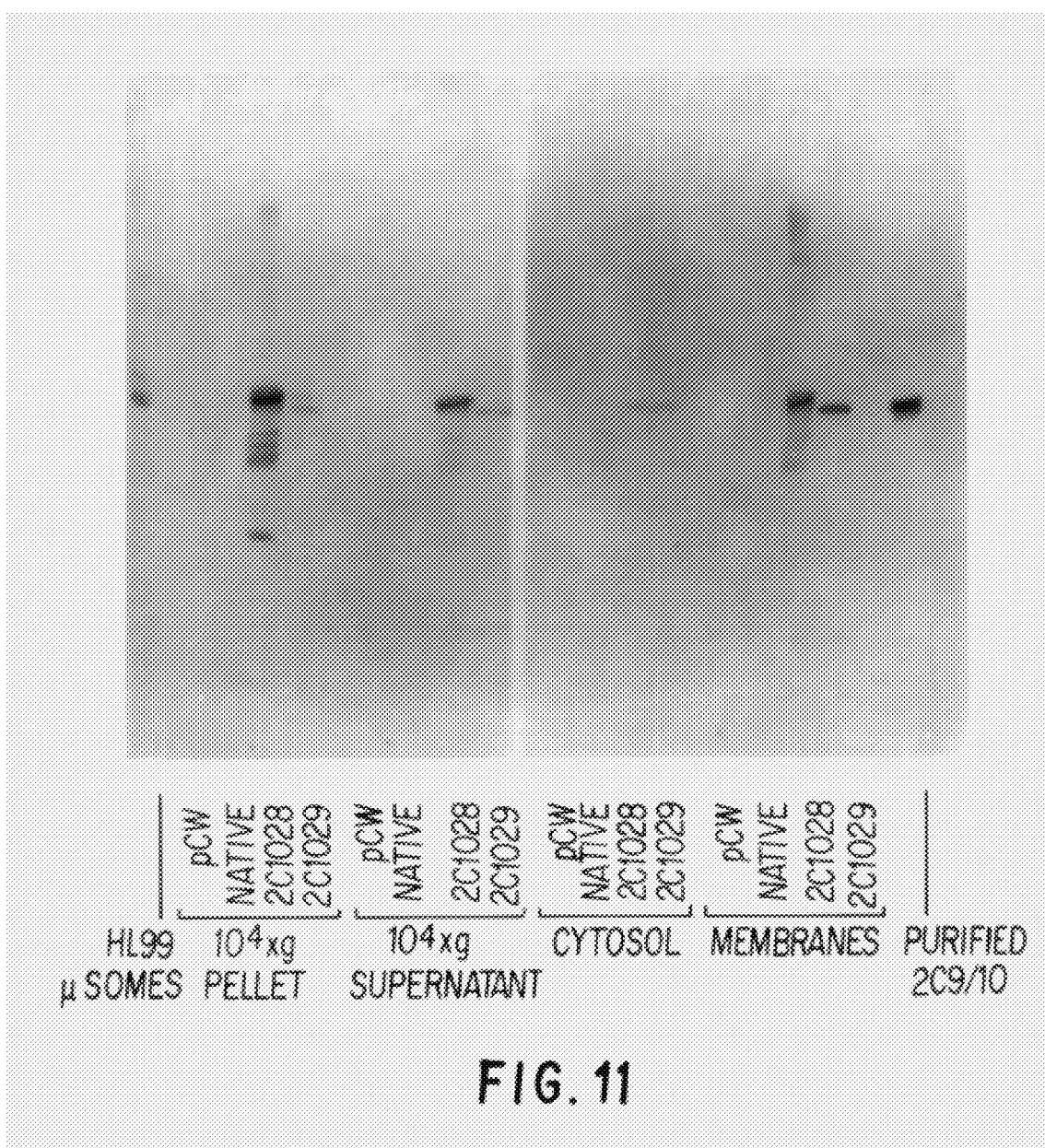
FIG. 11. Immunoblot analyses of P450 2C10 expression in *E. coli* cells. Native and modified (2C1028 and 2C1029) constructs are shown, with the $10^4 \times g$ pellet and supernatant and the $1.8 \times 10^5 \times g$ supernatant (cytosol) and pellet (membranes) fractions as indicated. Each sample lane contains material obtained from 2 μg wet weight of cells. Human liver microsomal protein (4 μg) and purified human liver P450 2C9/2C10 (1 pmol) were used as standards.
Figure 13A:
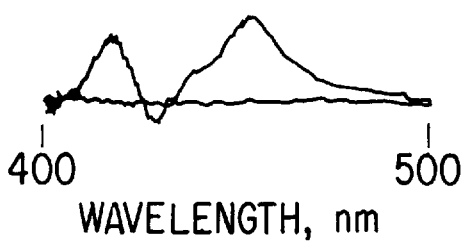
FIG. 13. $Fe^{2+}$.CO vs $Fe^{2+}$ difference spectra of P450 2C1028 and 2C1029 preparations from *E. coli*. All spectra were recorded with same absorbance settings. The $Fe^{3+}$ vs $Fe^{3+}$ baseline is shown in every case. (A) P450 2C1028; membrane fraction. (B) P450 2C1028; purified. (C) P450 2C1029; membrane fraction. (D) P450 2C1029; purified.
Figure 13B:
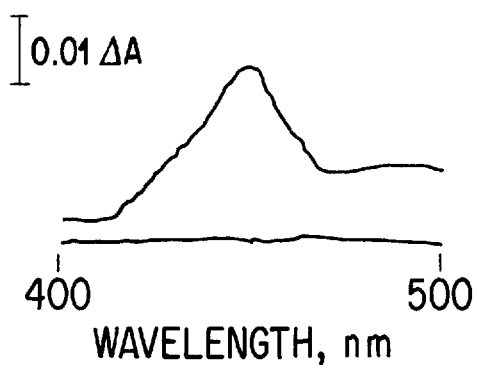
Figure 13C:
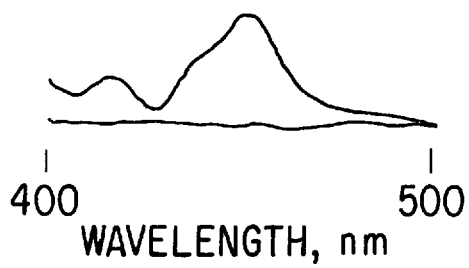
Figure 13D:
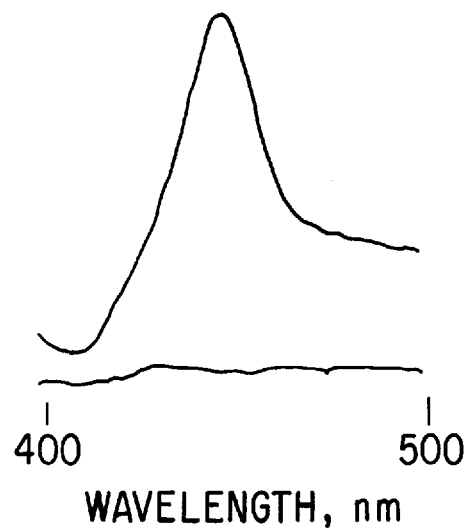

Results of immunoblotting studies indicated practically no protein production in any fraction of the native construct (FIG. 11). There were considerably higher levels of protein formation in all fractions—10$^4$×g pellet and supernatant and 1.8×10$^5$×g pellet—of construct 2C1028 as compared to construct 2C1029. Very low levels of apoproteins were detected in the 1.8×10$^5$×g supernatant (cytosol).

Subcellular localization and enzyme yields. Various conditions were employed to optimize the levels of expression of the two constructs 2C1028 and 2C1029. These included varying the temperature range between 28° and 32° C. and induction times from 4–48 h. Hemoprotein production appeared to be optimal at a temperature of 30° C. and 24 h induction time. Under these conditions the cell yield was typically ~20 g (liter of culture)$^{-1}$. The culture medium was fortified with bactopeptone, trace elements, and thiamine to optimize expression levels. The protease inhibitors PMSF, leupeptin, and aprotinin were routinely added.

Expressed P450 2C proteins were found for both constructs in the $1.8 \times 10^5 \times g$ pellets (membranes) and supernatants (cytosol), as judged by the formation of typical P450 spectra. The presence of P450 in the soluble fraction was due to cross-contamination of the cytosol with membranes, resulting from the lack of complete sedimentation. Centrifugation at a greater speed ($2.25 \times 10^5 \times g$) completely eliminated presence of P450 in the cytosol.

Yields of spectrally detectable P450 hemoprotein ranged from 5–11 nmol membrane-bound P450 (liter culture media)$^{-1}$ for construct 2C1028 and from 9–19 nmol membrane-bound P450 (liter culture media)$^{-1}$ for construct 2C1029. Recovery of P450 in membranes ($1.8 \times 10^5 \times g$ pellet) from the $10^4 \times g$ supernatant fraction was routinely >80%. Constructs 2C987 and 2C988 did not yield any spectrally detectable P450.

Purification of P450 2C10 proteins. A rapid method of purification of the P450 2C10 proteins to a high degree of purity was desired. Bacterial membranes were solubilized with sodium cholate and the non-ionic detergent Emulgen 911. Most of the P450 was bound to DEAE-Sephacel; in the case of P450 2C1028, some was recovered in the void volume fraction. P450s were eluted from the column in the early fractions when sodium acetate gradients were applied. The recovered P450 proteins were highly purified as judged by NaDodSO$_4$ polyacrylamide gel electrophoresis (FIG. 12). The recovery (from the DEAE-Sephacel column) was low in the case of P450 2C1028 but very high with P450 2C1029, the shortened sequence (Table II). In this latter case, the NaDodSO$_4$ polyacrylamide gel (FIG. 12) and the specific content of P450 (Table II) argue that the protein is >50% pure.

Both the P450 2C1028 and 2C1029 proteins showed typical P450 Fe$^{2+}$.CO vs Fe$^{2+}$ difference spectra (FIG. 13).

N-Terminal amino acid sequence analysis. Three different preparations of P450 2C9/10 purified from human liver were analyzed through at least the first 17 residues and all predicted residues were identified (Table III), except for the putative Cys residues at codons 10 and 13 [see also (Ged et al. *Biochemistry* 27:6929–6940, 1988, Umbenhauer et al., 1987, Shimada et al., 1986)]. The N-terminal Met was retained.

The P450 2C1029 protein expressed in *E. coli* showed the expected sequence, except that the N-terminal Met had been removed (Table III). Met is usually removed when Ala is in the second position in bacterial proteins (Hirel et al. *Proc. Natl. Acad. Sci. USA* 86:8247–8251, 1989).

Although all of the other proteins readily yielded reliable N-terminal amino acid sequences, the P450 2C1028 preparation did not (Table III) and we conclude that this is blocked. We have previously found that a modified P450 3A4 protein appears to be blocked when expressed in *E. coli* (Gilliam et al. *Arch. Biochem. Biophys.* 305 (in press), 1993). This is attributed to the sequence MALLAVF, which is also present there. We have also found that human P450 17A, containing the same N-terminal sequence, appears to be blocked when expressed in *E. coli*. The nature of this block is currently under investigation.

Catalytic activities of P450 2C10 proteins expressed in *E. coli*. The P450 2C1028 and P450 2C1029 proteins expressed in *E. coli* were purified and examined for catalytic activities in simple reconstituted systems containing rabbit NADPH-P450 reductase, L-α-dilauroyl-sn-glycero-3-phosphocholine, and human cytochrome b$_5$ (Table IV). Comparisons were made with human liver microsomes (sample HL104) and two preparations of P450 2C9/10 purified from that same liver sample.

P450 2C1029 showed tolbutamide hydroxylation activity similar to that of P450 2C9/10 (derived from liver) in the presence of cytochrome b$_5$; the rate with P450 2C1028 was somewhat less. While the activity of the bacterial recombinant proteins was enhanced by the addition of cytochrome b$_5$, the P450 2C preparations derived from liver were inhibited under these conditions.

None of the recombinant or isolated hepatic P450 2C proteins had (S)-mephenytoin 4'-hydroxylation activity (which was clearly observed in liver microsomes) (Table IV). The limit of detection is similar to what we have previously reported in our assays using the radiometric HPLC assay (Srivastava et al, 1991) and is in accord with our earlier conclusion that P450 2C10 (and also P450 2C9) is not the polymorphic (S)-mephenytoin 4'-hydroxylase (Brian et al., 1989, Srivastava et al., 1991). The actual P450 2C enzyme involved appears to remain unknown. Although we have not expressed P450 2C18 in bacteria as of yet, a yeast recombinant P450 2C18 did not have detectable catalytic activity [<0.01 nmol product formed min$^{-1}$ (nmol P450)$^{-1}$ ] in the absence or presence of cytochrome b$_5$. This result is in agreement with one report (Furuya et al. *Mol. Pharmacol.* 40:375–382, 1991) but not another (Romkes et al. *Biochemistry* 30:3247–3255, 1991).

Finally, it is of interest to note that the recombinant bacterial P450 2C proteins did not have detectable hexobarbital 3'-hydroxylation activity, even though activity was found in liver microsomes and yeast recombinant human P450 2C9/2C10 proteins do have activity (Brian et al., 1989, Yasumori et al. *Clin. Pharmacol. Ther.* 47:313–322, 1990). However, in these earlier reports with the yeast P450 2C10 the hexobarbital 3'-hydroxylation activity was considerably less than that of tolbutamide hydroxylation and it did not appear that the two activities were inherently tightly linked in the human P450 2C proteins (Brian et al., 1989).

Conclusions. We have described an approach for expression of human P450 2C proteins in *E. coli*. Modification of the 5'/N-terminal region appears to be very important for successful expression. Although the levels of expression we were able to obtain with these particular constructs are still relatively low, spectra of the P450 2C10 proteins can be measured and, in the case of one construct, a high degree of purification can be achieved in a single step with good yield. One of the N-terminal sequences appears to signal for a blocked N-terminus in the bacteria; the exact nature of this apparent modification has not been characterized. The partially purified P450 2C10 proteins catalyzed tolbutamide methyl hydroxylation. The response to cytochrome b$_5$ differed from the purified liver proteins, however, and there was also a difference in the ability to oxidize hexobarbital that is yet unexplained. Whether these differences are due to the modifications at the N-terminus is unknown; further, comparisons with the proteins purified from liver are difficult because of the possibility of microheterogeneity in the complex human P450 2C family. However, expression of these proteins in *E. coli* does appear to offer potential for studies on catalytic specificity and the contributions of individual amino acid residues.

TABLE I

Modified N-terminal amino acids of constructs of P450 2C10 and calculated potential free energy for RNA secondary structure formation and P450 2C10 yields in *E. coli* DH5α membranes.

| Construct | Secondary structure formation, potential ΔG° (kcal mol$^{-1}$)[a] | Approximate expression yield, mnol (liter culture)$^{-1}$ |
|---|---|---|
| Native sequence MDSLVVLVLCLSCLL . . . (from SEQ ID No: 14) | −8.4 | 0 |
| MALLAVFLCLSCLL . . . (from SEQ ID No: 15) | −4.8 to −5.0 | 0 |
| MA . . . LLLAVFLPVIG (minus residues #3–29) (from SEQ ID NO: 16) | −4.8 to −5.0 | 0 |
| MALLLAVFLCLSCLL . . . (altered amino acid usage) from SEQ ID NO: 17) | −4.8 to −5.0 | 5–11 |
| MA . . . RQSSGRGKLPPGP . . . (minus residues #3–20) from SEQ ID NO: 18) | −6.0 | 9–16 |
| MD . . . RQSSGRGKLPPGP . . . (prior to alteration of codons 21–26) from SEQ ID NO: 18) | −7.6 | —[b] |

[a](47–49)
[b]Not done. The corresponding DNA coding sequence was

TABLE II

Purification of P-450 2C1028 and 2C1029 from *E. coli* membrane fractions

| Purification Step | Protein (mg) | P-450 (nmol) | Specific Content (mnol/mg) | Yield (%) |
|---|---|---|---|---|
| P-450 2C1028 | | | | |
| Solubilized membranes | 1280 | 22 | 0.02 | 100 |
| DEAE Sephacel void/ Hydroxylapatite | 4.2 | 0.8 | 0.2 | 4 |
| DEAE-Sephacel eluate/ Hydroxylapatite | 0.5 | 0.7 | 1.4 | 3 |
| P450 2C1029 | | | | |
| Solubilized membranes | 341 | 28 | 0.08 | 100 |
| DEAE Sephacel | 11 | 21 | 1.9 | 75 |
| Hydroxylapatite | 1.3 | 12 | 9.2 | 43 |

TABLE III

N-terminal Sequences of P450 2C9/10 Purified from Human Liver Microsomes and *E. coli*.

| Cycle/ position | 2C9/10 cDNA | cDNA found | Found, pmol 1, HL104[a] | 2, HL104[b] | 3, HL134[c] | *E. coli* P450 2C1028 cDNA | Found | *E. Coli* P450 2C1029 cDNA | Found | pmol |
|---|---|---|---|---|---|---|---|---|---|---|
| 1 | M | M | 16.7 | 14.8 | 13.3 | M | Blocked | M | — | — |
| 2 | D | D | 20.5 | 26.0 | 16.8 | A | | A | A | 29.7 |
| 3 | S | S | 4.1 | 5.1 | 4.6 | L | | R | R | 15.3 |
| 4 | L | L | 12.1 | 11.29 | 12.6 | L | | Q | Q | 22.2 |
| 5 | V | V | 9.2 | 8.2 | 11.1 | L | | S | S | 9.4 |
| 6 | V | V | 1.7 | 2.6 | 2.8 | A | | S | S | 0.9 |
| 7 | L | L | 10.9 | 11.3 | 10.6 | V | | G | G | 20.0 |
| 8 | V | V | 7.2 | 6.1 | 7.9 | F | | R | R | 11.0 |
| 9 | L | L | 7.6 | 9.8 | 10.2 | V | | G | G | 15.5 |
| 10 | C | X | — | — | — | L | | K | K | 2.4 |
| 11 | L | L | 4.1 | 4.1 | 4.6 | | | L | L | 14.3 |
| 12 | S | S | 1.8 | 1.2 | 1.2 | | | P | P | 19.5 |
| 13 | C | X | — | — | — | | | P | P | 4.7 |
| 14 | L | L | 1.4 | 2.4 | 1.4 | | | G | G | 15.4 |
| 15 | L | L | 1.1 | 1.8 | 3.7 | | | P | P | 11.8 |
| 16 | L | L | 1.7 | 1.7 | 1.3 | | | T | T | 7.4 |
| 17 | L | L | 1.4 | 0.4 | 1.3 | | | P | P | 8.4 |
| 18 | S | S | 0.8 | — | 0.8 | | | L | L | 7.6 |
| 19 | L | X | — | — | — | | | P | P | 4.9 |
| 20 | W | W | — | — | 0.4 | | | V | V | 5.6 |
| 21 | | | | | | | | | I | 3.8 |
| 22 | | | | | | | | | G | 6.0 |
| 23 | | | | | | | | | N | 4.4 |
| 24 | | | | | | | | | I | 1.8 |

[a]17.5 nmol P450 (mg protein)$^{-1}$
[b]17.9 nmol P450 (mg protein)$^{-1}$
[c]12.4 nmol P450 (mg protein)$^{-1}$

TABLE IV

Catalytic activities of human liver microsomes, purified P450 2C9/10, and purified recombinant P450 2C10 expressed in E. coli
Activity, nmol product formed $min^{-1}$ (nmol P450)$^{-1a}$

| Enzyme Preparation | Tolbutamide hydroxylation | (S)-Mephenytoin 4'-hydroxylation | (±) Hexobarbital 3'-hydroxylation |
|---|---|---|---|
| Liver microsomes (sample HL 104) | 10.40 | 0.040 | 0.44 |
| Purified liver P450 2C9/10 Preparation #1 | | | |
| $-b_5$ | 2.44 | <0.01 | 0.79 |
| $+b_5$ | 0.51 | <0.01 | 1.04 |
| Preparation #2 | | | |
| $-b_5$ | 1.48 | <0.01 | 0.37 |
| $+b_5$ | 0.94 | <0.01 | 0.55 |
| E. coli P450 2C1028 | | | |
| $-b_5$ | 0.30 | <0.01 | <0.01 |
| $+b_5$ | 0.57 | <0.01 | <0.01 |
| E. coli P450 2C1029 | | | |
| $-b_5$ | 0.56 | <0.01 | <0.01 |
| $+b_5$ | 1.77 | <0.01 | <0.01 |

[a] Results are usually means of duplicate experiments.

EXAMPLE 3

Expression of Modified Human Cytochrome P450 1A2 in *Escherichia coli*: Stabilization, Purification, Spectral Characterization, and Catalytic Activities of the Enzyme

Materials and Methods

Construction of expression plasmids. The expression vector pCW was a gift from Prof. F. W. Dahlquist, Univ. of Oregon, Eugene, Oreg. The native P450 pBS/1A2 construct (Quattrochi et al. *DNA* 4:395–400, 1985, Quattrochi et al. *Proc. Natl. Acad Sci. USA* 83:6731–6735, 1986) was amplified by PCR mutagenesis. The construct was incorporated into pCW by introducing an Nde I site (CATATG) to include the start codon and a Hind III site (AAGCTT) downstream of the stop codon. Modifications were introduced to the N-terminal of P450 1A2 cDNA to optimize for expression (SEE FIG. 14). In one instance, these included alignment of P450 1A2 and bovine P450 17A with the sequence MALLLAVFL (SEQ ID NO:6) at the N-terminus. The 5' PCR primer for this construct contained the sequence ATG GCT CTG TTA TTA GCA GTT TTT CTG (SEQ. ID. NO:34) (construct 1024). In another construct (1025) the hydrophobic segment of the N-terminal—i.e., amino acid residues 3–28—was removed. This was followed by optimization of codons 29–34 for expression; the amino acid sequence of these altered codons was conserved. The sequence of the 5' PCR primer for this construct was ATG GCT AAA GGA TTA CGA CCA CGA (SEQ. ID. NO:35). All constructs were characterized by nucleotide sequence analysis to confirm the incorporated changes. Both 1024 and 1025 constructs were amplified only between the Nde I and Nco I sites. Following restriction digestion, this fragment was ligated to the Nco I-Hind III restriction fragment (of the native construct) to generate a full-length clone. Subcloning was performed in *E. coli* strain DH5αFIQ™ max efficiency competent cells (Gibco-BRL, Grand Island, N.Y.).

Expression of plasmids in *E. coli* (Gillam et al., 1993). A single ampicillin-resistant colony of either *E. coli* JM109 (Invitrogen, San Diego, Calif.) or DH5α cells transformed with plasmid DNA was grown overnight at 37° C. in Luria-Bertani (LB) medium containing 100 μg ampicillin $ml^{-1}$. A 10 ml aliquot was used to inoculate 1.0 liter of Terrific Broth (TB) containing 0.20% bacto-peptone (w/v). The TB media was supplemented with ampicillin (100 μg $ml^{-1}$), 1 mM thiamine, and trace elements [0.25 ml of stock preparation (liter of culture)$^{-1}$—composition: 27 g $FeCl_3.6H_2O$, 2 g $ZnCl_2.4H_2O$, 2 g $CoCl_2.6H_2O$, 2 g $Na_2MoO_4.2H_2O$, 1 g $CaCl_2.2H_2O$, 1 g $CuCl_2$, 0.5 g $H_3BO_3$, and 100 ml con HCl (liter)$^{-1}$]. Induction of the tac promoters was initiated by the addition of 1.0 mM isopropyl β-D-thiogalactopyranoside and allowed to proceed for 48 h at 30° C. with vigorous shaking. The cells were chilled at −20° C. for 1 h and harvested by centrifugation at $4×10^3×g$ for 10 min. All subsequent steps were carried out at 0°–4° C. The pelleted cells were resuspended in 100 mM Tris-acetate buffer (pH 7.6) containing 500 mM sucrose and 0.5 mM EDTA [70 mg wet weight cells $ml^{-1}$]. Following the addition of lysozyme (0.2 mg $ml^{-1}$), the cells were gently shaken for 30 min following the addition of an equal volume of $H_2O$. The resulting spheroplasts were pelleted at $4×10^3×g$ for 10 min and the pellet was resuspended (0.5 g $ml^{-1}$) in 100 mM potassium phosphate buffer (pH 7.4) containing 6 mM magnesium acetate, 20% glycerol (v/v), and 0.10 mM DTT. The spheroplasts were frozen at −70° C. until further use, when they were thawed at room temperature in a water bath. The protease inhibitors leupeptin, PMSF (in 2-propanol), and aprotinin were added to final concentrations of 2.0 μM, 1.0 mM, and 0.040 U $ml^{-1}$, respectively, during thawing. Cells were lysed twice with two 20 s bursts (at 70% full power) of a Branson sonicator (Branson Sonic Power, Danbury, Conn.) while the cells were in an ice-salt bath. The resulting lysate was centrifuged at $10^4×g$ for 10 min and the resulting supernatant was then centrifuged at $1.8×10^5×g$ for 65 min; the pellet (i.e., membranes) was resuspended in 50 mM Tris-acetate buffer (pH 7.6) containing 0.25 mM EDTA and 0.25M sucrose and stored at −70° C.

Characterization of P450 expression. Membranes were diluted 5-fold in 100 mM potassium phosphate buffer (pH 7.4) containing 20% glycerol (v/v) and 0.20% Emulgen 913. $Fe^{2+}$ vs $Fe^{2+}$.CO difference spectra were measured according to Omura and Sato, 1964, using an Aminco DW2/OLIS spectrophotometer (On-Line Instrument Systems, Bogart, Ga.). Expression of constructs was also measured by coupled $NaDodSO_4$ polyacrylamide gel electrophoresis-immunoblotting (Laemmli, U. K. *Nature* 227:680–685, 1970, Towbin et al. *Proc. Natl. Acad Sci. USA* 76:4350–4354, 1979), using rabbit anti-human P450 1A2 preparations.

Purification of recombinant P450 1A2. The *E. coli* membrane fraction was diluted to a protein concentration of 2 mg $ml^{-1}$ in 50 mM Tris-HCl buffer (pH 7.4) containing 30 μM αNF, 20% glycerol (v/v), 0.625% sodium cholate, 1.25% Triton N-101, 1.0 mM EDTA, and 1.0 mM DTT. Sodium cholate was prepared from recrystallized cholic acid and used as 20% aqueous stock solution (w/v).

The solubilized membrane solution was centrifuged at $10^5×g$ for 60 min at 4° C. after stirring (4° C.) for 2.5 h. The supernatant was loaded onto a 2.5×13 cm DEAE-Sephacel column (Pharmacia LKB, Piscataway, N.J.) equilibrated with the membrane solubilization buffer (vide supra). The void fractions were pooled and the Tris-HCl concentration was diluted to 25 mM (all other components were the same). The diluted solution was applied to a 2.5×6 cm column of CM Sepharose Fast-Flow (Pharmacia LKB) that had been equilibrated with 20 mM potassium phosphate buffer (pH 7.4) containing 30 μM αNF, 20% glycerol (v/v), 0.20 mM EDTA, and 1.0 mM DTT. During loading, a dark brown band formed at the top of the column. The loaded column was sequentially washed with 400 ml each of 50 mM and 100 mM potassium phosphate buffers (pH 7.4) containing 20% glycerol (v/v), 0.20 mM EDTA, and 1.0 mM DTT. The P450 1A2 protein was eluted sequentially with 300 mM and 500 mM potassium phosphate buffers (pH 7.4) containing 20% glycerol, 0.2 mM EDTA, and 1.0 mM DTT.

Purification of other proteins. Rabbit P450 1A2 was purified from liver microsomes of rabbits treated with 5,6-benzoflavone (Haugen and Coon *J. Biol. Chem.* 251:7929–7939, 1976, Haugen et al. *J. Biol. Chem.* 250:3567–3570, 1975) with slight modification of the procedure of Alterman and Dowgii (*Biomed. Chromatog.* 4:221–222, 1990): EDTA (1.0 mM) was included in all buffers and the Tris buffer concentration in the material recovered from the DEAE-Sephacel column was diluted 2-fold before application to the CM-Sepharose Fast-Flow column. The purified preparation was >95% homogenous as judged by $NaDodSO_4$-polyacrylamide gel electrophoresis (Laemmli, 1970, Wray et al., 1981).

NADPH-P450 reductase was purified from liver microsomes of phenobarbital-treated rabbits using the method of Yasukochi and Masters, 1976, with slight modification. Human liver cytochrome $b_5$ was purified to apparent homogeneity as described elsewhere (Shimada et al. *J. Biol. Chem.* 261:909–921, 1986).

Rabbit anti-human P450 1A2 was used in the immunoblotting experiments presented here. The specificity and properties of similar preparations have been reported elsewhere (Distlerath et al. *J. Biol. Chem.* 260:9057–9067, 1985). The antisera was adsorbed with *E. coli* proteins before use to remove background staining.

Other procedures and assays. Spectra were recorded with Aminco DW2/OLIS and Cary 14/OLIS (On-Line) and Varian/Cary 210 (Varian, Walnut Creek, Calif.) spectrophotometers; wavelength calibration was done with a holmium oxide standard. Protein concentrations were estimated with the bicinchonic acid ("BCA") procedure (Pierce Chemical Co., Rockford, Ill.) using the manufacturer's directions. 7-Ethoxyresorufin O-deethylation (Burke and Mayer *Drug Metab. Dispos.* 3:245–253, 1975, Burke and Mayer *Chem.-Biol. Interactions* 45:243–258, 1983) and phenacetin O-deethylation (Distlerath et al., 1985, Larrey et al. *Biochem.* 23:2787–2795, 1984) were assayed as described elsewhere. These assays were done at varying P450 1A2:NADPH-P450 reductase ratios. N-Terminal sequence analysis was done on proteins transferred from $NaDodSO_4$-polyacrylamide gels to Immobilon papers (Millipore, Bedford, Mass.) (Matsudaira, P. *J. Biol. Chem.* 262:10035–10038, 1987) using a modified Applied Biosystems 470A instrument (Applied Biosystems, Foster City, Calif.) (Shimada et al. *Mol. Pharmacol.* 41:856–864, 1992, Uyn et al. *Biochem.* 31:10556–10563, 1992).

Results and Discussion

Modifications and expression of P450 1A2 constructs. Previous studies (Larson et al., 1991b, Barnes et al., 1991, Fisher et al., 1992a, Gillam et al., 1993, Sandhu et al. *Arch. Biochem Biophys.*, in press, 1993) have indicated that modifications introduced at the N-terminus of the native protein enhance levels of expression of eukaryotic P450s in *E. coli*. These modifications have included substitution of the second codon with GCT (coding for Ala), truncation of the hydrophobic segment, enhancement of AT content, and minimization of the potential for self-hybridization of the mRNA transcript. These modifications were taken into consideration while designing constructs for purposes of expression. Constructs 963 and 964 were expressed in *E. coli* JM109 cells whereas constructs 1024 and 1025 were expressed in DH5α cells (FIG. 14). Constructs 963, 964, and 1024 contained the N-terminal nucleotide sequence shown by Barnes et al. (Barnes et al., 1991) to yield high levels of expression of bovine P450 17A. Constructs 964 and 1025 were truncated by removal of residues 3–22 and 3–28, respectively. In the case of construct 1025 the amino acid sequence of residues 29–34 was conserved but the codons used were those that indicated the lowest potential energy for secondary structure formation.

Results presented in Table I indicate, however, that hemoprotein production did not correlate with the potential energy for self-hybridization of the mRNA transcript. Constructs 963, 964, and 1024 all have $\Delta G^-$ values of −4.8 to −5.0, yet only construct 1024 was produced at high levels and capable of incorporating heme. One reason for this observation might be the difference in the cells used; i.e., constructs 963 and 964 were expressed in *E. coli* JM109 cells whereas construct 1024 was expressed in DH5α cells. In our own experience we have not routinely obtained good expression of P450 constructs in JM109 cells (Sandhu et al., 1993). Also of interest is the observation that low levels of expression (as judged by spectrally detectable P450, results not presented) were noted for the modified construct 1025. This construct, however, possesses a similar tendency for secondary structure formation (Table I) as the original 1025 construct. Both of these 1025 constructs have a greater tendency to self-hybridize (in the mRNA transcripts) than the native construct 1023 and yet the modified 1025 construct is the one that incorporates heme. These results indicate that a combination of N-terminal modifications are involved in determining whether or not expression will be successful in *E. coli*.

Results of immunoblotting experiments (FIG. 15) indicated low levels of protein production in all fractions of the native construct. No protein was detected in the cytosolic fraction isolated after expression of this construct. There were considerably higher levels of protein formation in all fractions of construct 1024—i.e., $10^4$×g pellet and supernatant and $1.8 \times 10^5$×g pellet (membranes) and supernatant (cytosol)—as compared to construct 1025. Very low levels of apoproteins were detected in the cytosolic fractions of both these constructs.

Subcellular localization and enzyme yields. Various conditions were employed to optimize expression levels of the constructs. These included initiating the isopropyl β-D-thiogalactopyranoside-inducible tac promoter at concentrations of 0.5 and 1.0 mM, varying induction time from 4–48 h and temperature from 28°–32° C., and fortification of the culture medium with bactopeptone, trace elements, and thiamine. Under these conditions the cell yield was typically ~22 g (liter culture)$^{-1}$. The protease inhibitors PMSF, leupeptin, and aprotinin were routinely added prior to isolation of membranes.

Expressed human P450 1A2 proteins were found for both constructs in the $1.8 \times 10^5$×g pellets, i.e., membranes. Yields of spectrally detectable P450 hemoprotein ranged from 225–245 nmol and 3–4 nmol membrane-bound P450 (liter culture)$^{-1}$ for constructs 1024 and 1025, respectively. The yield for construct 1024 increased 3-fold following prolongation of the induction period from 24 to 48 h. Recovery of P450 in membranes (1.8×10⁵×g pellet) from the 10⁴×g supernatant was routinely >90%. Constructs 963, 964, and 1023 did not yield any spectrally detectable P450. Since high levels of expression were obtained only with construct 1024, all subsequent studies were done using this construct.

Figure 16:
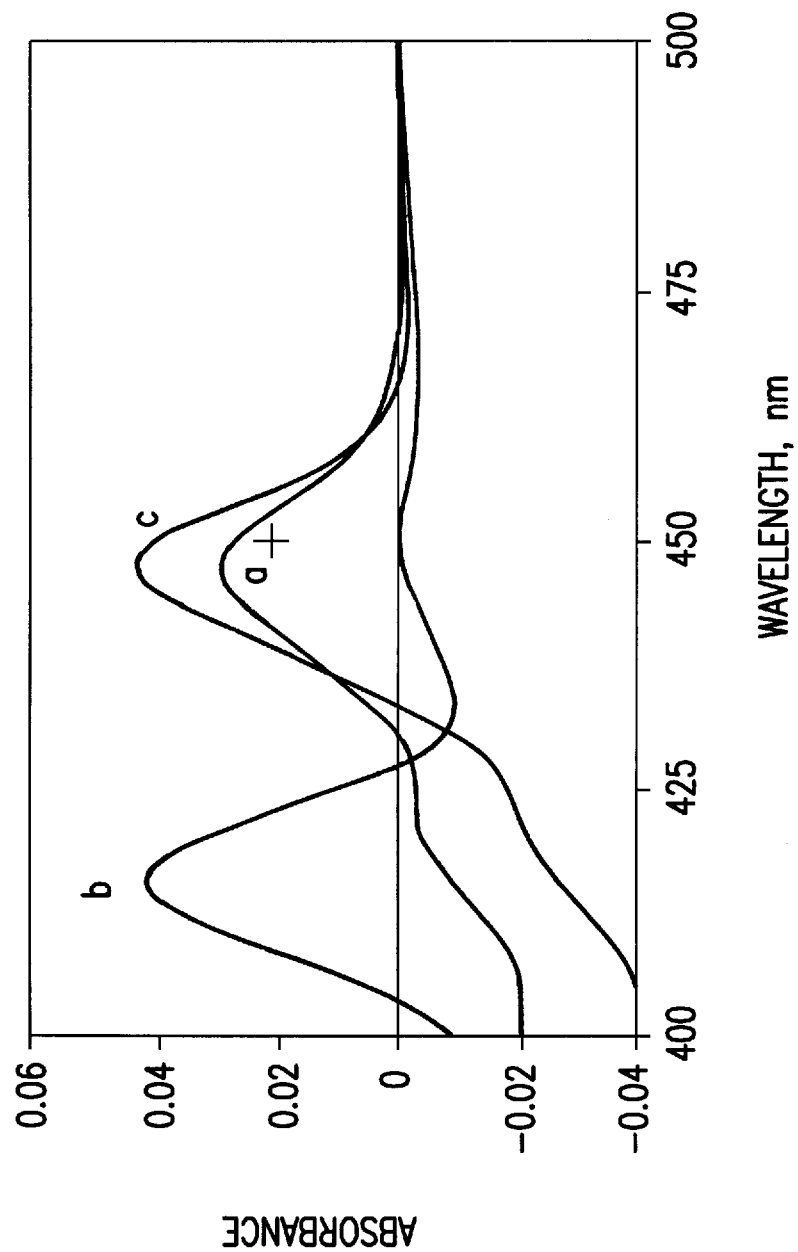
FIG. 16. Effect of αNF on the stability of recombinant P450 1A2 in *E. coli* membranes in the presence of detergents. (a) *E. coli* membranes containing 1.75 nmol P450 (~4 mg protein, 3.5 ml total volume). (b) Same as a, with addition of 0.625% sodium cholate (w/v) and 1.25% Triton N-101 (w/v). (c) Same as b, with addition of 30 μM αNF. The cross denotes the 450.0 nm point. The $I_{max}$ was 446.5 nm in a and 447.0 nm in c, as judged from the peak finder program of the Aminco DW2/OLIS system.

Stability of recombinant human P450 1A2 Fisher et al. (Fisher et al. *FASEB J.* 6:759–764, 1992b) reported that 40% of recombinant human P450 1A2 bound to *E. coli* membranes could be solubilized by the addition of the non-ionic detergent Triton X-100 (at a detergent:protein ratio of 1:2). Some P420, however, appeared to be formed after addition of the detergent during the time required for centrifugation (Fisher, 1992b). We found that detergents produced considerable conversion of the expressed P450 1A2 to P420 (FIG. 16, Table II). This destruction occurred with sodium cholate or with any of a number of non-ionic detergents examined. The destruction was concentration-dependent and could not be blocked by DTT or EDTA Many of the non-ionic detergents are prone to contain peroxides upon storage (Chang and Bock *Anal. Biochem.* 104:112–117, 1980, Ashani and Catravas *Anal. Biochem.* 109:55–62, 1980); however, we found considerable P420 formation with freshly prepared samples of the non-ionic detergents and with detergents less prone to oxidation (e.g., sodium cholate, octylglucoside) (Table II). At lower concentrations of detergent, solubilization of P450 1A2 from the membrane was incomplete.

We considered the possibility that addition of a ligand to the binding site of P450 1A2 might stabilize it during solubilization and purification, a phenomenon that has precedent in work with P450s (Larson et al., 1991b, Yu et al. *J. Biol. Chem.* 249:94–101, 1974a, Kellis and Vickery *J. Biol. Chem.* 262:4413–4420, 1987). αNF is known to be a strong competitive inhibitor of human P450 1A2 (Butler et al. *Proc. Natl. Acad. Sci. USA* 86:7696–7700, 1989, McManus et al. *Cancer Res.* 50:3367–3376, 1990). Addition of 10 μM αNF blocked the formation of P420 (Table III, second set). In the presence of 30 μM αNF, we were able to increase the detergent concentration to a point where solubilization of P450 was nearly complete, as judged by recovery after centrifugation at 10⁵×g for 60 min. No degradation of P450 to P420 could be detected (FIG. 16 and Table III, third set).

A number of known substrates of human P450 1A2 (Butler et al., 1989, Guengerich, F. P. *Drug Metab. Dispos.* 21:1–6, 1993, Fisher et al., 1992b) were tested to determine if any could block the conversion to P420 (Table III, last set). Of those examined, only caffeine was effective and not nearly so effective as αNF, which is readily available and afforded complete protection at a concentration of 30 μM.

Figure 15:
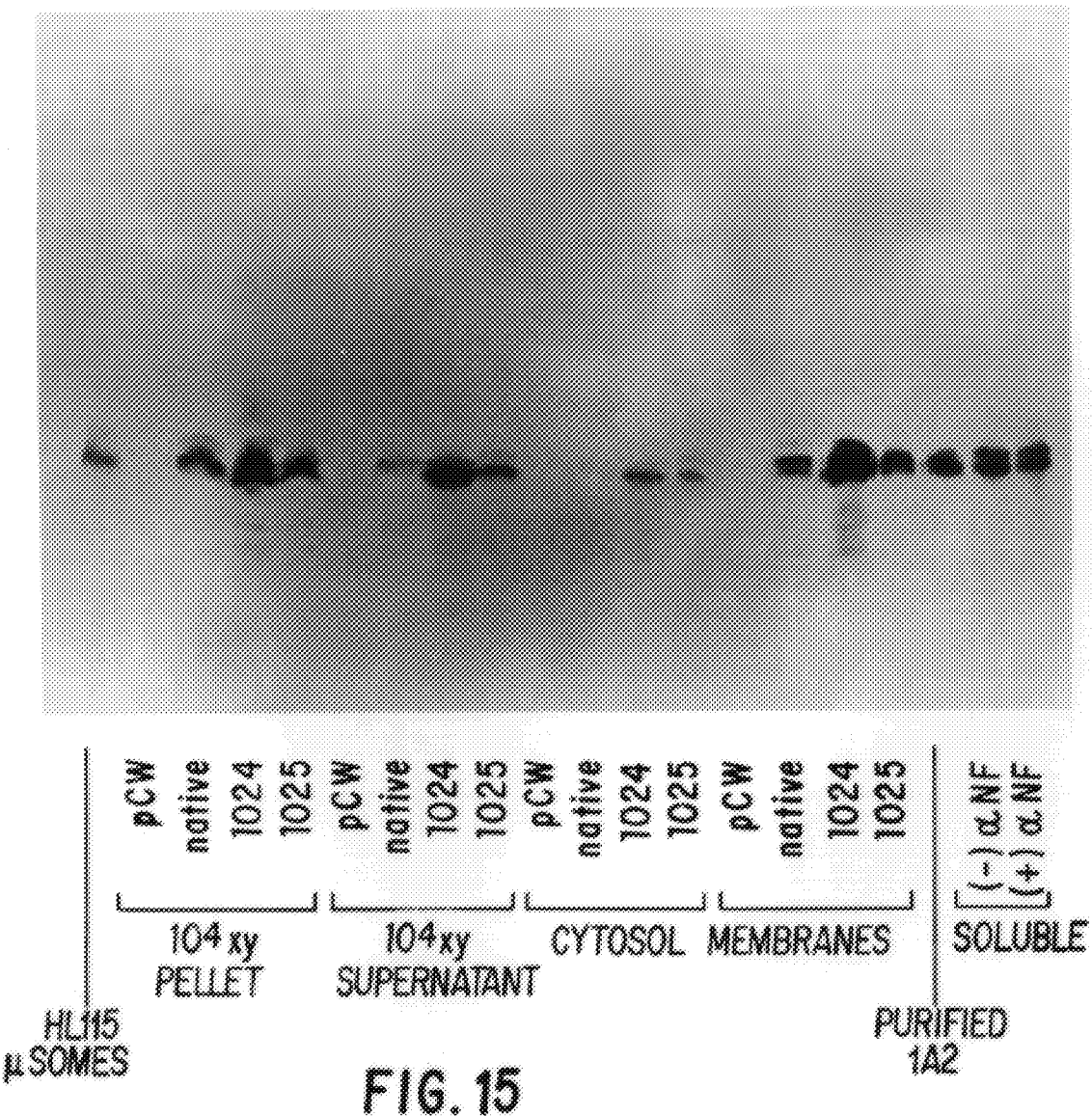
FIG. 15. Immunoblot analysis of human P450 1A2 expression in *E. coli* cells. Native (1023) and modified (1024 and 1025) constructs are shown, with the $10^4 \times g$ pellet and supernatant and the $1.8 \times 10^5 \times g$ supernatant (cytosol) and pellet (membranes) as indicated. Membranes of construct 1024 solubilized with detergent (0.625% cholate plus 1.25% Triton N-101) in the absence and presence of αNF are also shown (+αNF, -αNF). Each sample lane contains material obtained from 5 μg wet weight of cells. Human liver microsomal protein (4 μg) and purified human recombinant (construct 1024) P450 1A2 (2.5 pmol) were used as standards.

Although the bacterial membranes contain mainly P450 and little P420 (FIG. 16), we considered the possibility that supplementation of the growth medium with αNF (30 μM) might increase the yield of P450 1A2. However, no noticeable difference in the yield of spectrally detectable P450 was noted in a pilot study. Another possibility we considered was that bacterial proteases were released from the membranes upon solubilization with detergent and that the P420 formation was due to rapid proteolysis. However, when we examined the immunoblots of membranes treated with sodium cholate and Triton N-101 in the absence and presence of αNF, no obvious difference was seen (FIG. 15).

Purification of human P450 1A2 from *E. coli* membranes. Initial attempts to purify recombinant P450 1A2 from bacterial membranes were thwarted by instability of the protein in the presence of high detergent concentrations. We also found that in a protocol adapted from the one we used for *E. coli* recombinant P450 3A4 (Gillam et al., 1993), which used moderate concentrations of sodium cholate and non-ionic detergent, there was extensive binding to the DEAE-Sephacel matrix and poor recovery of protein, in addition to extensive denaturation. An attempt was made to use n-octylamino-Sepharose chromatography (Imai and Sato *J. Biochem.* 75:689–697, 1974, Guengerich, 1989) in the first step in order to avoid the addition of non-ionic detergents and to improve recovery (Tables II, III). However, the extent of solubilization was poor and there was still considerable denaturation to P420. The recovery from the n-octylamino-Sepharose column was only ~35%.

Figure 17:
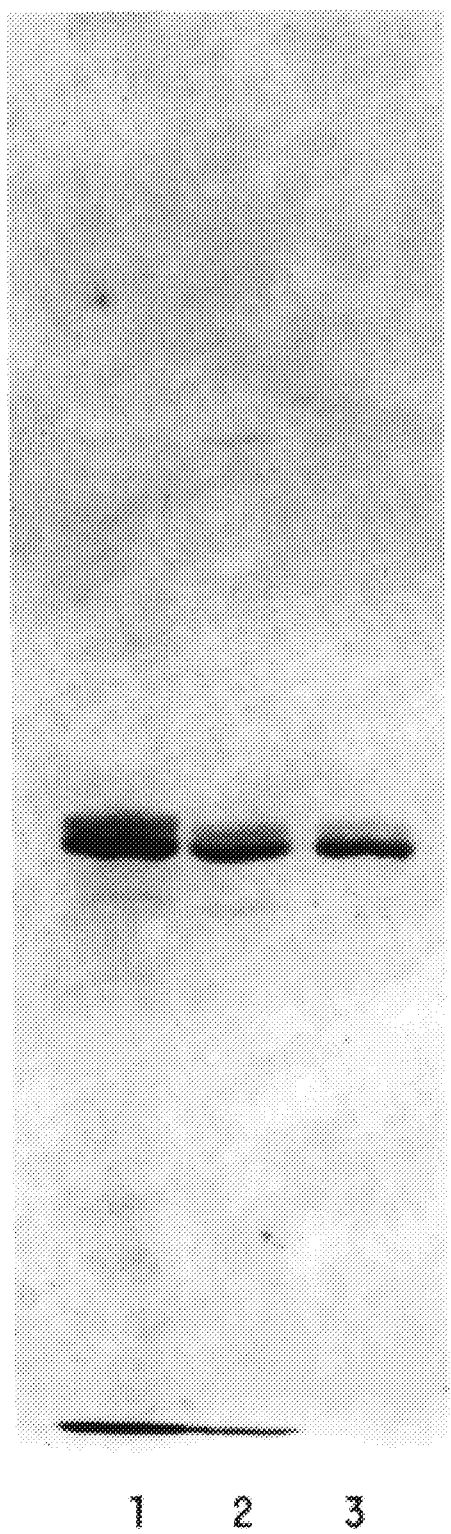
FIG. 17. Purification of recombinant P450 1A2 from *E. coli* membrane. $NaDodSO_4$-polyacrylamide gel electrophoretograms were stained with ammonical silver (34). Lane 1, membranes (35 μg protein); lane 2, DEAE-Sephacel void fraction (10 μg protein); lane 3, CM-Separose Fast-Flow fraction (1.3 μg protein).

With the discovery that αNF had a considerable protective effect in the presence of ionic and non-ionic detergents (vide supra), we decided to add αNF to buffers used in chromatography. We also employed a basic method that we found to yield essentially homogeneous rabbit P450 1A2 (from liver microsomes) in two steps, with some minor modification (Alterman and Dowgii, 1990). Thus, the bacterial membranes were solubilized with a high concentration of sodium cholate and Triton N-101 in the presence of αNF, and the supernatant recovered after centrifugation at 10⁵×g was applied directly to a DEAE-Sephacel column equilibrated with the solubilization buffer. Most of the bacterial membrane proteins were adsorbed to the column and the void volume fraction was highly enriched in P450 (FIG. 17). This fraction was diluted and applied to a CM-Sepharose Fast-Flow column (Alterman and Dowgii, 1990), which was subsequently washed with low ionic strength buffers to remove some residual proteins, detergent, and αNF. Nearly homogeneous P450 1A2 was then eluted with buffers containing high phosphate concentrations (Table IV, FIG. 17). Both the 300 and 500 mM potassium phosphate fractions appeared to be nearly pure (FIG. 17), except for a trace of a polypeptide of slightly higher $M_r$. However, this polypeptide and the lower, major one were both recognized by rabbit anti-human P450 1A2 (which had been adsorbed against *E. coli* proteins). The apparent specific content values should be considered nominal because of their dependence upon protein estimates (Table IV); however, the value of 16 nmol (mg protein)$^{-1}$ obtained for the second CM-Sepharose Fast-Flow fraction is essentially that predicted from the $M_r$ of the protein (Quattrochi et al., 1985, Quattrochi et al., 1986).

The combined yield of P450 1A2 recovered in the two CM-Sepharose eluates was 86% of that in the solubilized membranes (Table IV).

Figure 18A:
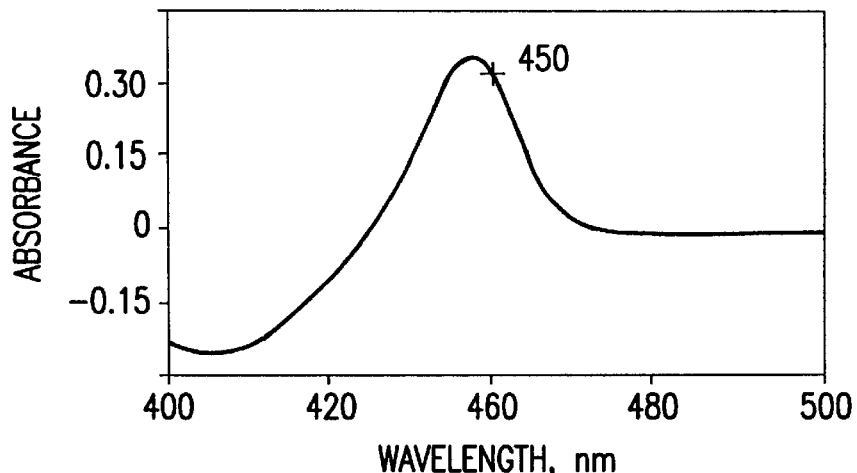
FIG. 18. Spectra of purified recombinant human P450 1A2. All spectra were recorded with 3.9 μM P450 1A2 in 100 mM potassium phosphate buffer (pH 7.4) containing 1.0 mM EDTA and 20% glycerol. CM-Sepaharose Fast-Flow fractions (300 mM phosphate) were used. (A) $Fe^{2+}$.CO vs $Fe^{2+}$ difference spectrum. The cross denotes the 450.0 nm point. (B) Absolute spectra: $Fe^{3+}$, $Fe^{2+}$, $Fe^{2+}$.CO, as indicated. (C) Second derivative spectra ($Fe^{3+}$). For further information see Table V.

Spectral properties of recombinant human P450 1A2. Under the conditions used here the P450 1A2 preparation showed little evidence of P420 in bacterial membranes (FIG. 16) or after purification (FIGS. 18A,B). The absolute spectra indicate the high portion of high-spin iron in the preparation, as noted by the diagnostic 394 and 646 nm bands of the ferric enzyme (Yu and Gunsalus *J. Biol. Chem.* 249:102–106, 1974b). The α and β bands are also coalesced. The high spin character was confirmed by second derivative analysis (Guengerich, 1983, O'Haver and Green *Anal. Chem.* 48:312–318, 1976) of the ferric Soret band (FIG. 18C). Some low spin iron ($I_{max}$ 417 nm) is present but the level appears to be ≦10%.

In other studies (results not presented), it was found that addition of either αNF (7.5 μM) or concentrations of sodium cholate and Triton N-101 used in purification studies had no detectable effect on the spin state of ferric human P450 1A2, as judged by the magnitude of the 646 nm band or second derivative analysis of the Soret band.

Figure 18B:
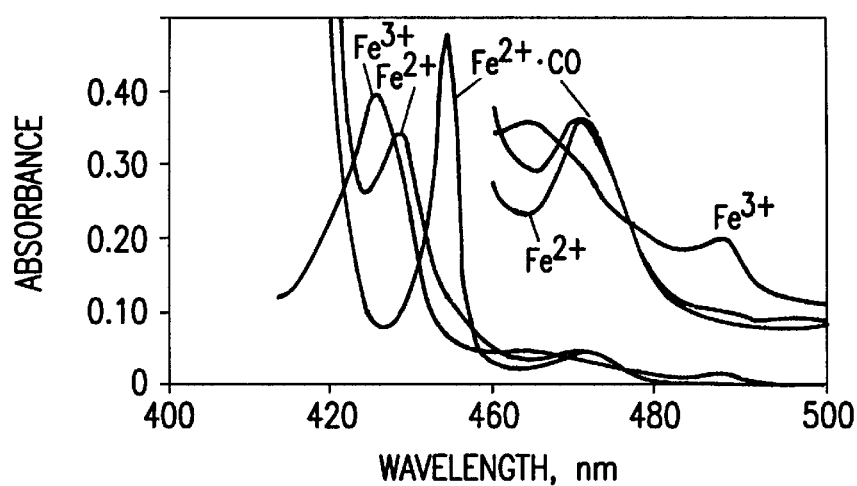
Figure 18C:
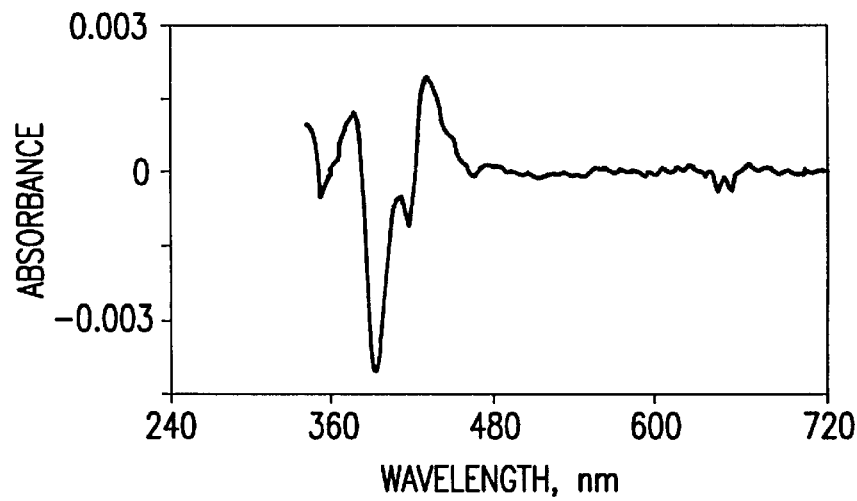

Spectra presented in FIG. 18B were used to obtain the extinction coefficients presented in Table V, which are based upon $\Delta\epsilon_{450-490}$ =91 mM$^{-1}$ cm$^{-1}$ for the Fe$^{2+}$.CO vs Fe$^{2+}$ difference spectrum (Omura and Sato, 1964, Omura and Sato *Methods Enzymol.* 10:556–561, 1967).

Figure 19:
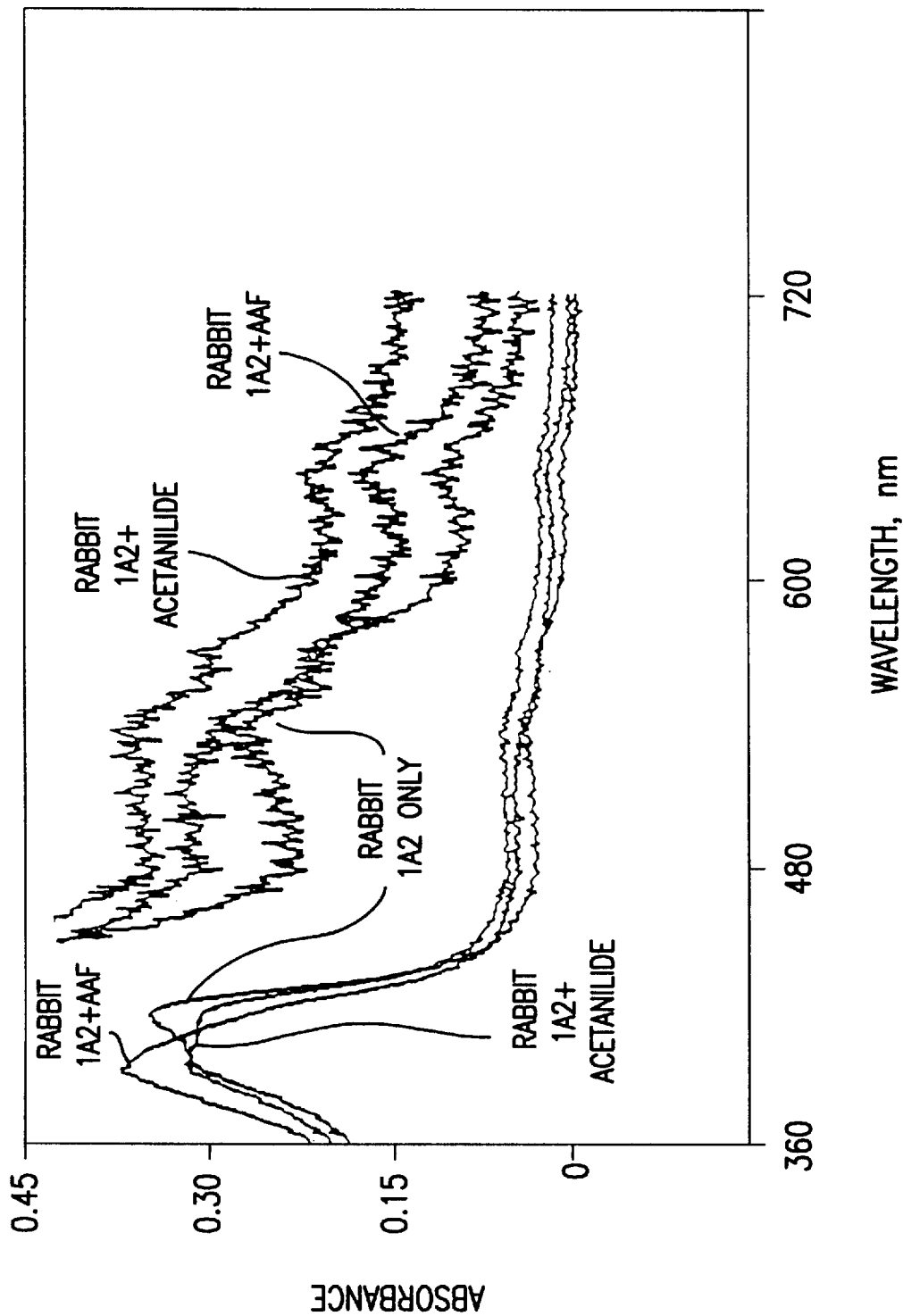
FIG. 19. Spectra of (ferric) rabbit P450 1A2. Absolute spectra of rabbit P450 [3.4 μM, in 0.20M potassium phosphate buffer (pH 7.4) containing 1.0 mM EDTA and 20% glycerol (v/v)] with 1.0 mM acetanilide or 0.10 mM AAF as indicated.
Figure 20A:
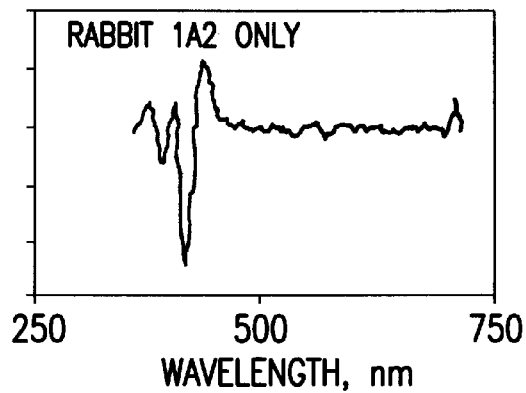
FIG. 20. Second derivative spectra of spectra presented in part A, plus that derived from a sample containing 0.10 mM αNF (the large positive band at the lower wavelength is due to αNF absorbance).
Figure 20B:
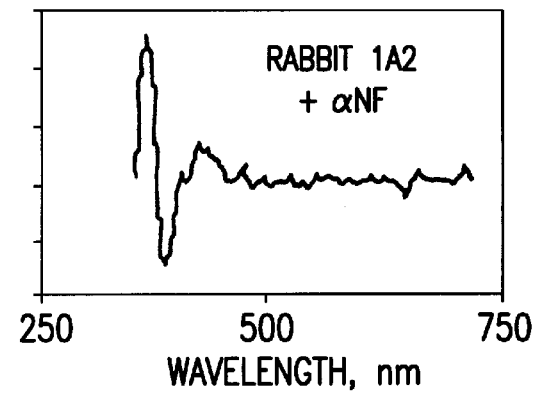
Figure 20C:
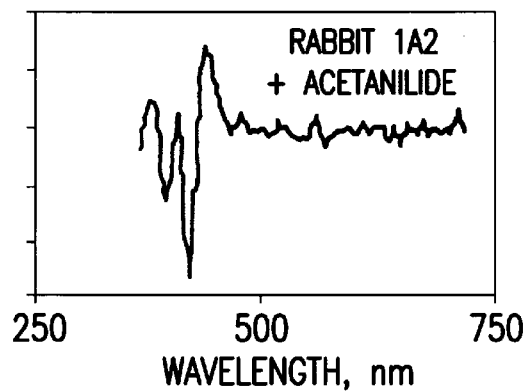
Figure 20D:
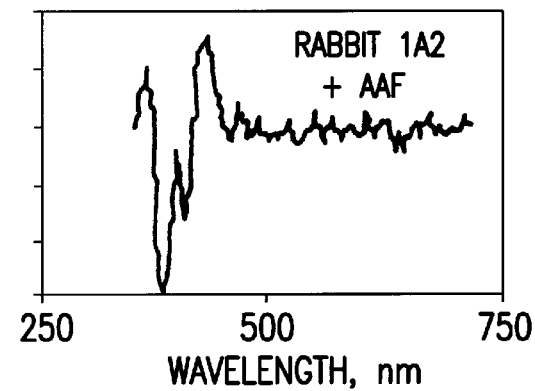

Although the literature tends to suggest that the various P450 1A2 enzymes of different animal species are high spin proteins (Ryan and Levin *J. Biol. Chem.* 255:7941–7955, 1980, Ryan and Levin *Pharmacol. Ther.* 45:153–239, 1990, Hashimoto-Yutsudo et al. *J. Biochem.* 88:505–516, 1980), this is clearly not the case. For instance, rat P450 1A2 ("P450$\beta_{NF/LSF-G}$") as isolated was ~⅔ high spin and shifted to the low spin form on addition of several typical P450 substrates or alcohols (Guengerich, 1983). The spin state of rabbit P450 1A2 is also known to be sensitive to perturbation (Haugen and Coon, 1976). To dramatize this effect, we isolated rabbit P450 1A2 (from liver microsomes of 5,6-benzoflavone-treated rabbits) by the same method used here for recombinant human P450 1A2 and examined its spectral properties (FIGS. 19, 20). The isolated protein was predominantly low spin, as indicated by the Soret band (and second derivative analysis) and the α, β bands. The iron was shifted towards the high spin state on addition of the substrates acetanilide or AAF and particularly by αNF.

The aerobic reduction of recombinant human P450 1A2 by Na$_2$S$_2$O$_4$[in the presence of CO with crystalline Na$_2$S$_2$O$_4$, in the usual manner (Omura and Sato, 1964, Guengerich, 1989)] is quite slow, in comparison to our experience with other purified and recombinant P450s including rat and rabbit P450s 1A2. For instance, it is not unusual for complete reduction to take 20–30 min even with a large excess of Na$_2$S$_2$O$_4$. The slow reduction was observed whether or not any of several detergents, buffers, or glycerol were present.

Figure 21A:
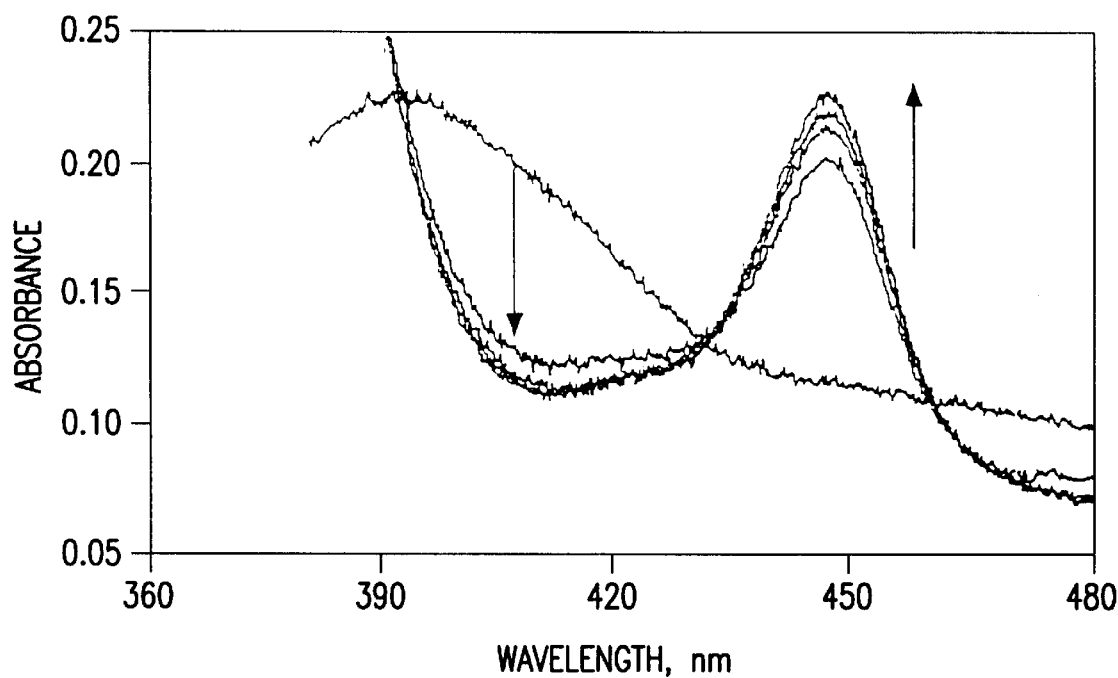
FIGS. 21, 22. An aerobic reduction of purified recombinant human P450 1A2. In both experiments (A,B) the mixture (3.0 ml) included 1.7 μM P450 1A2, 45 μM L-α-1,2-dilauoryl-sn-glycero-3-phosphocholine, and 0.10 M potassium phosphate buffer (pH 7.7) in a cuvette adapted for anaerobic use. The general conditions for removal of oxygen and anaerobic work are described elsewhere (Guengerich, 1983, Brian et al. *Biochemistry* 29:11280–11289, 1990), with the CO atmosphere percolated through three towers of alkaline $Na_2S_2O_4$ anthraquinone-2-sulfonate (Fieser and Fieser *Reagents for Organic Synthesis*, John Wiley and Sons, New York, p. 393, 1967) and the use of a glucose/glucose oxidase/catalase scavenging system (Guengerich, 1983, Brian, 1990). In Part A the system included 2.2 μM rabbit NADPH-P450 reductase. The oxidized spectrum ($l_{max}$ 390 nm) was recorded (Cary 14/OLIS system) and the reaction was initiated (23° C.) by the anaerobic addition of a pre-mixed NADPH generating system (Guengerich, 1989). Spectra were recorded at times (for the 447 nm peak) of 0.50, 5, 10, and 15 min. Arrows show the direction of change. In Part B no reductase was included and the reaction was initiated by the (anaerobic) addition of 28 mM $Na_2S_2O_4$. Spectra were recorded and the direction of change is shown with the arrows. The 447 nm data points were used to derive the semi-logathimic plot shown in Part C. The last data point (t=195 min) is not shown and was used as the endpoint. The $t_{1/2}$=38 min and k=0.018 $min^{-1}$.
Figure 21B:
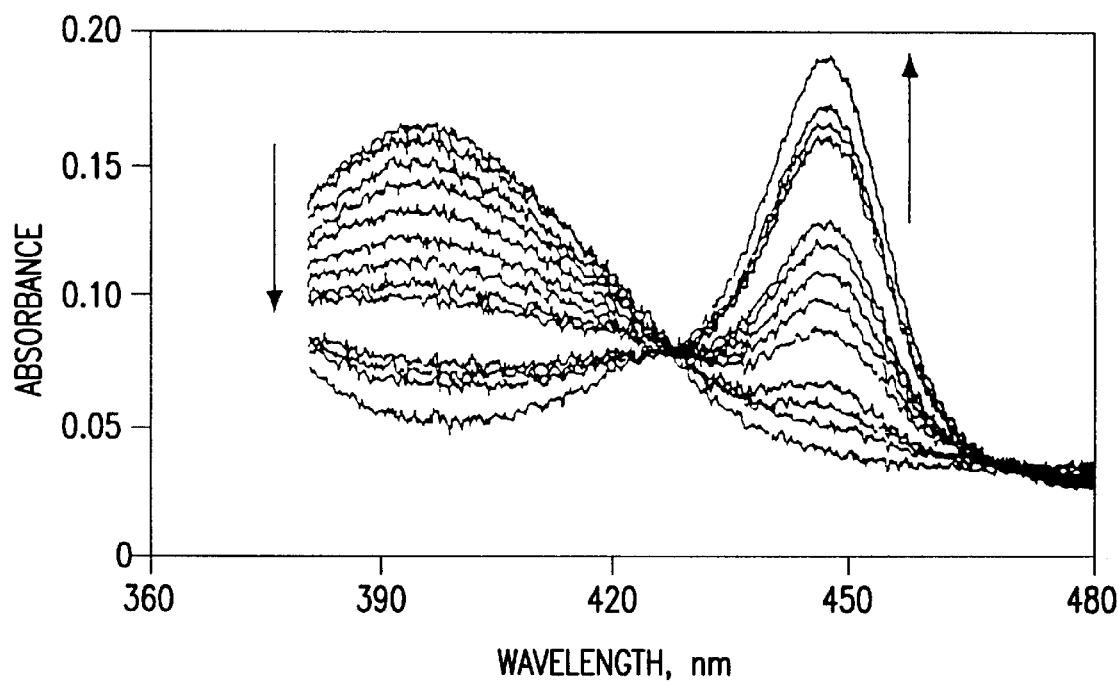

Reduction was reasonably fast when electrons were transferred from NADPH-P450 reductase in an anaerobic experiment (FIG. 21). Even under anaerobic conditions, Na$_2$S$_2$O$_4$ reduction was very slow. The pseudo first-order rate of reduction was 0.018 min$^{-1}$ at 23° C. in the presence of 28 mM Na$_2$S$_2$O$_4$ (FIGS. 7B,7C). For comparison, the rate of reduction by the reductase was >3 min$^{-1}$ (even at 23° C.), which is sufficient to support catalytic activities (vide infra). The reason for the slow rate of Na$_2$S$_2$O$_4$ reduction is unknown but the phenomenon seems unrelated to normal catalysis. Although modification of the N-terminus of the protein (vide infra) would not be expected to alter rates of Na$_2$S$_2$O$_4$ reduction, a strict comparison with the native protein has not been possible because of the difficulty in isolating large amounts of the enzyme from human liver (Distlerath et al., 1985, Butler et al, 1989).

N-Terminal sequence analysis of recombinant human P450 1A2. In an initial experiment, the proteins present in *E. coli* membranes were resolved by NaDodSO$_4$-polyacrylamide gel electrophoresis and transferred to a sheet of blotting paper. The major band corresponding to human P450 1A2 was cut out (~80 pmol) and submitted for N-terminal sequence analysis. No residues were recovered. The process was repeated after purification of P450 1A2 as described above (~60 pmol P450). Neither the major band nor the lighter band with slightly higher M$_r$ (FIG. 17) yielded any detectable amino acid residues. We conclude that the N-terminus is blocked, since the instrument used for sequence analysis has routinely been generating excellent results with <10 pmol of protein (including other P450s) (Shimada et al., 1992, Yun et al., 1992). We have also found this result previously whenever the N-terminal sequence MALLAVF (SEQ ID NO: 6)L . . . is attached to a P450 expressed in *E. coli* (using the pCW vector) (Gillam et al., 1993, Sandhu et al., 1993). When other N-terminal sequences are used this is not the case (Sandhu et al., 1993). The characterization of this apparent modification is the subject of current research.

Catalytic activities of modified human P450 1A2 expressed in *E. coli*. The P450 1A2 (1024) protein expressed in *E. coli* was purified and examined for catalytic activity in a reconstituted system containing rabbit NADPH-P450 reductase and L-α-1,2-dilauroyl-sn-glycero-3-phosphocholine. Comparisons were made with a human liver microsomal preparation known to be high in levels of P450 1A2 (sample HL 101) and the *E. coli* membrane preparation (Table VI).

Purified P450 1A2 (construct 1024) showed phenacetin O-deethylation activity similar to that of human liver microsomes whereas the 7-ethoxyresorufin O-deethylase activity was ~5 times greater than that of microsomes, expressed on a nmol P450 basis. However, it is of interest to note that *E. coli* membranes expressing P450 1A2 (1024) had only very low O-deethylation activities with either substrate (Table VI). Similar results have been obtained when these preparations were examined for catalytic activities towards carcinogenic arylamines (Hammons, G. J., Sandhu, P., Guo, Z., Kadlubar, F. F., and Guengerich, F. P., unpublished results). Also of interest is the observation that increasing NADPH-P450 reductase ratios did not enhance 7-ethoxyresorufin O-deethylation activity but increased phenacetin O-deethylation activity. The activity was optimal at a ratio of NADPH-P450 reductase:P450 1A2 of ~5:1.

Some purified P450 enzymes are highly dependent upon cytochrome b$_5$ (Gillam et al., 1993). In other experiments it was found that the addition of a 3-fold molar excess of human cytochrome b$_5$ did not significantly enhance the phenacetin or 7-ethoxyresorufin O-deeethylation activity of purified recombinant P450 1A2 (when the NADPH-P450 reductase:P450 1A2 ratio was 5:1). It is possible that other conditions of reconstitution may further enhance catalytic activity, but different ratios of the three enzymes under consideration here and other phospholipids have not been examined.

Conclusions. Constructs were prepared with different modifications of the 5' terminal of the human P450 1A2 cDNA and examined for expression in the pCW vector. Of those constructs considered (including the native sequence) only construct 1024, previously described by Fisher et al. (Fisher et al., 1992b) was expressed at a high level. It would appear that the potential energy for mRNA secondary structure formation is not the only predictor of expression efficiency. Minor changes in the N-terminal (5') sequence may have marked influences upon expression levels (FIG. 14, Table I), even when reasonable alignment choices have been made. Nevertheless, this particular construct (1024) is expressed at a higher level than most other eukaryotic P450s in bacteria (Larson et al, 1991b, Li and Chiang, 1991, Barnes et al., 1991, Fisher et al., 1992a, Fisher et al., 1992b, Gillam et al., 1993, Sandhu et al., 1993).

Although this particular modified form of human P450 1A2 is expressed at a high level and appears to be the major protein recovered in membranes, we encountered particular difficulty in purifying active enzyme because of instability in the presence of detergents (FIG. 16, Table II), a problem apparent in previous work by others (Fisher et al., 1992b). However, the inhibitor αNF was very effective in stabilizing the protein (FIG. 16, Table III). This stabilization allowed us to purify the protein in good yield (FIG. 17, Table IV). Remarkably, the purified protein was stable in the presence of detergents. The purified enzyme was catalytically active in the O-deethylation of 7-ethoxyresorufin and phenacetin (Table VI). However, the enzyme appeared not to be very active in bacterial membranes under the conditions used here. It is possible that the membrane structure inhibits access of NADPH-P450 reductase to P450 1A2. Alternatively, an inhibitor might be present in the membranes and conceivably even be related to the instability of this P450 in the presence of detergents.

Figure 22:
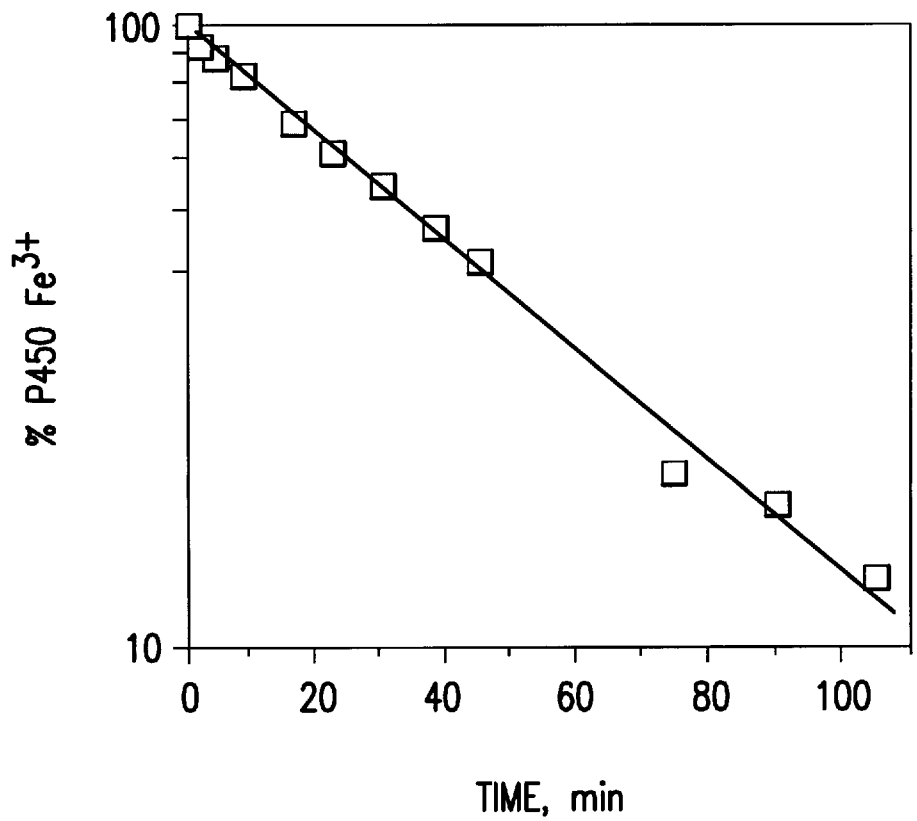

The absolute spectrum of purified P450 1A2 indicated that the iron was almost completely in the high spin configuration (FIG. 18, Table V), much more so than rabbit P450 1A2 isolated from liver microsomes by a similar procedure (FIGS. 19, 20). The slow rate of $Na_2S_2O_4$ reduction was surprising. Rates of reduction of P450 1A2 by NADPH-P450 reductase are considerably faster (FIGS. 21, 22).

The nature of the minor, upper $M_r$ band in the purified protein (FIG. 17) is not yet accounted for. The apparent reaction with immunoadsorbed rabbit anti-human P450 1A2 suggests that it is a slightly modified form of the P450 1A2 construct expressed in the bacteria. However, both the high and low $M_r$ polypeptides were apparently blocked when Edman degradation was attempted. It is our current view that the sequence MALLLAVFL (SEQ ID NO:6) signals a blocking post-translational modification in this system.

Finally, the point can be made that the high levels of expression seen with this particular P450 construct and the ease of purification may recommend it for future biophysical studies. Further modification of the sequence may increase its usefulness in this regard. The approach taken here may be useful in the preparation of large amounts of antibodies for use as reagents, which are not generally available at the current time. As judged by this and other studies (Fisher et al., 1992b), the purified enzyme seems to retain its intrinsic catalytic properties and should be of use in further examination of its activities towards drugs, steroids, and carcinogens.

TABLE I

Calculated potential free energy for RNA secondary structure formation (base region −26 to +21 with respect to the start codon) and P450 1A2 yields in E. coli membranes

| Construct | Secondary structure formation potential $\Delta G^\cdot (kcal\ mol^{-1})^b$ | Approximate expression yield, nmol P450 (liter culture)$^{-1}$ |
|---|---|---|
| 1023 (native) | −5.5 | <2 |
| 963 (not aligned to bovine P450 17A but containing the sequence MALLLAVF) (from SEQ ID NO: 6) | 4.8 to −5.0 | <2 |
| 964 (minus residues 3–22, original residues 1–2 and 23–28 modified to contain MALLLAVF sequence of bovine P450 17A) | −4.8 to −5.0 | <2 |
| 1024 (aligned to bovine P450 17A and containing the sequence MALLLAVFL) | −4.8 to −5.0 | 245 |
| 1025 (minus residues 3–28, codons 29–34 optimized for usage) | −5.9 | 4 |
| 1025 (minus residues 3–28, no alteration of codons 29–34) | −6.0 | <2 |

[a]See FIG. 14.
[b](44–46)

TABLE II

Effects of detergents on stability of recombinant P450 1A2 in E. coli membranes[a]

| Percentage | P450 | P420 |
|---|---|---|
| Minus EDTA Detergent (1.0%, w/v): | | |
| None | 91 | 9 |
| Sodium cholate | 23 | 77 |
| Emulgen 911 | 37 | 63 |
| Lubrol PX | 58 | 42 |
| Tergitol NP-10 | 15 | 85 |
| Triton N-101 | 66 | 34 |
| Plus EDTA (1.0 mM) Detergent (1.0%, w/v): | | |
| None | 90 | 10 |
| Triton N-101 | 36 | 64 |
| Sodium cholate | 76 | 24 |
| Sodium cholate + Triton N-101 | 13 | 87 |
| Octylglucoside | 4 | 96 |
| Emulgen 911 | 38 | 62 |
| Triton N-101, plus 1.0 mM EDTA: | | |
| 0.10% (w/v) | 78 | 22 |
| 0.20% | 55 | 45 |
| 0.40% | 41 | 59 |
| 0.50% | 34 | 66 |

[a]The buffer was 0.10 M potassium phosphate (pH 7.4) containing 20% glycerol (v/v).

TABLE III

| | Recovery (P450 + P420) in supernatant (%) | Percentage P450 | P420 |
|---|---|---|---|
| 0.50% Sodium cholate + 1.0 mM EDTA: | | | |
| without other detergents | 10 | 55 | 45 |
| +0.05% Triton N-101 | 20 | 66 | 34 |
| +1% Triton N-101 | 95 | 5 | 95 |
| 0.50% Sodium cholate + 1.0 mM EDTA + 10 μM αNF: | | | |
| +0.10% Triton N-101 | 31 | 88 | 12 |
| +0.10% Triton X-100 | 18 | 67 | 33 |
| +0.10% Brij 35 | 10 | 13 | 87 |
| +0.10% Tergitol NP-10 | 27 | 90 | 10 |
| 0.5% Sodium cholate + 1.0 mM EDTA + μM αNF: | | | |
| without other detergents | 19 | >95 | <5 |
| +0.50% Triton N-101 | 49 | >98 | <2 |
| +1.0% Triton N-101 | 90 | >95 | <5 |
| +0.50% Tergitol NP-10 | 94 | >98 | <2 |
| +0.50% Tergitol NP-10 + 0.50% Triton N-101 | 93 | >98 | <2 |
| 0.625% Sodium cholate + 1.25% Triton N-101 + 1.0 mM EDTA: | | | |
| No additions | | 22 | 78 |
| Phenacetin (0.10 mM) | | 20 | 80 |
| 17β-Estradiol (0.10 mM) | | 16 | 84 |
| Caffeine (5.0 mM) | | 46 | 54 |
| AAF (0.10 mM) | | 20 | 80 |
| 2-Naphthylamine (0.10 mM) | | 22 | 78 |
| 4-Ammobiphenyl (0.10 mM) | | 26 | 74 |
| Acetanilide (0.10 mM) | | 15 | 85 |
| αNF (30 μM) | | >98 | <2 |

[a]The buffer was 50 mM Tris-HCl (pH 7.4) containing 20% glycerol (v/v).

TABLE IV

Purification of P450 1A2 from *E. coli* membrane fraction

| Purification Step | Protein (mg)[a] | P450 (nmol) | Specific Content (nmol/mg protein)[a] | Yield (%) |
|---|---|---|---|---|
| Solubilized membranes | 1100 | 640 | 0.58 | 100 |
| DEAE void | 288 | 590 | 2.1 | 93 |
| CM: 300 mM phosphate | 40 | 320 | 7.8 | 50 |
| CM: 500 mM phosphate | 15 | 230 | 16 | 36 |

These values should be considered nominal.

TABLE V

Spectral characteristics of purified recombinant human P450 1A2[a]

| Form of P450 1A2 | Wavelength maximum, nm[b] | $\epsilon$, mM$^{-1}$, cm$^{-1}$ |
|---|---|---|
| $Fe^{3+}$ | 394 | 103 |
|  | 506 | 13.3 |
|  | 646 | 5.4 |
| $Fe^{2+}$ | 410 | 84 |
|  | 544 | 13.6 |
| $Fe^{2+} \cdot CO$ | 446 | 125 |
|  | 548 | 13.7 |
| $Fe^{2+} \cdot CO$ vs $Fe^{2+}$ (difference) | 446 | 91.0[c] |

[a]All spectra were recorded in 0.10 M potassium phosphate buffer (pH 7.4) containing 1.0 mM EDTA and 20% glycerol (v/v).
[b]Determined using the peak finder program of the Aminco DW2/OLIS system.
[c]Assumed in making calculations (2 Omura and Sato, 1964 and Omura and Sato, 1967).

TABLE VI

Catalytic activities of recombinant human P450 1A2 expressed in *E. coli* and in human liver microsomes

| Enzyme preparation | Ratio NADPH-reductase: P450 | 7-Ethoxyresorufin O-deethylation | Phenacetin O-deethylation |
|---|---|---|---|
| Liver microsomes (sample HL101) |  | 0.12 | 1.75 |
| *E. coli* membranes (1024)[b] | 1:1 | 0.02 | 0.02 |
|  | 2:1 | 0.03 | 0.02 |
|  | 5:1 | 0.02 | 0.03 |
|  | 10:1 | 0.02 | 0.03 |
| Purified recombinant P450 1A2[b] | 1:1 | 0.62 | 0.78 |
|  | 2:1 | 0.61 | 1.38 |
|  | 5:1 | 0.71 | 2.07 |
|  | 10:1 | 0.72 | 1.97 |

[a]Results are presented as means of duplicate experiments.
[b]L-α-1,2-Dilauroyl-sn-glycero-3-phosphocholine (30 μM) was included in the incubations.

EXAMPLE 4

Expression of Modified Human Cytochrome P450 2E1 in *Escherichia coli*, Purification, and Spectral and Catalytic Properties

Methods and Materials

Figure 23:
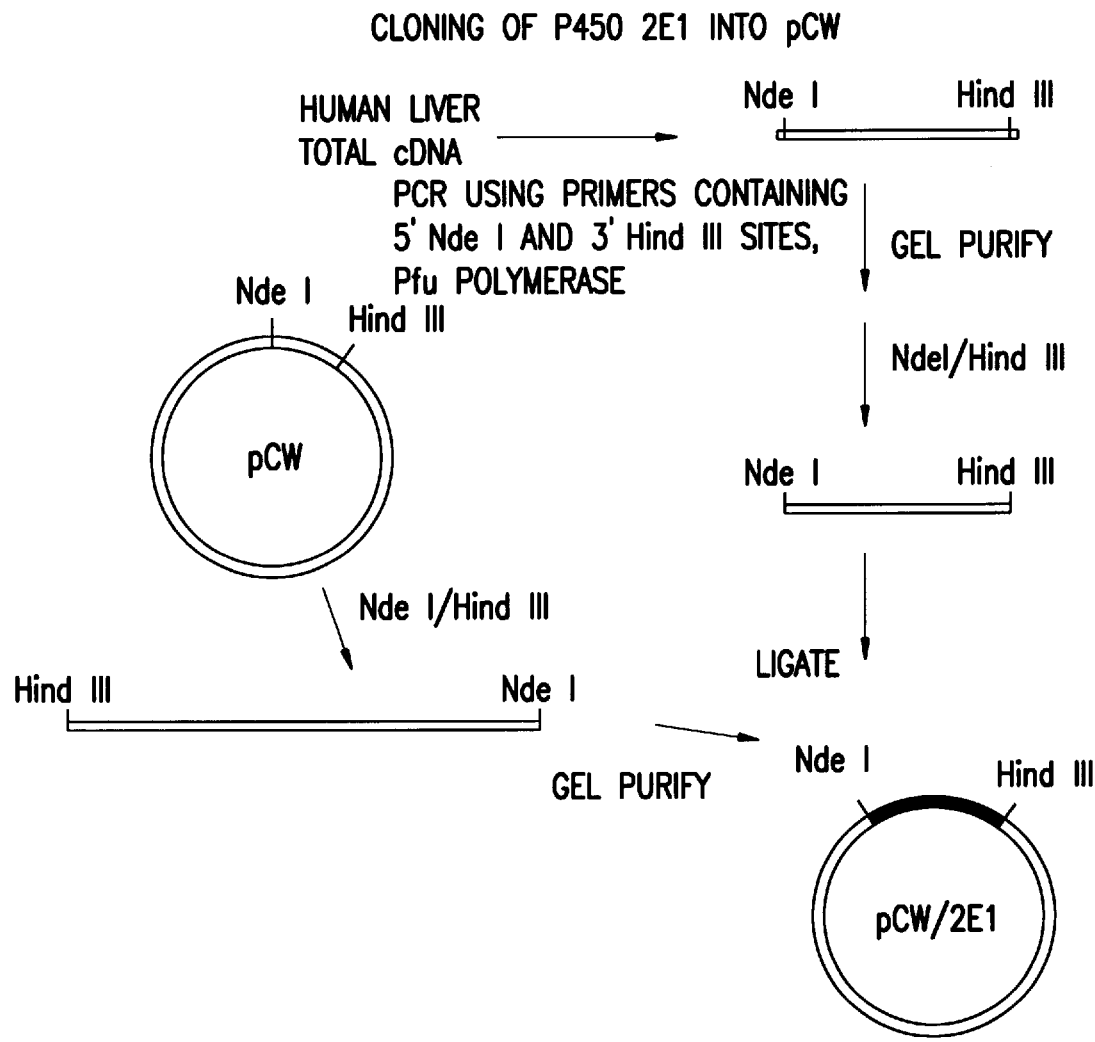
FIG. 23. General strategy for preparation of human P450 2E1 cDNA and construction of modified pCW vectors.

Cloning of human P450 2E1 cDNA. Total hepatic RNA from a single human liver sample (code HL 34) was extracted by the method of Chomczynski and Sacchi (Chomczynski and Sacchi, *Anal Biochem.* 162:156–159 (1987)) and subjected to oligo-dT cellulose chromatography to select polyA+ RNA as described elsewhere (Jacobson, *Methods Enzymol.* 152:254–261 (1987)). Double-stranded cDNA was generated by modifications of previous methods (D'Alessio and Gerard, *Nucl. Acids Res.* 16:1999–2014 (1988)). Briefly, first strand cDNA was reverse-transcribed by MMLV reverse transcriptase and then incubated with *E. coli* DNA polymerase I exonuclease Klenow fragment (U.S. Biochemical, Cleveland, Ohio) and *E. coli* DNA ligase (without added RNAse H). The resulting double-stranded total liver cDNA served as a template for the PCR amplification. The native P450 2E1 cDNA was specifically amplified with Pfu polymerase (Stratagene, LaJolla, Calif.) using conditions recommended by the manufacturer [20 mM Tris-HCl buffer (pH 8.8) containing 10 mM KCl, 6.0 mM $(NH_4)_2SO_4$, 2.0 mM $MgCl_2$, 0.10% Triton X-100 (v/v), 0.10 mg bovine serum albumin ml$^{-1}$, 0.20 mM each dNTP, 0.25 μM each primer, and 5 U Pfu polymerase ml$^{-1}$] and using an annealing temperature of 50° C. PCR primers aligned perfectly with the published human P450 2E1 cDNA sequence (Umeno et al., *Biochemistry* 27:9006–9013 (1988)) except for the inclusion of an Nde I site coincident with the start codon in the 5' primer (sequence: 5'CAGCGGCCATAT-GTCTGCCCTCGCA 3') (SEQ. ID. NO.: 36) and a Hin dIII site after the stop codon in the 3' primer (sequence: 5' ATCCTGAACTCAAACAATTTGAAAGCT-TGTTTGAAAAGCG 3') (SEQ. ID. NO.: 37). These modifications facilitated subsequent endonuclease digestion and ligation of the PCR product into the cognate sites of the expression vector pCW (FIG. 23).

N-terminal modifications. N-terminal mutations (FIG. 24) were introduced into the native construct (pCW/2E1#1) by PCR-based cassette mutagenesis. The N-terminal segment of 2E1 was amplified between the Nde I and Mro I sites using 5' PCR primers containing the desired mutations and a (100%) complementary 3' PCR primer (5' CATCCCAT-AGTTCCGGAGGGTGGTCAG 3') (SEQ. ID. NO.: 38) centered on the Mro I site. The mutagenic primers for constructs #11–#18 are listed in FIG. 24. Pfu polymerase was used for the PCR amplifications at an annealing temperature of 60° C.

Expression trials. Expression of each N-terminal variant of P450 2E1 in the pCW vector was assessed following the basic procedure described previously (Gillam et al., *Arch. Biochem. Biophys.* 305:123–131 (1993)). *E. coli* strain DH5α was transformed with each plasmid and selected on LB agar containing ampicillin. Single colonies were grown overnight in LBamp media at 37° C.; 1 ml of an overnight culture was then used to seed 100 ml of modified TB medium (Gillam et al., 1993). Protein expression was induced with 1.0 mM IPTG for 24–48 h at 28°–32° C. with vigorous shaking before cells were harvested and subcellular fractions prepared as described (Gillam et al., 1993). $Fe^{2+}$ .CO vs $Fe^{2+}$ difference spectra (Omura and Sato, *J. Biol. Chem.* 239:2370–2378 (1964)) were used to detect hemoprotein; apoprotein production was assayed by immunoblotting with a polyclonal antibody raised in rabbits to purified human P450 2E1 (Guengerich et al., *Chem. Res. Taxicol.* 4:168–179 (1991)). Expression levels were examined using cultures grown in 0, 5, or 50 μM 4MP to determine if this compound stabilized the recombinant P450 against degradation.

Large scale cultures of construct 2E1#18 were routinely done by inoculating 1.0 liter of TB media with 10 ml of the overnight LBamp culture. The TB media was supplemented with 0.2% bacto-peptone (w/v), ampicillin, thiamine, and trace elements as described previously (Gillam et al., 1993; Sandhu et al., *Arch. Biochem. Biophys.*, in press (1994); Sandhu et al., *Arch. Biochem. Biophys.*, in press (1994)). Induction of the tac promoters was initiated by the addition of 1.0 mM IPTG and allowed to proceed for 48 h at 30° C. with virorous shaking in a New Brunswick Innova 4300 shaker (New Brunswick Scientific, Edison, N.J.). Subsequent membrane preparation was carried out essentially as described elsewhere (Gillam et al., 1993; Sandhu et al., 1993; Sandhu et al., 1994).

Purification of recombinant P450 2E1. *E. coli* membrane fractions were diluted to a protein concentration of 2 mg ml$^{-1}$ in 50 mM Tris-HCl buffer (pH 7.4) containing 20% glycerol (v/v), 0.625% sodium cholate (w/v), 1.25% Triton N-101 (v/v), 1.0 mM EDTA, and 1.0 mM DTT. 4MP was added (to 50 µM). The solubilized membrane preparations was stirred at 4° C. for 2 h and then centrifuged at $10^5$ g for 60 min (at 4° C.).

The resulting supernatant was loaded onto a 2.5×7 cm DEAE-Sephacel column (Pharmacia, Piscataway, N.J.) equilibrated with the membrane solublization buffer. The void volume fractions were pooled and diluted 2.5-fold with a solution of 20% glycerol (v/v), 0.20 mM EDTA, and 1.0 mM DTT. The diluted solution was applied to a 1.5×2 cm CM Sepharose Fast-Flow column (Pharmacia) that had been equilibrated with 20 mM potassium phosphate buffer (pH 7.4) containing 50 µM 4MP , 20% glycerol (v/v), 0.20 mM EDTA, and 1.0 mM DTT. The column was sequentially washed with 200 ml each of the CM-Sepharose equilibration buffer and 50 mM potassium phosphate buffer (pH 7.4) containing 20% glycerol (v/v), 0.20 mM EDTA, and 1.0 mM DTT. P450 2E1 was eluted with a linear gradient of 10 mM to 200 mM potassium phosphate (pH 7.4) (100 ml each) with 0.2% Triton N-101 (v/v), 50 µM 4MP , 20% glycerol (v/v), 0.20 mM EDTA, and 1.0 mM DTT present. The fractions that were nearly homogeneous as judged by NaDodSO$_4$-polyacrylamide gel electrophoresis (Laemmli, *Nature* 227:680–685 (1970)) and silver staining (Wray et al., *Anal. Biochem.* 118:197–203 (1981)) were pooled. Detergent and 4MP were removed by application to a small hydroxylapatite column (1×1 cm), extensive washing, and elution with 300 mM potassium phosphate buffer (pH 7.4) containing 20% glycerol (v/v), 0.20 mM EDTA, and 1.0 mM DTT.

Other proteins. NADPH-P450 reductase was purified to electrophoretic homogeneity from liver microsomes prepared from phenobarbital-treated rabbits using the procedure of Yasukochi and Masters (Yasukochi and Masters, *J. Biol. Chem.* 251:5337–5344 (1976)) as modified (Shimada et al., *J. Biol. Chem.* 261:909–921 (1986)). Cytochrome b$_5$ was purified from human liver sample HL 104 as described elsewhere (Gillam et al., 1993; Sandhu et al., 1993; Funae and Imaoka, *Biochim. Biophys. Acta* 842:119–132 (1985)). Rabbit anti-human P450 2E1 was raised as described (Guengerich et al., 1991) and was treated with *E. coli* membranes to adsorb some of the antibodies reacting with bacterial proteins.

Other assays and methods. P450 spectra were recorded either with a Varian/Cary 210 (Varian, Walnut Creek, Calif.) or an Aminco DW2/OLIS instrument (On-Line Instrument Systems, Bogart, Ga.) at ambient temperature using the general method of Omura and Sato (Omura and Sato, 1964). Wavelength maxima were determined with the Aminco/OLIS instrument (calibrated with holmium oxide) using either the peak finder or second derivative analysis software.

Chlorzoxazone 6-hydroxylation assays were done as described elsewhere (Peter et al., *Chem. Res. Toxicol.* 3:566–573 (1990)). The reaction volume was 0.50 ml and the incubation time was 15 min (at 37° C.). The P450 2E1, NADPH-P450 reductase, and L-α-1,2-dilauroyl-sn-glycero-3-phosphocholine concentrations were 50 nM, 150 nM, and 30 µM, respectively. The glycerol concentration was 0.1–0.2% in the final incubation mixture, which should not be inhibitory under these conditions where high concentrations of substrate were used (Yoo et al., *Cancer Res.* 47:3378–3383 (1987)).

Protein concentrations were estimated using a bicinchoninic acid BCA) method according to the instruction supplied by the manufacturer (Pierce Chemical Co., Rockford, Ill.).

NaDodSO$_4$-polyacrylamide gel electrophoresis was done as described by Laemmli (Laemmli, 1970) using an acrylamide concentration of 7.5% (w/v). Gels were stained with ammonical silver according to Wray et al. (Wray et al., 1981). Immunoblotting was done using the general method described previously (Guengerich et al., *Biochemistry* 21:1698–1706 (1982)).

N-Terminal amino acid sequence analysis was done in the Vanderbilt facility using a modified Applied Biosystems 470A instrument (Applied Biosystems, Foster City, Calif.). The procedures used for NaDodSO$_4$-polyacrylamide gel electrophoresis, transfer to Immobilon membranes (Waters-Millipore, Bedford, Mass.), and staining are described elsewhere (Matsudaira, *J. Biol. Chem.* 262:10035–10038 (1987); LeGendre and Matsudaira, *BioTechniques* 6:154–159 (1988)). Yields at each cycle were estimated by comparison with external standards.

Results

P450 2E1 Cloning. The PCR product obtained after amplification with high-fidelity Pfu polymerase was sequenced in its entirety. Three differences from the published P450 2E1 cDNA sequence were noted in the coding sequence. These were as follow (numbering from the start codon): G to C at position 18; T to C at 105; C to A at 1313. A single deletion of T at position 1514 in the 3' untranslated region was also observed.

The first two coding region substitutions would not affect the amino acid sequence, but the last would result in an Ala to Asp change in the codon immediately following the Cys involved in heme binding. Therefore it was of interest to determine whether this point mutation arose as a PCR error or was present in the template cDNA. Accordingly, an allele-specific PCR technique was developed to discriminate between the published sequence and our product at position 1313 (details not presented). When this assay was performed on the original cDNA from which the 'mutant' clone was originally obtained, amplification was only seen for the normal allele- and not with the mutant allele-specific primers (results not shown). Therefore, this base pair substitution was attributed to an error in the original PCR amplification, emphasizing the necessity of verifying sequence of PCR products even when higher fidelity polymerases are used. Since the other sequence differences were not investigated, it is not clear whether these represent allelic variants or other Pfu-derived errors.

The sequence at position 1313 was repaired by a PCR-based cassette style mutagenesis using one primer encoding the correct sequence and including the Stu I site at 1320 and the other including the unique Eae I site at position 898. The sequence of the resulting product was verified after cloning into the appropriate segment of the native P450 2E1 cDNA. The repaired cDNA was used as the template for all further work.

Expression of N-terminal variants: A variety of N-terminal mutations were introduced into the P450 2E1 native sequence according to different strategies which had proven successful for expressing other P450s in bacteria.

Constructs #2E1 11, 16, and 18 contained truncated hydrophobic amino acid sequences (Larson et al., *J. Biol. Chem.* 266:7321–7324 (1991a); Larson et al., *Proc. Natl. Acad. Sci. USA* 88:9141–9145 (1991b)), construct #14 had the bovine P450 17A sequence aligned optimally, constructs #14, 17, and 18 had the Ala codon GCT in the second position, and constructs #14–18 all contained 5'-terminal codons optimized for AT content and minimizing the potential for secondary structure formation of mRNA transcripts. All constructs were made with the P450 2E1 cDNA after repair mutagenesis at position 1313 (vide supra); no attempts were made to compare the effect of the Ala to Asp mutation at codon 438.

Figure 25:
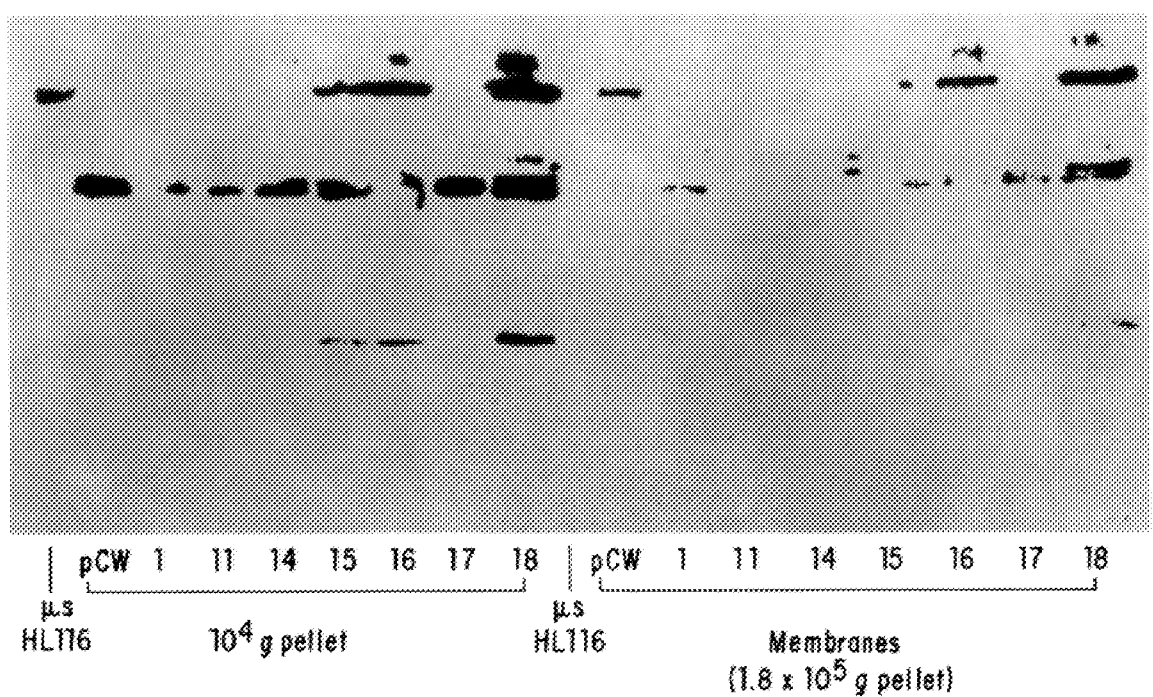
FIG. 25. Immunoblot analysis of human P450 2E1 expression in *E. coli* cells. In each case bacterial membrane protein from 20 mg wet mass of cells was used for $NaDodSO_4$-polyacrylamide gel electrophoresis and immunoblotting was done with rabbit anti-human P450 2E1. Microsomes from human liver sample HL 116 were included as noted (μS HL 116), and the position of hepatic P450 2E1 is indicated by arrows on both sides of the gel.

Immunoblots indicated significant apoprotein production in cultures expressing several constructs (FIG. 25). Most immunoreactivity was detected in the $10^4$ g pellet and membrane fractions, with little expression in the soluble fraction ($1.8 \times 10^5$ g supernatant) even in variants lacking the hydrophobic N-terminus (data not shown). Densitometric analysis indicated that expression levels were highest for the 2E1 #18 construct and also substantial for constructs #15 and 16 (Table I).

Figure 26:
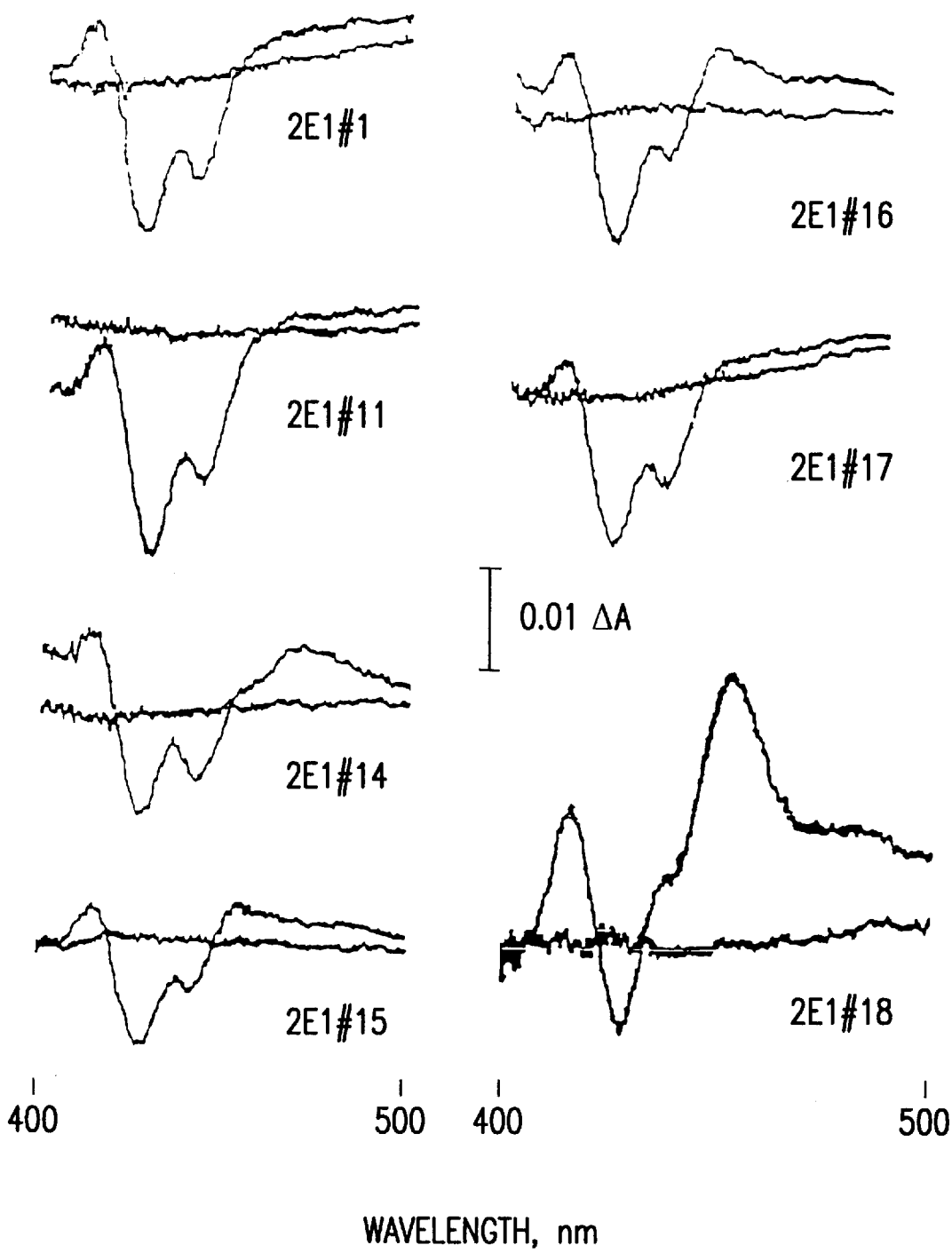
FIG. 26. $Fe^{2+}$.CO vs $Fe^{2+}$ difference spectra of *E. coli* membrane preparations derived from various P450 2E1 constructs. In all cases membranes were prepared and diluted to ~2 mg protein $ml^{-1}$ in 0.10M potassium phosphate buffer (pH 7.7) containing 1.0 mM EDTA, 20% glycerol (v/v), 0.50% sodium cholate (w/v), and 0.40% Emulgen 913 (v/v). Spectra were recorded using a Varian Cary 210 instrument. The $Fe^{3+}$ vs $Fe^{3+}$ baselines are shown in every case.

$Fe^{2+}$.CO spectra characteristic of endogenous *E. coli* hemoproteins has confounded observation of P450 spectra in crude bacterial fractions in other P450 2E1 expression systems (Porter and Larson, *Methods Enzymol.* 206:108–116 (1992)). In the current study, hemoprotein expression in membranes was sufficiently high for 2E1 constructs #15, #16, and #18 to overcome this interference. Spectra shown for 2E1 constructs #1, #11, and #17 are typical of those seen with bacterial membranes containing only endogenous bacterial hemoproteins (FIG. 26). Since 2E1 construct #18 showed the strongest P450 peak, it was selected for further purification and characterization.

Expression from the P450 2E1#18 construct was optimized with respect to time of induction (48 h) and temperature (30° C.). 4MP was added to cultures at either 5 or 50 $\mu$M but had no effect on expression yields and was omitted for routine studies. Although conditions for the expression of other constructs have not been examined in so great detail, it has been our general experience that the variation in conditions for optimal expression of different P450s is greater than for similar constructs of the same P450 (Gillam et al., 1991; Omura and Sato, 1964; Sandhu et al., 1994). Although we cannot categorically establish this point we did concentrate our efforts on the construct that appeared to be most efficient in initial trials (#18).

Figure 27:
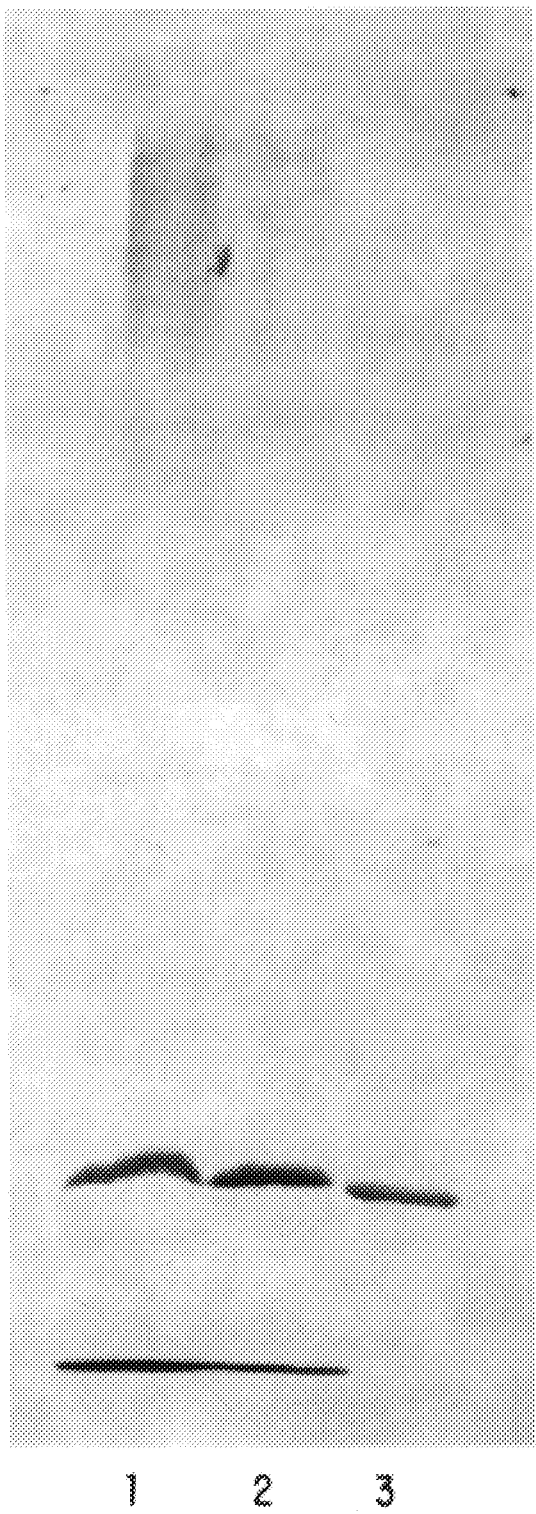
FIG. 27. Purification of recombinant P450 2E1 from *E. coli* membranes. $NaDodSO_4$-polyacrylamide gel electrophoretograms were stained with ammonical silver (Wray et al., 1981). Lane 1, membranes (42 μg protein); lane 2, DEAE-Sephacel void fraction (19 μg protein); lane 3, CM-Sepharose gradient fraction (0.76 μg protein) (nominal protein concentrations from bicinchoninic acid assay).

Purification of recombinant human P450 2E1. In the course of our work with recombinant human P450 1A2 (Sandhu et al., 1994) we found high concentrations of the detergents sodium cholate and Triton N-101 to be very useful in DEAE chromatography. Many *E. coli* membrane proteins appear to be bound to DEAE-Sephacel under these conditions and recombinant human P450 proteins are eluted in the void volume. This was also the case in the purification of recombinant human P450 2E1, with a high yield and considerable improvement after this step (FIG. 27). Some low $M_r$ proteins were still present (migrating at the dye front of the gel) and could be removed by adsorption of the material to a CM-Sepharose Fast-flow column and elution with a gradient of increasing phosphate concentration (FIG. 27). The overall yield at this point was >80% and a relatively high nominal specific content of P450 (13 nmol/mg protein) was measured (Table II). Detergent was removed by dialysis, adsorption to a small column of hydroxylapatite, extensive washing with buffer, and elution with a high concentration of phosphate.

In the initial purifications done without 4MP the resulting P450 was contaminated with $\sim\frac{1}{3}$ cytochrome P420. Although we found the 4MP had no effect on the level of P450 produced in *E. coli* DH5α cells (vide supra) we did find that this ligand appeared to stabilize P450 during purification, as in the report of Larson et al. (Larson et al., 1991a). When 50 $\mu$M 4MP was included in the buffers used for purification, no cytochrome P420 was detected in the final product (vide infra). The 4MP was removed from the preparation along with detergent in the hydroxylapatite chromatography step.

Figure 28:
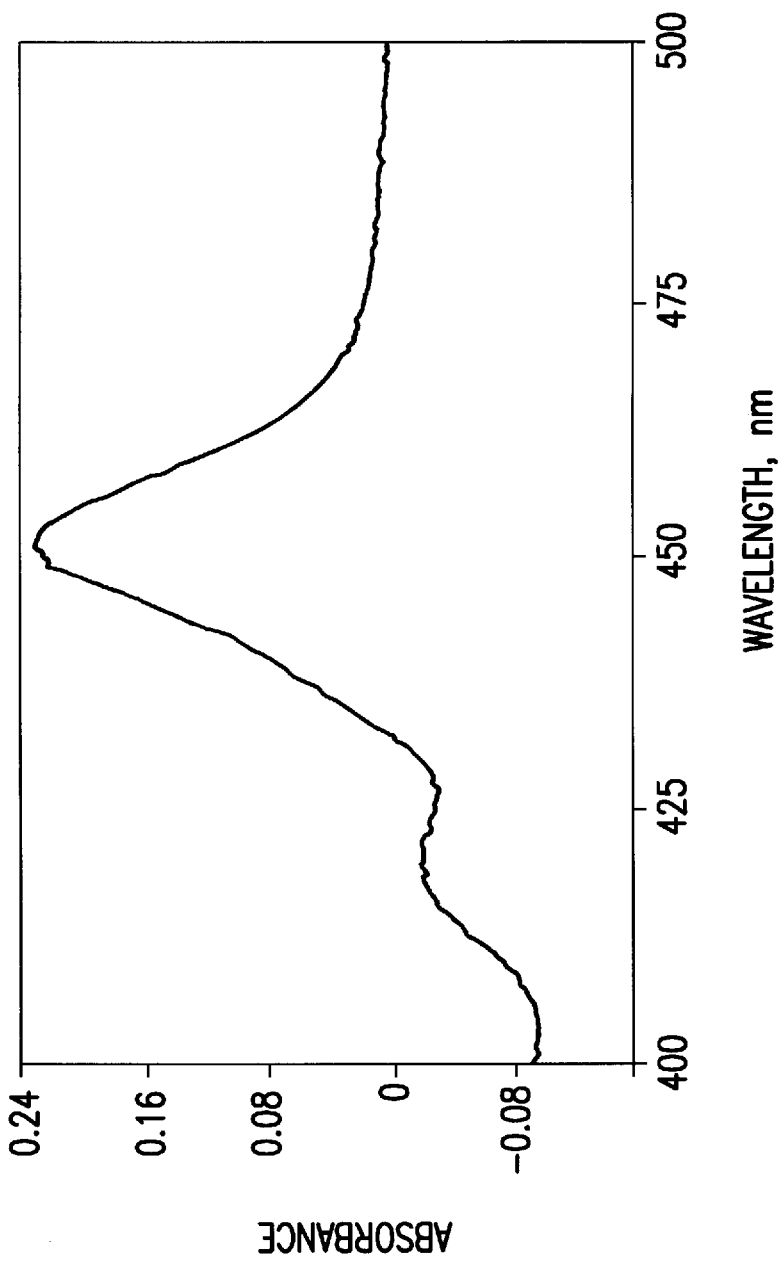
FIG. 28. $Fe^{2+}$.CO vs. $Fe^{2+}$ difference spectra of membranes prepared from various P450 2E1 (construct 2E1 #18) in *E. coli* cells. Cells (3rd in culture volume) were sedimented and suspened in 2.0 ml of 0.10 m potassium phosphate buffer (pH 7.7) containing 1.0 μM EDTA, 20% glycerol (v/v), 0.50% sodium cholate (w/v), and 0.40% Emulgne 913 (v/v). Spectra were recorded using an Aminco DW2/OLIS instrument.

Spectral properties. In contrast to recombinant human P450 1A2 (Sandhu et al., 1994), P450 2E1 was readily reduced by $Na_2S_2O_4$. (FIG. 28). Little cytochrome P420 appeared to be present in the cells, and the absorbance in the 420 nm region may be due to other hemoproteins. Yields as high as 160 nmol spectral P450 (liter culture)$^{-1}$ are now routinely detected in the cells; there is actually a substantial loss in large-scale harvesting of cells and membrane recovery.

Figure 29A:
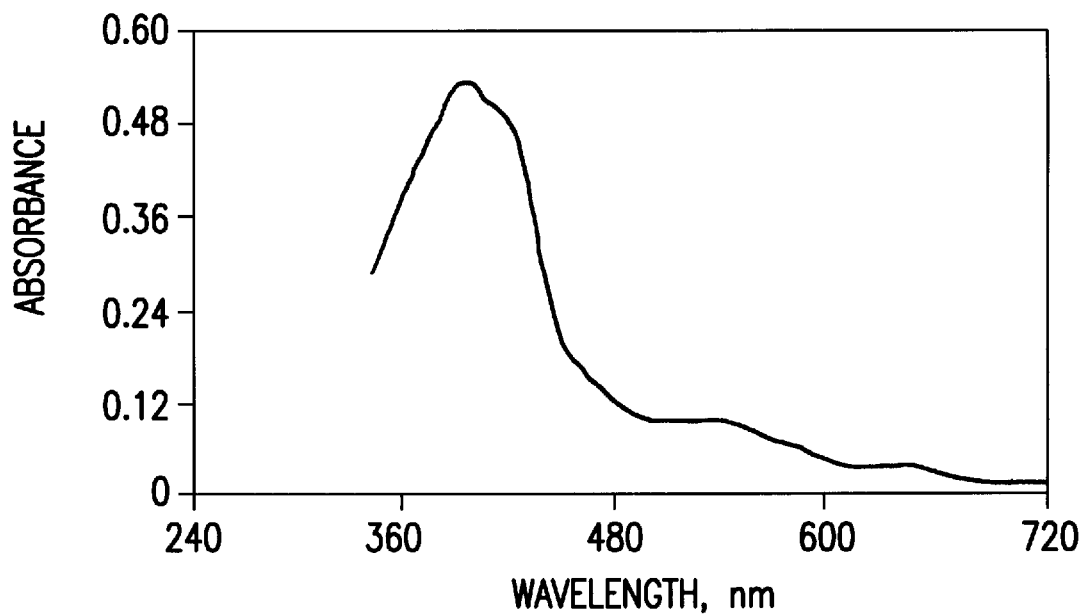
FIG. 29. Near UV-visible spectra of purified recombinant ferric P450 2E1. The spectrum was recorded with ~5 μM P450 2E1 in 0.15M potassium phosphate buffer (pH 7.4) containing 1.0 mM EDTA and 20% glycerol (v/v). All spectra were recorded with an Aminco DW2/OLIS instrument. (A) $Fe^{3+}$ spectrum. The inset shows the expanded α,β region. (B) Second derivative spectrum derived from Part A.
Figure 29B:
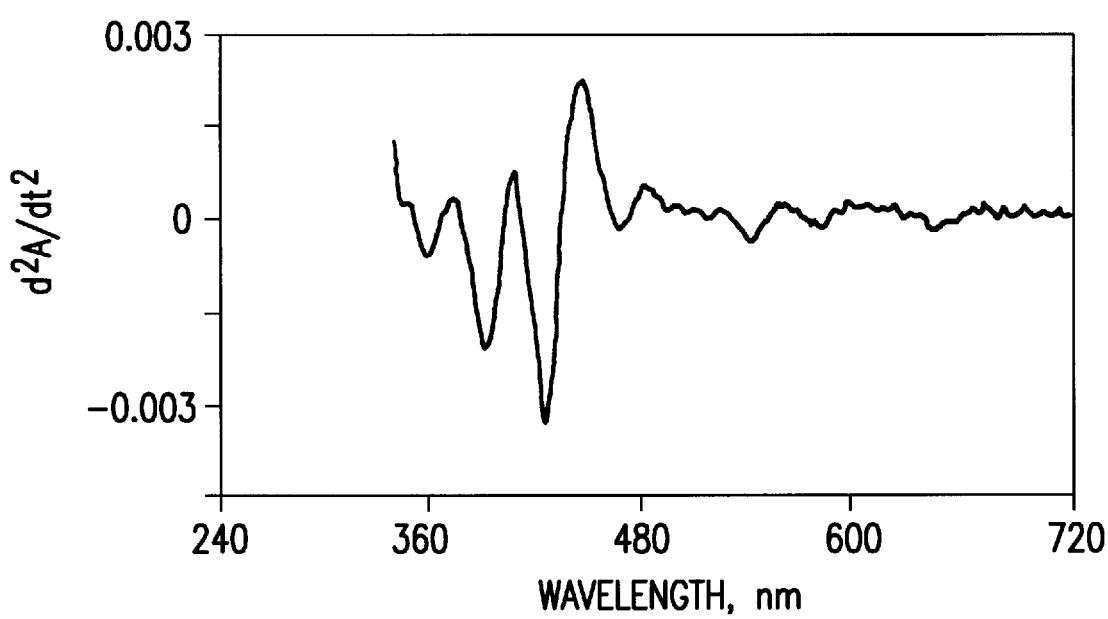

Purified P450 2E1 was isolated as a mixture of high- and low-spin ferric proteins (FIGS. 29A,B), as is the cases of hepatic rat and rabbit P450 2E1 (Koop et al., *J. Biol. Chem.* 257:8472–8480 (1982); Ryan et al., *J. Biol. Chem.* 260:6385–6393 (1985)). The bands at 393 and 640 nm and the coalesced α and β bands are diagnostic of the high-spin iron configuration in P450s (Imai et al., in Cytochrome P-450, Sato and Omura, Eds., 37–135, Academic Press, New York (1978)). Although the high-spin component might seem to predominate in the unmodified $Fe^{3+}$ spectrum (FIG. 29A), second-derivative analysis indicates that the low-spin component is more abundant (FIG. 29B).

Figure 30:
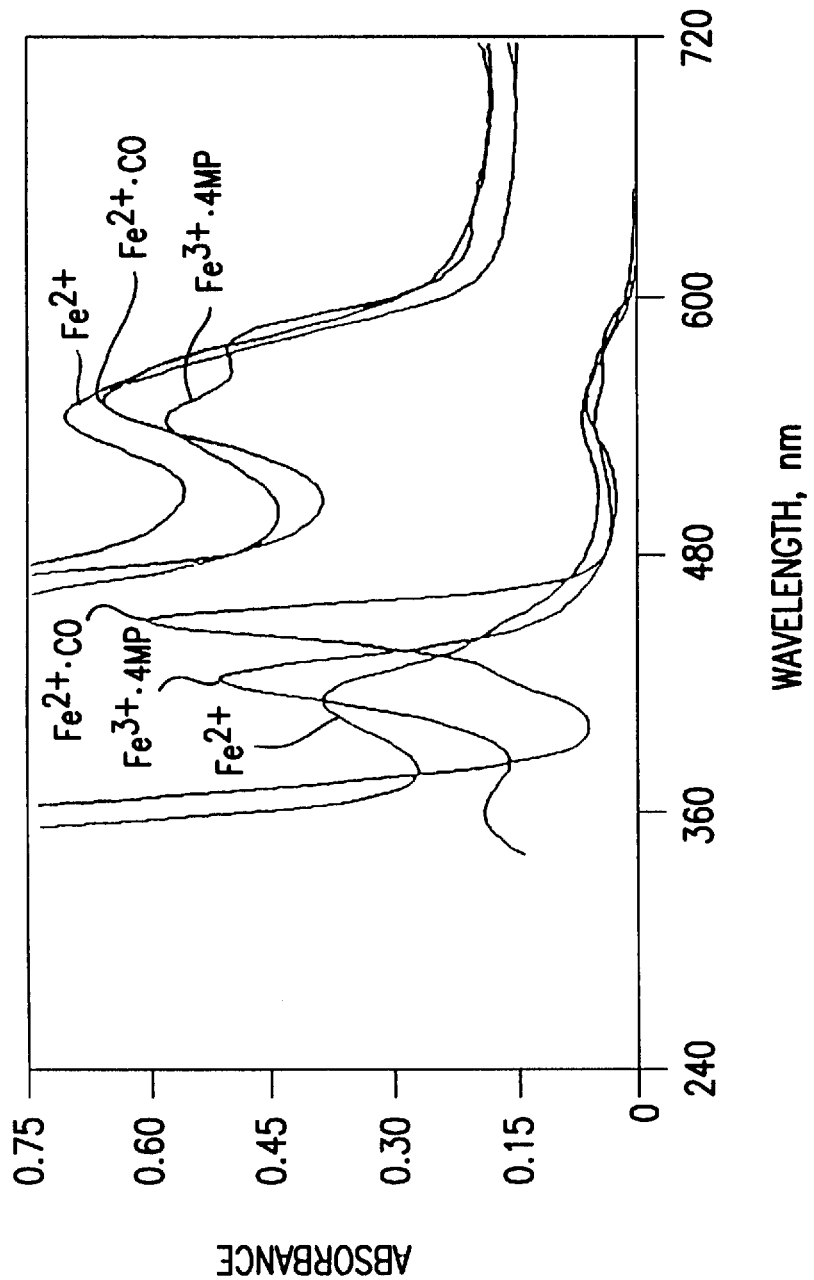
FIGS. 30, 31. Near UV-visible spectra of purified recombinant P450 2E1. All spectra were recorded with 5.0 μM P450 2E1 in 0.15M potassium phosphate buffer (pH 7.4) containing 1.0 mM EDTA and 20% glycerol (v/v). All spectra were recorded with an Aminco DW2/OLIS instrument. (A) The $Fe^{3+}$.4MP spectrum was measured in the presence of 30 μM 4MP. The $Fe^{2+}$ and $Fe^{2+}$.CO spectra obtained (in the absence of 4MP) with the addition of excess $Na_2S_2O_4$. The inset shows the expanded α,β region. (B) $Fe^{2+}$.CO vs $Fe^{2+}$ difference spectrum (different concentration than in Part A). The cross is at 450.0 nm for reference. For wavelength maxima and extinction coefficients see Table III.
Figure 31:
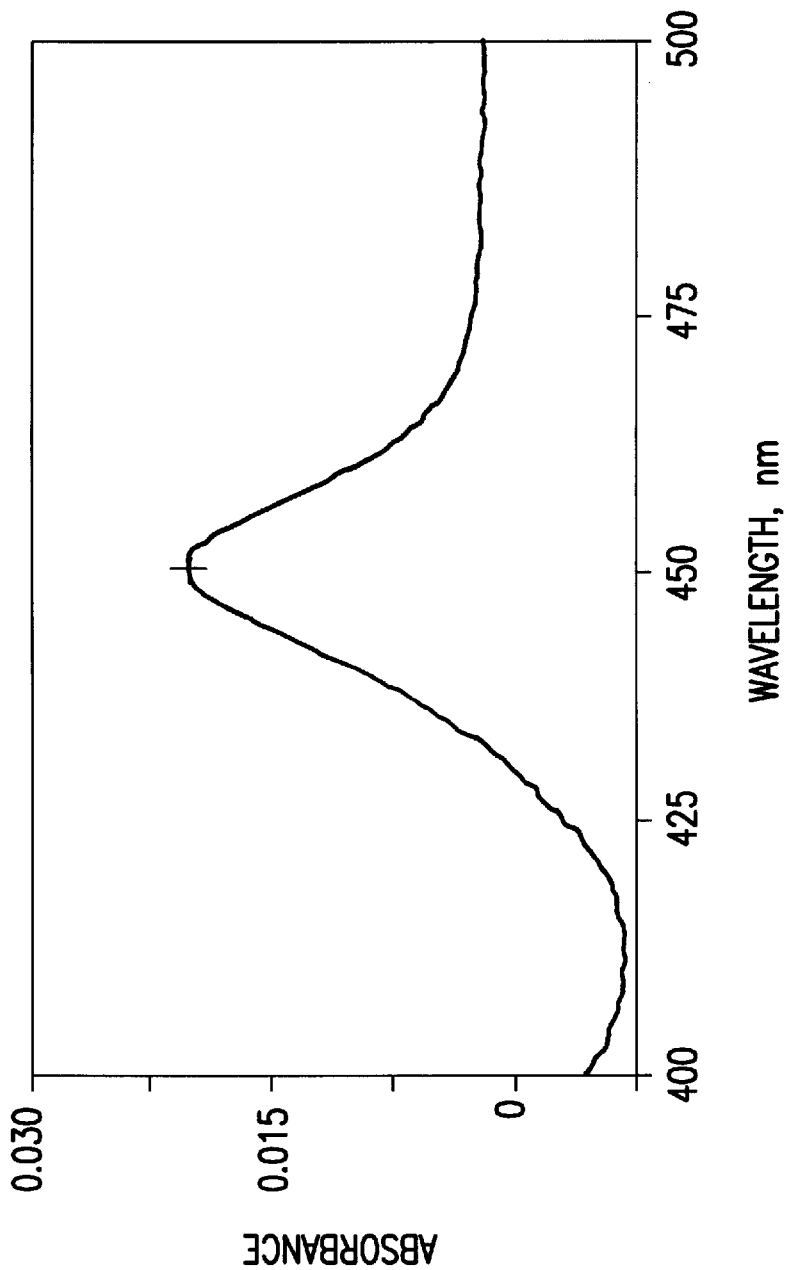

The $Fe^{3+}$ P450 2E1.4MP complex showed a peak at 420 nm (FIG. 30). The $Fe^{2+}$ and $Fe^{2+}$.CO spectra (without 4MP) are typical for P450 proteins. Cytochrome P420 was absent in the absolute (FIG. 30) and $Fe^{2+}$.CO vs $Fe^{2+}$ difference spectra (FIG. 31).

Wavelength maxima and extinction coefficients are presented in Table III.

N-Terminal amino acid sequence analysis. Recombinant human P450 2E1 was analyzed and found to have the terminal Met removed (Table IV), as is usually the case in bacteria when Ala follows N-terminal Met (Hirel et al., *Proc. Natl. Acad. Sci. USA* 86:8247–8251 (1989)). The next 20 expected amino acids were all recovered in good yield.

Figure 32:
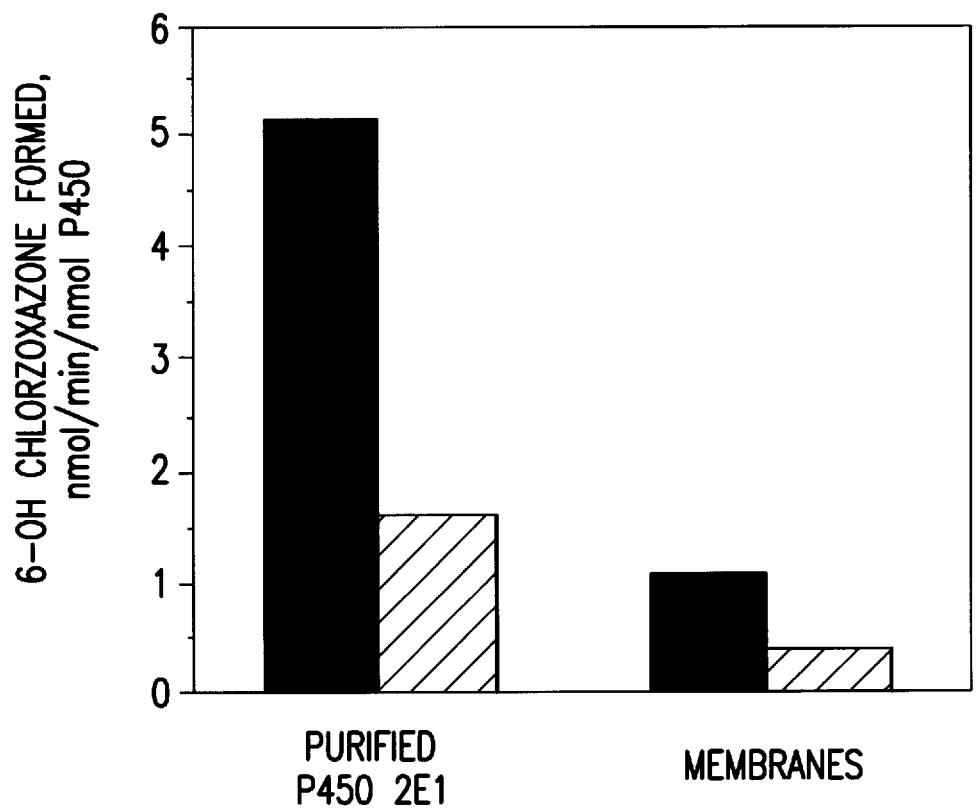
FIG. 32. Chlorzoxazone 6-hydroxylation activity of recombinant human P450 2E1 in bacterial membranes and after purification. Incubations were done with 50 nM P450 2E1 and 1.0 mM chlorzoxazone in the absence □ and presence ■ of 100 nM human liver cytochrome $b_5$.

Catalytic activity. Chlorzoxazone 6-hydroxylation was examined as a prototypic activity of human P450 2E1 (Peter et al., 1990). Initial studies indicated that the activity seen with the purified enzyme was considerably higher than that measured with the enzyme still in *E. coli* membranes (FIG. 32), an observation we made with recombinant human P450 1A2 in *E. coli* membranes (Sandhu et al., 1994). Cytochrome $b_5$ has been shown to stimulate the catalytic activity of human, rat, and rabbit P450 2E1 (Levin et al., *Arch. Biochem. Biophys.* 248:158–165 (1986); Patten et al., *Arch. Biochem. Biophys.* 299:163–171 (1992); Wrighton et al., *Arch. Biochem. Biophys.* 258:292–297; Koop, *Mol. Pharmacol.* 29:399–404 (1986)) and we observed such an effect with both the membranes and purified enzyme (FIG. 32).

Figure 33:
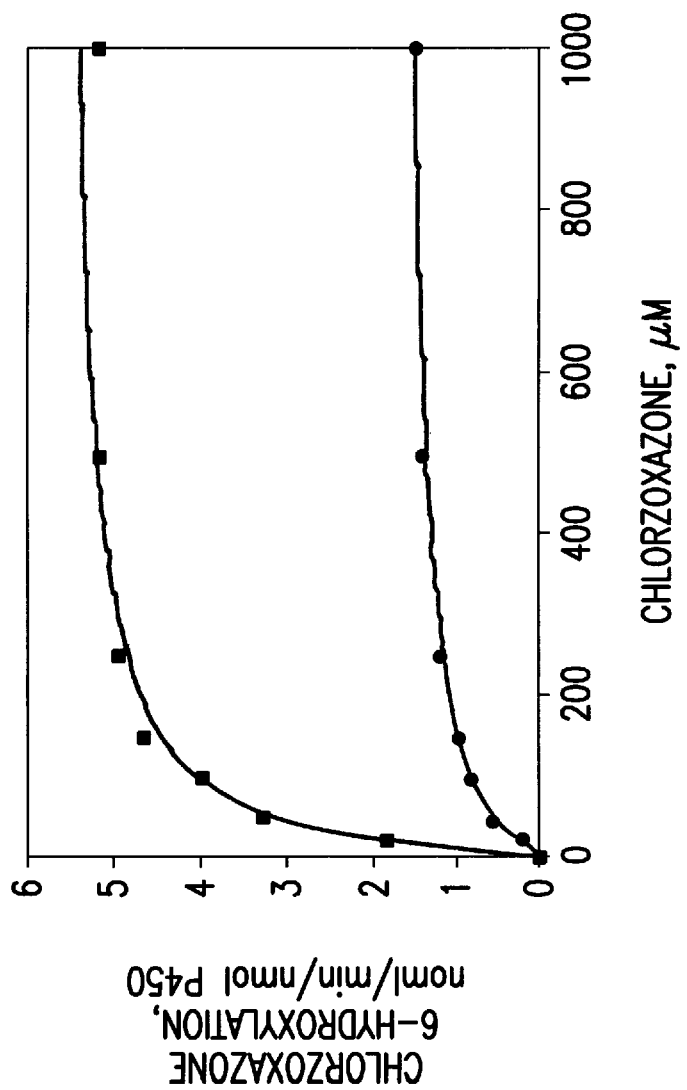
FIG. 33. Effect of cytochrome $b_5$ on 6-hydroxylation of chlorzoxazone by purified recombinant human P450 2E1. Incubations included 50 nM P450 2E1, 150 nM NADPH-P450 reductase, 30 μM L-α-1,2-dilauroyl-sn-glycero-3-phosphocholine in the absence ● or presence ■ of human liver cytochrome $b_5$.
Figure 34:
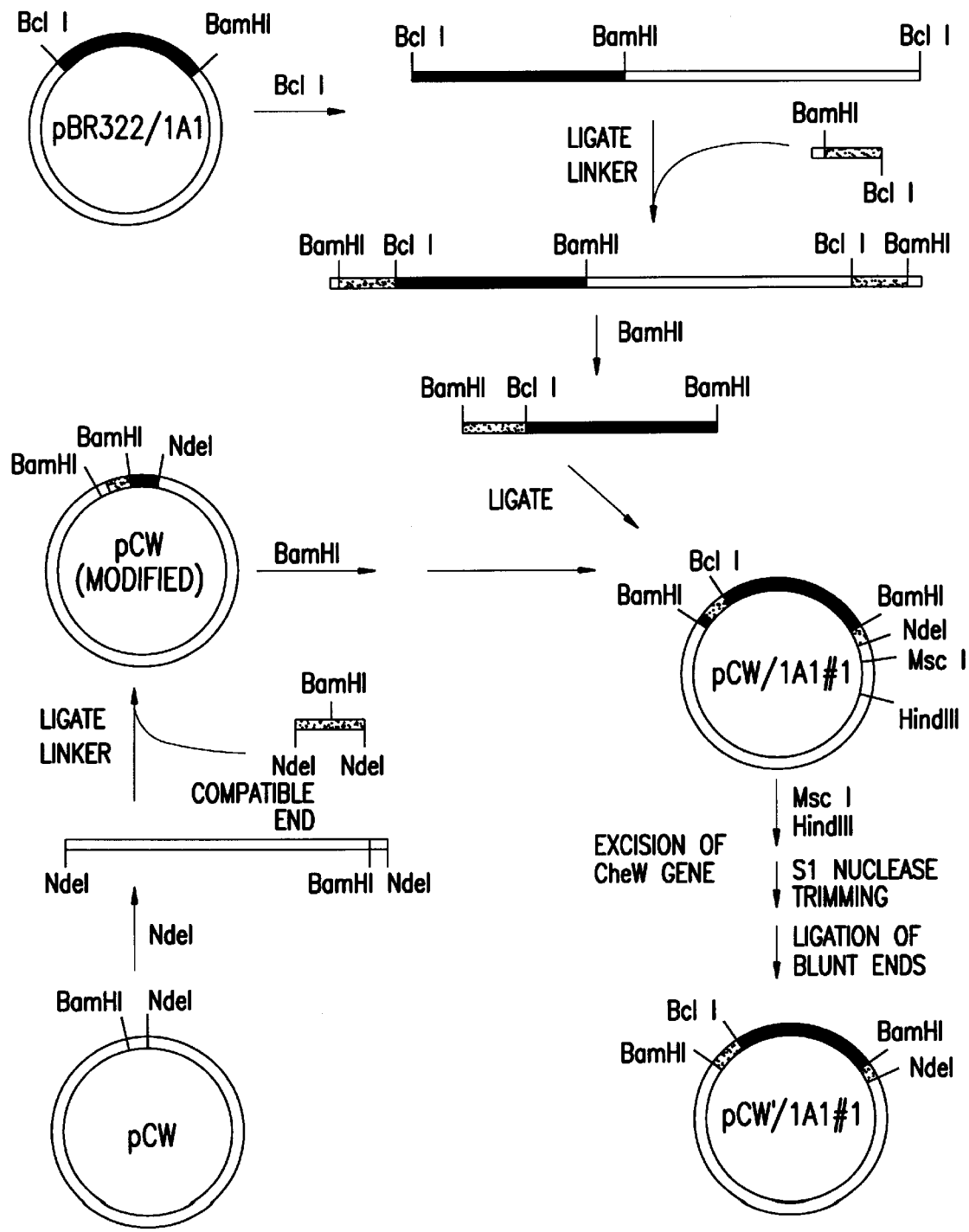
FIG. 34. General strategy for preparation of modified pCW vector containing human P450 1A1 constructs. Construction of the original plasmid in pCW. The cDNA for human P450 1A1 was excised from the subcloning vector in two stages. A BclI cut served to linearize the parent plasmid. A linker containing an internal BamHI site and a BclI end was then ligated to both ends; this linker contained the upstream ribosomal binding sequences required for expression of the cDNA in pCW. This linear DNA was then cut with BamHI and the resultant fragment (containing the P450 1A1 cDNA) was inserted into the BamHI site of a modified pCW vector, in which the Shine-Dalgarno sequences had been removed to eliminate competition for ribosomal binding. Finally, the CheW gene (situated between the promoter and termination signal in the original plasmid) was removed by digestion with MscI and HindIII, S1 nuclease trimming of the protruding ends, and ligation of the resultant blunt ends to recircularize the plasmid.
Figure 35:
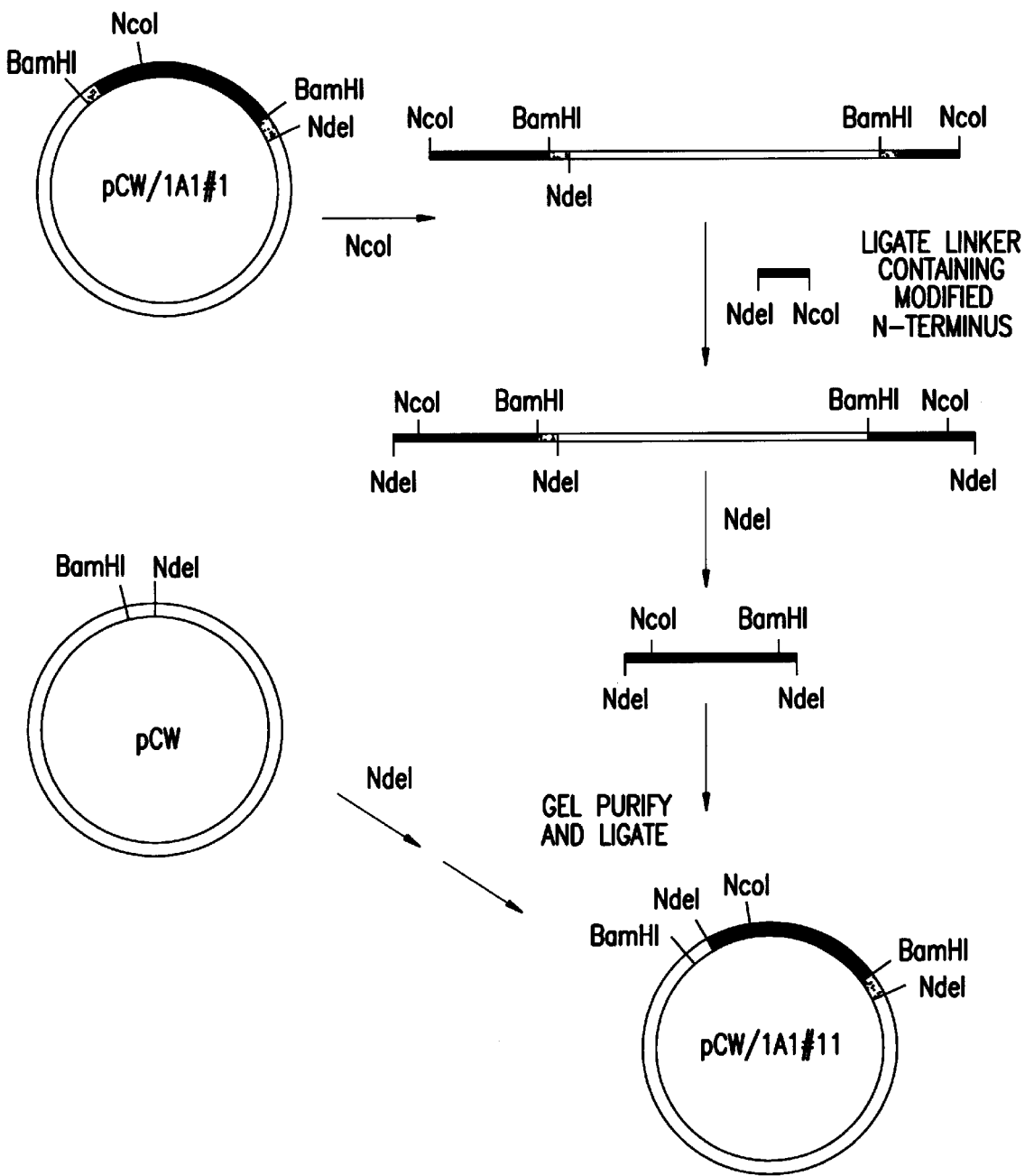
FIG. 35. Constuction of the initial truncated variant P450 1A1 expression plasmid pCW'/1A1#11. The C-terminal portion of P450 1A1 cDNA was excised from pCW'/1A1 as an NcoI-NdeI fragment and then ligated into (unmodified) pCW vector along with an oligonucleotide linker coding for the truncated N-terminus.
Figure 36:
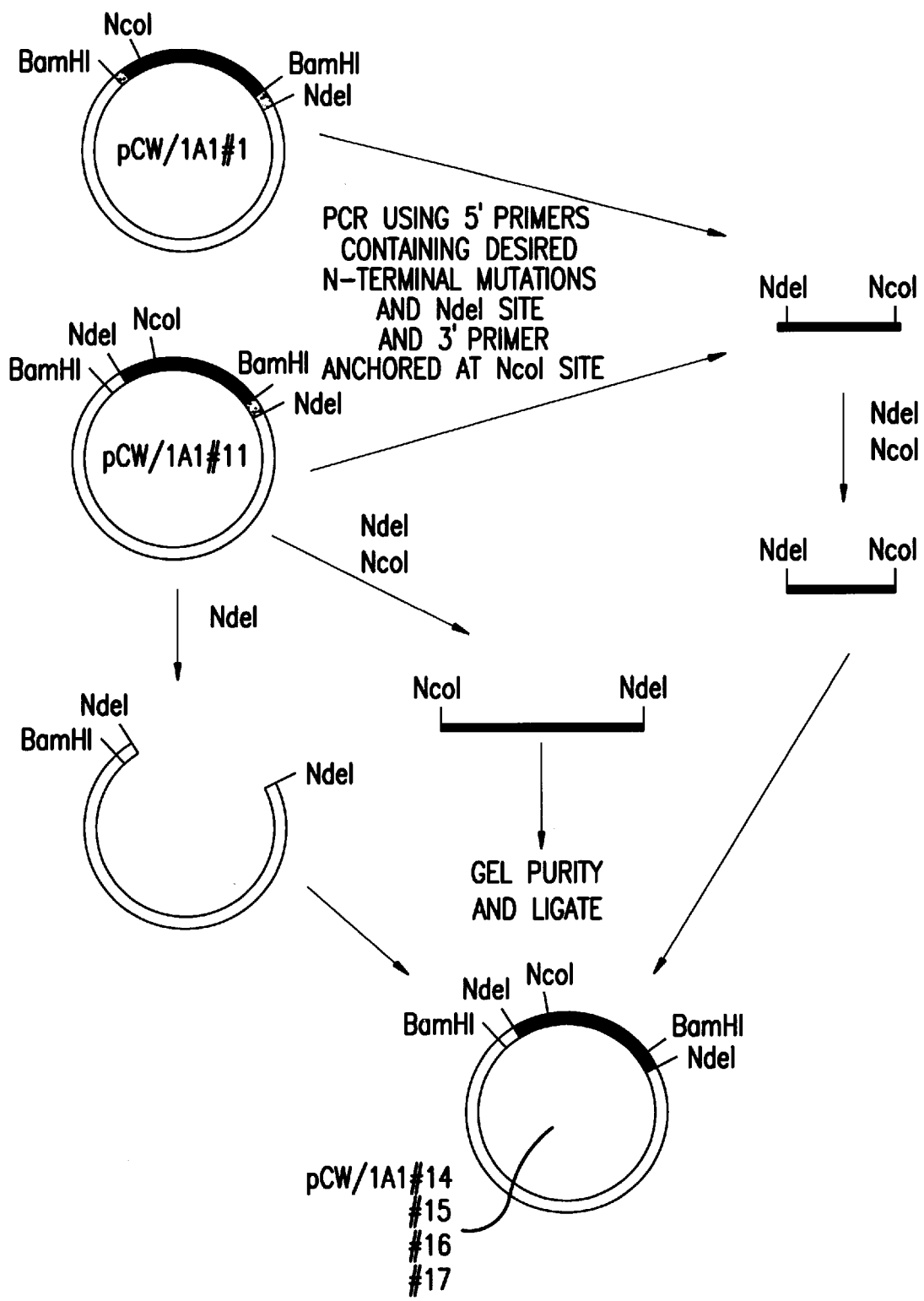
FIG. 36. Construction of novel N-terminal variants of the P450 1A1 expression plasmid. pCW/1A1#1 or pCW/1A1#11 was used as the template for PCR amplification of the N-terminal fragment of the P450 1A1 cDNA between the 5' NdeI and internal NcoI sites. The 5' PCR primers were designed to contain the mutations to be included in the P450 1A1 N-terminal variants. The PCR products were gel-purified and then cut with NdeI and NcoI before ligation into the cognate sites of pCW'/1A1#11, from which the N-terminal P450 1A1 cDNA fragment had been excised.

In more extensive experiments with purified P450 2E1, we found that both the $V_{max}$ and $K_m$ for the reaction were improved by the presence of cytochrome $b_5$ (FIG. 33). The addition of cytochrome $b_5$ changed the $V_{max}$ from 1.65 (±0.06) to 5.56 (±0.16) nmol 6-hydroxychlorzoxazone formed min$^{-1}$ (nmol P450)$^{-1}$ and the $K_m$ from 104 (±12) to 39 (±5) $\mu$M.

Discussion

In this report we describe a system that can be used to reproducibly express a slightly modified form of human P450 2E1 in *E. coli*. The spectral and catalytic properties of the purified enzyme appear to be those expected, and the ready availability of large amounts of this protein should facilitate studies on its physical characteristics and its roles in biotransformations.

A few comments are in order regarding the expression work. First of all, the need to verify sequences of PCR products cannot be overemphasized. Even with the use of the high-fidelity Pfu polymerase we found a mutation that might be expected to block heme incorporation. The second point is that those constructs showing higher apoprotein levels (FIG. 25) also demonstrated more prominent P450 spectra (FIG. 26), suggesting that heme synthesis and insertion are not limiting in this system. It is difficult to make direct comparisons of this system with those of others who have expressed P450 2E1 proteins in *E. coli*, since other vectors were used and each may have its own requirements (Larson et al., 1991a; Larson et al., 1991b; Fujita et al., *DNA Cell Biol.* 9:111–118 (1990)). The native sequence was ineffective in our system and some expression was found when the modified bovine P450 17A terminus MALLLAVFL (SEQ ID NO: 6) (Wada et al., *Arch. Biochem. Biophys.* 290:376–380 (1991)) was substituted (FIG. 26, Table I). However, the most useful procedure seems to be removal of the N-terminal hydrophobic segment in this case (FIG. 24). The presence of a GCT codon (Ala) in position 2 is still considered essential (Barnes et al., *Proc. Natl. Acad Sci. USA* 88:5597–5601 (1991); Wada et al., 1991; Stormo et al., *Nucl. Acids Res.* 10:2971–2996 (1982)), at least with this vector. In contrast to the four *E. coli* -produced P450s with the N-terminal sequence MALLLAVFL (SEQ ID NO: 6) that we have found to contain an (unidentified) N-terminal block, modified P450 2E1 (with MARQVHSS) (SEQ ID NO: 45) yielded excellent sequence results (Table IV). It is difficult to compare our expression yields with those of others for P450 2E1 proteins because of the different methods of expressing yields, but our level appears to be higher [routinely 40 nmol P450 recovered in membranes (liter culture)$^{-1}$].

Recombinant human P450 2E1 expressed and purified in this study was shown to be catalytically active towards chlorzoxazone, a marker substrate for this P450 enzyme in human liver (Peter et al., 1990). Quantitative comparisons of the activity of the expressed enzyme having the modified N-terminus with the native enzyme (which could not be expressed in this system) are not trivial because of the difficulty in purifying the human liver enzyme (Guengerich et al., 1991). However, rates of chlorzoxazone 6-hydroxylation by the recombinant enzyme appear to be approximately those expected on the basis of experience with the liver enzyme (Guengerich et al., 1991) and the dependence of the $V_{max}$ and $K_m$ on cytochrome $b_5$ (FIG. 32) was expected from studies with animal and human P450 2E1 enzymes (Levin et al., 1986; Patten et al., 1992; Wrighton et al., 1987; Koop, 1986). Further studies on catalytic activities towards other known and potential P450 2E1 substrates are in progress.

Finally, the simplicity of the purification system should be noted. The yield is excellent and we have not considered the introduction of an oligo-His insert to be necessary. The same general purification procedure has been useful for the other human P450 proteins we have expressed (Gillam et al., 1993; Sandhu et al., 1993; Sandhu et al., 1994) and may find application with more P450s.

TABLE I

Calculated potential free energy for RNA secondary structure formation (base region −26 to +21 with respect to start codon) and P450 2E1 yields in *E. coli* membranes[a]

| Construct[b] | Secondary structure formation potential, ΔG o (kcal mol$^{-1}$)[c] | Relative apoprotein production[d] | P450 produced, nmol (liter culture)$^{-1}$ [e] |
|---|---|---|---|
| 1 | −9.7 | 13 | <2 |
| 11 | −9.4 | 16 | <2 |
| 14 | −4.8 to −5.0 | 17 | <2 |
| 15 | −3.4 to −3.5 | 55 | 5 |
| 16 | −5.9 | 84 | 8 |
| 17 | −4.8 | 23 | <2 |
| 18 | −4.1 | 100 | 40 |

[a] All trials at 30° C. for 24 h in *E. coli* DH5α cells with 1.0 mM IPTG.
[b] See FIG. 23.
[c] (Zuker, M. Science 244:48–52, 1989, Jaeger et al., 1989a, Jaeger et al. 1989b).
[d] Estimated by densitometry of immunoblots developed with rabbit anti-human P450 2E1 (FIG. 25).
[e] Measured in membranes as described by Omura and Sato, 1964 (FIG. 26).

TABLE II

Purification of P450 2E1 from *E. coli* membrane fraction

| Purification Step | Protein (mg)[a] | P450 (nmol) | Specific content (nmol/mg protein)[a] | Yield (%) |
|---|---|---|---|---|
| Solubilized membranes | 553 | 105 | 0.19 | 100 |
| DEAE (void) | 184 | 96 | 0.53 | 91 |
| CM (gradient) | 6.5 | 85 | 13.1 | 81 |

[a] These values should be considered nominal because of the assay method.

TABLE III

Spectral characteristics of purified recombinant human P450 2E1[a]

| Form of P450 2E1 | Wavelength maximum (nm)[b] | ε (mM$^{-1}$ cm$^{-1}$) |
|---|---|---|
| Fe$^{3+}$ | 393 | c |
|  | 418 | c |
|  | 538 | c |
|  | 640 | c |
| Fe$^{3+}$4MP | 359 | 39.0 |
|  | 422 | 103 |
|  | 543 | 11.4 |
|  | 576 | 9.4 |
| Fe$^{2+}$ | 412 | 75.6 |
|  | 543 | 13.6 |
| Fe$^{2+}$•CO | 450.2 | 121 |
|  | 551 | 13.5 |
| Fe$^{2+}$•CO vs Fe$^{2+}$ (difference) | 450.2 | 91.0[d] |

[a] Spectra were recorded in 0.10M potassium phosphate buffer (pH 7.4) containing 1.0 mM EDTA and 20% glycerol (v/v).
[b] Determined using the peak finder program of the Aminco DW2/OLIS system.
[c] Not calculated because of the presence of a mixture of high and low spin ferric P450 (FIG. 29).
[d] Assumed in making calculations (Omura and Sato, 1964, Imai et al., 1978, Omura and Sato, 1967).

TABLE IV

N-Terminal sequence of modified P450 2E1 purified from *E. coli*

| Cycle/position of DNA | Expected from cDNA | Found | pmol recovered[a] |
|---|---|---|---|
| 1 | M | — | — |
| 2 | A | A | 86 |
| 3 | R | R | 69 |
| 4 | Q | Q | 59 |
| 5 | V | V | 58 |
| 6 | H | H | 30 |
| 7 | S | S | 26 |
| 8 | S | S | 59 |
| 9 | W | W | 13 |
| 10 | N | N | 24 |
| 11 | N | N | 38 |
| 12 | P | P | 35 |
| 13 | P | P | 43 |
| 14 | G | G | 41 |
| 15 | P | P | 37 |
| 16 | F | F | 29 |
| 17 | P | P | 34 |
| 18 | L | L | 35 |
| 19 | P | P | 30 |
| 20 | I | I | 24 |
| 21 | I | I | 32 |

[a]A nominal amount of 130 pmol of purified P450 2E1 was used for NaDodSO$_4$-polyacrylamide gel electrophoresis.

EXAMPLE 5

Expression of Modified Human Cytochrome P450 1A1 in *Escherichia coli*. Effects of 5' Substitution, Stabilization, Purification, Spectral Characterization, and Catalytic Properties Materials and Methods Construction of N-terminal variants of P450 1A1 for expression. The P450 1A1 cDNA, subcloned in pBR322 (Quattrochi et al. *DNA* 4:395–400 1985), codes for the allele containing Ile at amino acid 462. Five different N-terminal variants of the 1A1 sequence were constructed and expressed in pCW in a similar manner as described for P450 3A4 (Gillam et al. *Arch. Biochem Biophys.* 305:123–131, 1993) and P450 2E1 (FIGS. 34–38). The initial (native nucleotide and amino acid sequence) construct was created by excising the P450 1A1 coding sequence from pBR322/1A1 as the BclI/BamHI fragment. This was ligated into pCW using the BamHI site upstream of the start codon. The ribosomal binding sequences of pCW which normally follow this site and immediately precede the start codon were replaced by inserting an appropriate linker. The first modified construct was #11, lacking codons 2–27 and with the subsequent Ala (GCC) codon changed to GCT, a modification that has been associated with improved expression levels in other systems (Larson et al. *J. Biol. Chem.* 266:7321–7324, 1991); Barnes et al. *Proc. Natl. Acad Sci. USA* 88:5597–5601, 1991); Wada et al. *Arch. Biochem. Biophys.* 290:376–380, 1991); Larson et al. *Proc. Natl. Acad. Sci. USA* 88:9141–9145, 1991). This construct was created by excising the NcoI-NdeI 1A1 fragment from construct #1, attaching an NdeI/NcoI linker to code for a truncated N-terminal sequence, and then ligating the resultant fragment into the NdeI site of pCW. Diagnostic restriction digests were used to determine the fidelity of each construct. In both cases, the CheW gene of pCW was excised by an MscI/HindIII digestion of the plasmid, followed by S1 nuclease trimming and ligation of the resultant blunt ends.

A PCR-based strategy was used to create all subsequent N-terminal variants (FIG. 36). pCW'/1A1#1 or #11 was used as template as appropriate. 5' PCR primers were designed to contain the desired modified N-terminal codons as well as the 5' NdeI site to allow subsequent cloning into pCW (FIG. 37). The 3' PCR primer was centered on the NcoI site at position 128 (relative to the start codon). All PCR reactions employed Pfu polymerase under conditions recommended by the manufacturer (Stratagene, La Jolla, Calif.), and an annealing temperature of 58° C. PCR products were gel-purified by the GeneClean II method as described by the manufacturer (Bio 101, La Jolla, Calif.) prior to NdeI/NcoI digestion and cloning into the cognate site of the parent vector.

The potential for self-hybridization of mRNA transcripts of the N-terminal variants was analyzed over the region –26 to +27 nucleotides relative to the start codon using the Mfold program (Zuker *Science* 24:48–52, 1989); Jaeger et al. *Proc. Natl. Acad. Sci. USA* 86:7706–7710, 1989); Jaeger et al., *Methods Enzymol.* 183:281–306,1989).

Bacterial expression. Initial trials were undertaken as described (Gillam et al., 1993) using DH5α cells grown in modified TBamp medium at an induction temperature of 30° C. for 24 h. In these preliminary studies, construct #17 showed highest levels of hemoprotein production and conditions were further optimized for this construct.

Large scales of routine expression were carried out by inoculation of 1.0 liter of TB media with 10 ml of the overnight LBamp culture. The TB media preparation and IPTG induction were done as described (Gillam et al., 1993). The induced culture was shaken vigorously for 48 h at 30° C. in an Innova 4300 shaker (New Brunswick Scientific, Edison, N.J.). Subsequent membrane preparation proceeded essentially as described previously (Gillam et al., 1993).

Purification of recombinant P450 1A1. *E. coli* membrane fractions were diluted to a protein concentration of 2 mg ml$^{-1}$ in 50 mM Tris-HCl buffer (pH 7.4) containing 20% glycerol (v/v), 0.625% sodium cholate (w/v), 0.625% Triton N-101 (w/v), 1.0 mM EDTA, 1.0 mM DTT, and 30 μM αNF. The solublized membrane preparations were stirred at 4° C. for 2 h and centrifuged at 100,000 g for 60 min (4° C.).

The resulting clarified supernatant was loaded onto a 2.5×13-cm DEAE-Sephacel column (Pharmacia, Piscataway, N.J.) equilibrated with the membrane solublization buffer. The void fractions were pooled and concentrated to ⅓ of the original volume with an Amicon device using a PM-30 membrane. To lower the detergent concentration, the concentrated solution was stirred gently with Amberlite XAD-2 beads (Sigma Chemical Co., beads to detergent ratio of 5:1, w/w) for 30 min at 4° C. and filtered through glass wool. The filtrate was diluted to the original volume with a solution of 20% glycerol (v/v), 1.0 mM EDTA, and 1.0 mM DTT and adjusted to pH 6.5. The diluted sample was applied to a 1.5×6-cm CM-Sepharose Fast-Flow column (Pharmacia, Piscataway, N.J.) that had been equilibrated with 20 mM potassium phosphate buffer (pH 6.5) containing 20% glycerol (v/v), 0.20 mM EDTA, and 1.0 mM DTT. The column was sequentially washed with 200 ml each of the CM-Sepharose equilibration buffer and 100 mM potassium phosphate buffer (pH 7.4) containing 20% glycerol (v/v), 0.20 mM EDTA, and 1.0 mM DTT. P450 1A1 was eluted with a linear gradient of 25 to 250 mM potassium phosphate buffer (pH 7.4) (200 ml each) containing 0.20% Triton N-101 (w/v), 30 μM αNF, 20% glycerol (v/v), 0.20 mM EDTA, and 1.0 mM DTT. The fractions that were nearly homogeneous as judged by NaDodSO$_4$-polyacrylamide gel electrophoresis and silver staining were pooled. Detergent and αNF were removed by application to a small hydroxylapatite column, extensive washing, and elution with 500 mM potassium phosphate buffer (pH 7.4) containing 0.30% sodium cholate (w/v), 20% glycerol (v/v), 0.2 mM EDTA, and 1.0 mM DTT. The P450 1A1 elute was dialyzed against 100 mM potassium phosphate buffer (pH 7.4) containing 20% glycerol (v/v), 0.2 mM EDTA, and 1.0 mM DTT for 24 h and stored in small aliquots at −20° C.

Purification of other proteins. Recombinant *E. coli* human P450 1A2 was expressed and purified as described elsewhere (Sandhu et al. *Arch. Biochem. Biophys.*, in press 1993a). NADPH-P450 reductase was purified from liver microsomes prepared from phenobarbital-treated rabbits according to the procedure of Yasukochi and Masters (Yasukochi and Masters *J. Biol. Chem.* 251:5337–5344, 1976) as modified (Shimada et al., *J. Biol. Chem.* 261:909–921 (1986)). Cytochrome $b_5$ was purified from human liver sample HL 104 as described elsewhere (Gillam et al., 1993); Shimada et al., 1986; Funae and Imaoka, *Biochem. Biophys. Acta* 842:119–132 (1985)). Rabbit anti-recombinant human P450 1A2 was raised according to the general procedures described previously (Kaminsky et al., *Methods Enzymol.* 74:262–272 (1981)).

Other assays and methods. P450 spectra were recorded with an Aminco DW2/OLIS instrument (On-Line Instrument Systems, Bogart, Ga.) at ambient temperature according to Omura and Sato (Omura and Sato, *J. Biol. Chem.* 239:2370–2378 (1964); Omura and Sato, *Methods Enzymol.* 10:556–561 (1967)). Wavelength maxima were determined using the peak finder or second derivative analysis software of the Aminco/OLIS instrument, which was calibrated with a holmium oxide filter.

7-Ethoxyresorufin O-dealkylation (Burke and Mayer, *Drug Metab. Dispos.* 3:245–253 (1975); Burke and Mayer, *Chem.-Biol. Interactions* 45:243–258 (1983)) and benzo(a) pyrene 3-hydroxylation (Nebert and Gelboin, *J. Biol. Chem.* 243:6242–6249 (1968); Guengerich in Principles and Methods of Toxicology, Hayes, A. W., Ed., 777–814, Raven Press, New York (1989)) were determined as described elsewhere. Protein concentrations were estimated using a bicinchoninic acid (BCA) method according to the instructions supplied by the manufacturer (Pierce Chemical Co., Rockford, Ill.).

NaDodSO$_4$-polyacrylamide gel electrophoresis was carried out according to the general procedure of Laemmli (Laemmli, *Nature* 277:680–685 (1970)) using an acrylamide concentration of 7.5% (w/v). Proteins were detected by staining with ammonical silver as described by Wray et al. (Wray et al., *Anal. Biochem.* 118:197–203 (1981)). Immunoblotting was done using procedures described previously (Guengerich et al., *Biochemistry* 21:1698–1706 (1982)).

N-terminal amino acid sequence analysis was carried out at the Vanderbilt facility using a modified Applied Biosystems 470A instrument (Applied Biosystems, Foster City, Calif.). NaDodSO$_4$-polyacrylamide gel electrophoresis, transfer to Immobilon membranes (Waters-Millipore, Bedford, Mass.), and staining were done as described elsewhere (Matsudaira, *J. Biol. Chem.* 262:10035–10038 (1987)). Yields from each cycle were estimated by comparison with external standards.

Results and Discussion

Expression of P450 1A1 variants. We developed an expression system for human P450 1A1 in *E. coli* strain DH5α using the plasmid pCW, along lines that have been found successful for other P450 enzymes in this and other laboratories (Larson et al., 1991a, Barnes et al., 1991; Wada et al., 1991); Richardson et al., *Arch. Biochem. Biophys.* 300:510–516 (1993); Nishimoto et al., *Biochemistry* 32:8863–8870 (1993); Fisher et al., *FASEB J.* 6:759–764 (1992); Fisher et al., *Proc. Natl. Acad. Sci. USA* 89:10817–10821 (1992); Gillam et al., 1993); Sandhu and Guengerich, *Arch. Biochem. Biophys.* 306:443–450 (1993); Sandhu et al., 1993a). Several N-terminal variations were introduced into the P450 1A1 sequence in order to find the best strategy by which to facilitate P450 expression in *E. coli*. Four general approaches were employed individually or in combination: i) substitution of the second codon with GCT (Ala); ii) truncation of the N-terminal hydrophobic sequence; iii) minimization of the potential free energy for self-hybridization of the mRNA transcript around the start codon; and iv) substitution of the P450 1A1 N-terminus with that of the modified bovine P450 17α-hydroxylase described by Barnes et al. (Barnes et al., 1991). Constructs #11, 14, 16, and 17 all had GCT as the second codon. Constructs #11 and #16 were truncated. Constructs #14, 15, 15, and 17 were all redesigned to minimize the potential for secondary structure formation around the start codon of the resultant mRNA transcripts; free energies of self-hybridization were predicted using the Mfold program (Zuker, 1989; Jaeger, 1989a; Jaeger, 1989b) and nucleotides were substituted accordingly. Construct #14 had the bovine P450 17α-hydroxylase N-terminus aligned in place of the native P450 1A1 N-terminus.

Preliminary trials showed that levels of hemoprotein and apoprotein expression varied considerably between different N-terminal constructs (Table I). In all cases, a substantial amount of protein was located in the membranes and the 10,000 g pellet fraction (representing protein sequestered in inclusion bodies and unbroken cells). Construct #17 displayed the highest levels of both hemoprotein and apoprotein expression; however, significant expression was also achieved with constructs #14 and #16. Hemoprotein and apoprotein yields were roughly correlated, as was our general experience with other human P450 enzymes expressed in this *E. coli* system (Gillam et al., 1993; Sandhu et al., 1993a; Sandhu et al., 1993b).

Some anecdotal comments may be made regarding the relative success of each of the approaches used here. All constructs showing significant expression contained GCT as the second codon (#14, #16, #17). Although the minimization of self-hybridization may have contributed to the success of these variants (compare #16 with #11 and #15 with #1), no clear correlation could be seen between potential for secondary structure formation in mRNA transcripts and expression level. Such a lack of correlation was also observed with P450 2E1 expression in the same system. Clearly other, as yet undefined factors contribute to determining expression yields and there are no clear rules to allow complete prediction of which approach will produce optimal results with a given P450 cDNA. Although truncation of the hydrophobic sequence and its replacement with that of the modified bovine 17α-hydroxylase have been successful with other enzymes, these strategies were of limited utility with human P450 1A1 and cannot be advocated as universally applicable means of enhancing expression of mammalian P450s in bacteria.

Construct #17 showed routine levels of hemoprotein expression of ~20–25 nmol of P450 recovered in membranes (liter culture)$^{-1}$ and was optimized with respect to induction time (48 h) and temperature (30° C.) before purification trials and further characterization of the enzyme.

Purification of P450 1A1. In our previous experiences with recombinant human P450 1A2 (Sandhu et al., 1993b)

and 2E1, we found that high concentrations of the detergents sodium cholate and Triton N-101 are necessary for complete solublization of *E. coli* membranes and are very convenient for DEAE chromatography. Most of the *E. coli* membrane proteins bind to DEAE-Sephacel and recombinant human P450 proteins elute in the void volume. As in the case of human recombinant 1A2 (Sandhu et al., 1993b), P450 1A1 was denatured to P420 completely in the solublization mixture (data not shown). αNF (at 30 μM) was able to protect against this denaturation of P450 1A1 in the presence of detergents, as in the case of recombinant human P450 1A2 (Sandhu et al., 1993b).

Figure 39A:
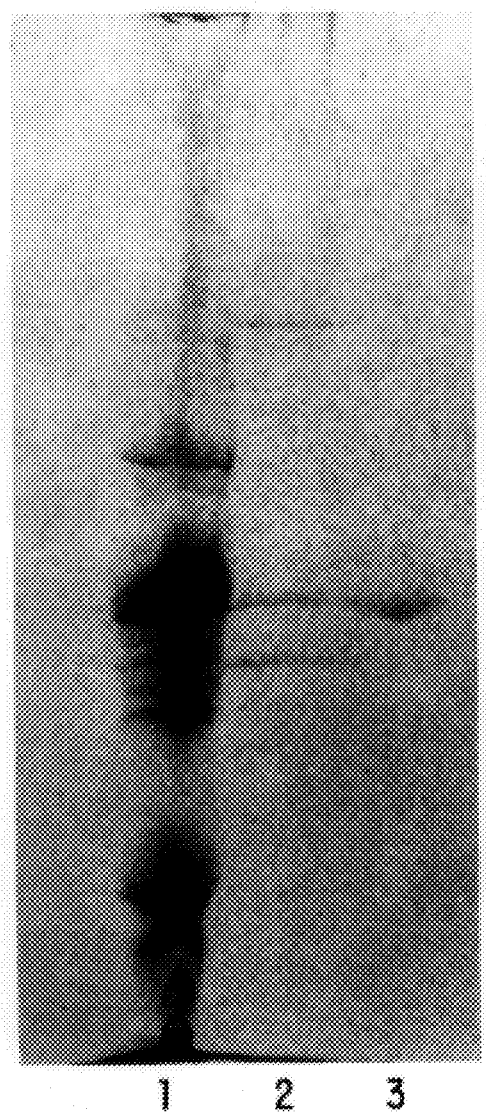
FIG. 39. (A) Purification of recombinant P450 1A1 from *E. coli* membranes. NaDodSO$_4$-polyacrylamide gel electrophoretograms were stained with ammonical silver (54). Lane 1, membranes (300 μg protein); lane 2, DEAE-Sephacel void fraction (50 μg protein); lane 3, CM-Sepharose gradient fraction (0.9 μg protein). (B) Immunoblot analysis of recombinant human P450s 1A1 and 1A2. Lanes 1 and 2 contain 10 pmol of P450 1A1 and 1A2, respectively.

*E. coli* membranes containing P450 1A1 were solublized with sodium cholate and Triton N-101 in the presence of αNF, and the supernatant resulting from centrifugation at 100,000 g was loaded directly onto a DEAE-Sephacel column equilibrated with the solublization buffer. P450 1A1 was recovered in the void volume in high yield (Table II). Decreasing the Tris and cholate concentrations (by concentration with ultrafiltration and dilution) and removal of Triton (with Amberlite XAD-2 beads) were necessary to bind P450 1A1 to the CM-Sepharose Fast-Flow column. Successive washes with low ionic strength phosphate solutions further removed some impurities. The CM column was then eluted with a gradient of increasing phosphate concentration (FIG. 39A). The overall yield for the two column procedures was ~50% (Table II). αNF and detergent were removed using a small hydroxylapatite column.

Figure 39B:
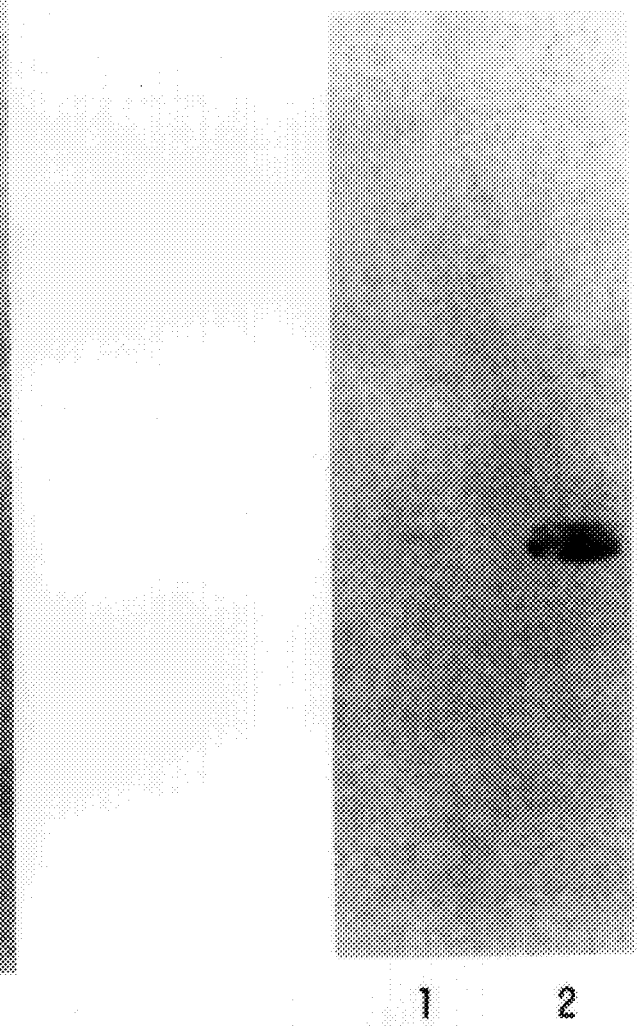

The sequences of human P450s 1A1 and 1A2 are ~80% identical (Quattrochi et al., 1985; Jaiswal et al., *Science* 228:80–83 (1985)). However, the purified recombinant P450 1A1 only reacted weakly with antibodies raised against the recombinant human P450 1A2 (FIG. 39B). (Antibodies have not yet been raised against human P450 1A1.)

Figure 40A:
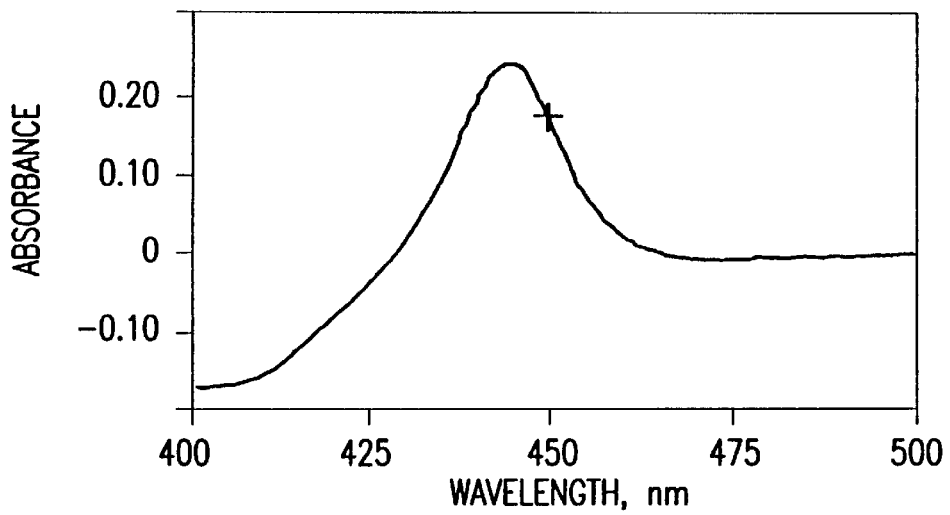
FIG. 40. Spectra of purified recombinant human P450 1A1. All spectra were recorded with 2.6 μM P450 1A1 in 100 mM potassium phosphate buffer (pH 7.4) containing 1.0 mM EDTA and 20% glycerol (v/v). (A) $Fe^{2+}$.CO vs $Fe^{2+}$ difference spectrum. (B) Absolute spectra: $Fe^{3+}$, $Fe^{2+}$, $Fe^{2+}$.CO, as indicated. The inset shows the expanded α,β region. (C) Second derivative spectrum ($Fe^{3+}$).
Figure 40B:
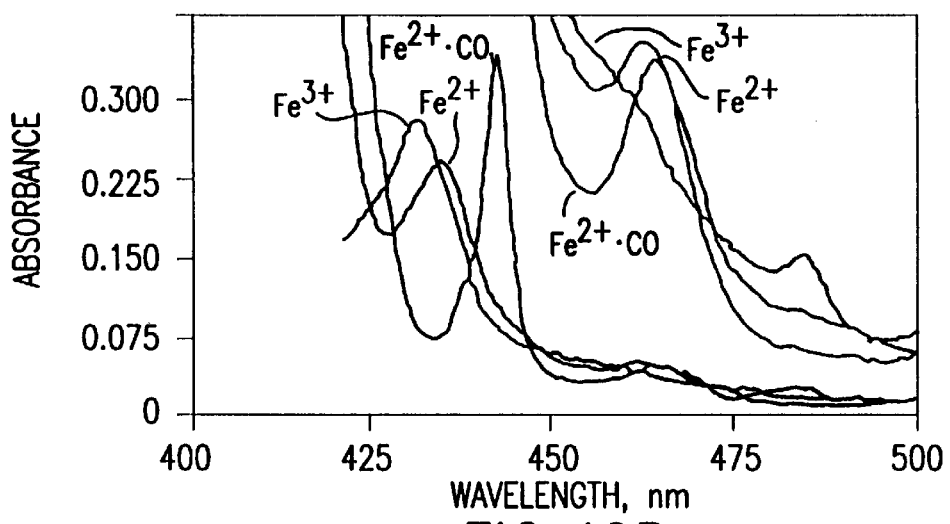
Figure 40C:
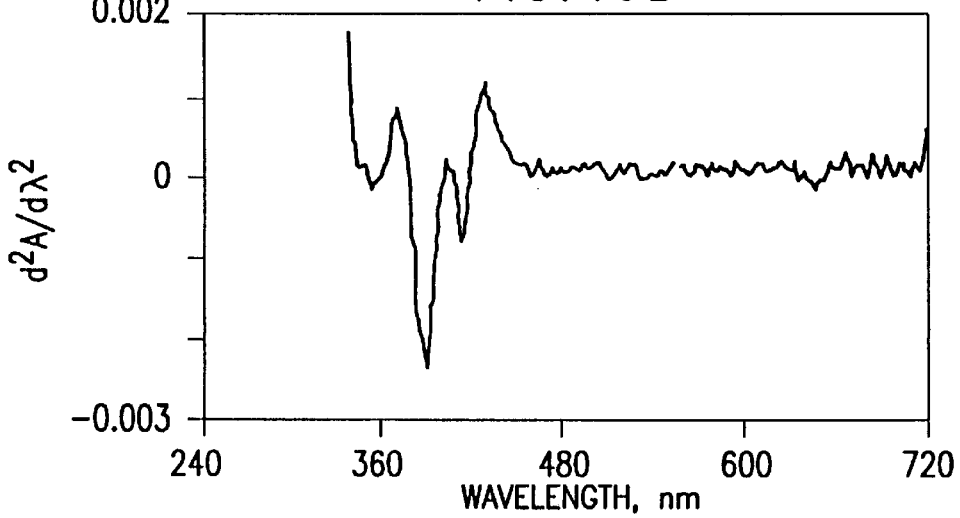

Spectral characterization. Under the conditions used, the final P450 1A1 preparation showed no contamination with P420 after purification (FIGS. 40A,B). In contrast to recombinant human P450 1A2 (Sandhu et al., 1993a), P450 1A1 was readily reduced by $Na_2S_2O_4$. The absolute spectra indicate that P450 1A1 was isolated mainly in a high-spin iron configuration, as denoted by the diagnostic Soret band of the ferric protein (FIG. 40B) (Yu and Gunsalus, *J. Biol. Chem.* 249:102–106 (1974)). The α and β bands are also coalesced and a band is also seen at 644 nm. The high spin nature was also confirmed by second-derivative analysis (Guengerich, *Biochemistry* 22:2811–2820 (1983); O'Haver and Green, *Anal. Chem.* 48:312–318 (1976)) of the ferric Soret band (FIG. 40C). Some low spin iron ($I_{max}$ 417 nm) is present but the level appears to be ~20%.

The $Fe^{2+}$ and $Fe^{2+}.CO$ spectra of purified P450 1A1 are typical for P450 proteins. Cytochrome P420 was not detectable in the absolute (FIG. 40B) and $Fe^{2+}.CO$ vs $Fe^{2+}$ difference spectra (FIG. 40A). Spectra shown in FIG. 40 were used to calculate the extinction coefficients summarized in Table III, which are based on $\Delta\epsilon_{450-490}$=91.0 $mM^{-1}$ $cm^{-1}$ for the $Fe^{2+}.CO$ vs $Fe^{2+}$ difference spectrum (Omura and Sato, 1964; Omura and Sato, 1967).

P450 1A1 proteins isolated from rat liver (Guengerich et al., *Xenobiotica* 12:701–716 (1982)) and rabbit liver (Koop and Coon, *Mol. Pharmacol.* 25:494–501 (1984)) were reported to be mainly in the low-spin iron configuration.

This is clearly not the case for the recombinant human P450 1A1 protein, which is predominantly in the high-spin form. However, this modified human P450 1A1 is the first human P450 1A1 form ever purified as an active protein and direct comparison with a homogenous preparation derived from human tissue is not possible at the present time.

N-terminal amino acid sequence analysis. The recombinant human P450 1A1 was analyzed by automated Edman degradation and found to have the first Met residue removed (Table IV), consistent with most cases when the terminal Met is followed by a Ala residue in bacteria (Hirel et al., *Proc. Natl. Acad. Sci. USA* 86:8247–8251 (1989)). The next 20 predicted amino acids were all detected in good yield.

Figure 41A:
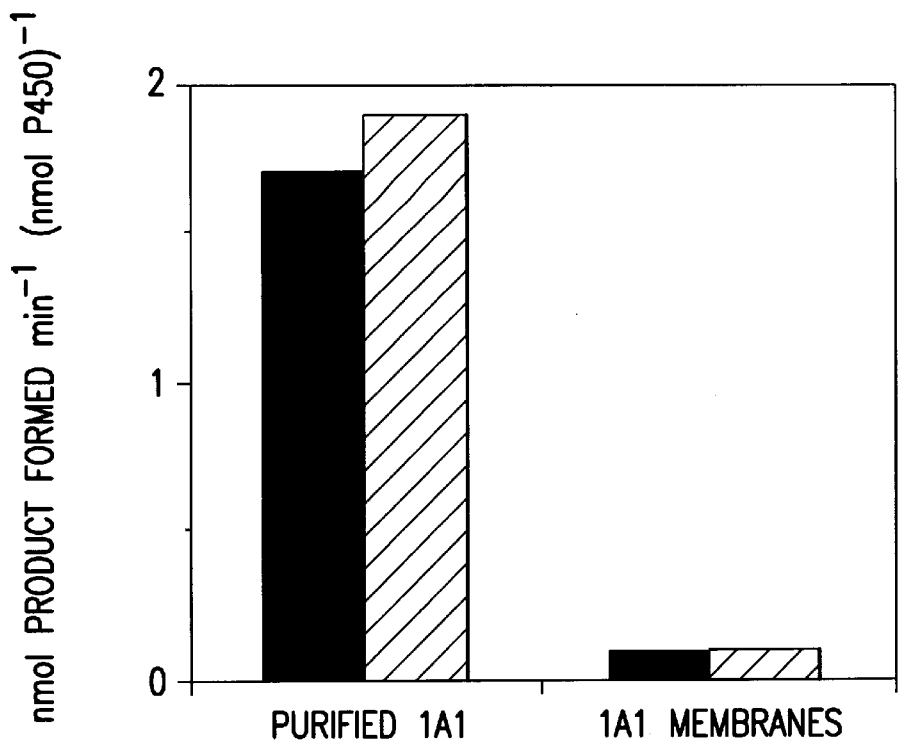
FIG. 41. Benzo(a)pyrene 3-hydroxylation (A) and 7-ethoxyresorufin O-deethylation (B) activities of recombinant human P450 1A1 in bacterial membranes and after purification. Benzo(a)pyrene 3-hydroxylation was assayed with 25 nM P450 1A1, 50 nM NADPH-cytochrome P450 reductase, and 60 μM benzo(a)pyrene in the absence □ and presence ■ of 25 nM human liver cytochrome b$_5$. 7-Ethoxyresorufin O-deethylation activity was assayed with 5 nM P450 1A1, 10 n/M NADPH-cytochrome P450 reductase, and 5 μM 7-ethoxyresorufin in the absence □ and presence ■ of 5 nM human liver cytochrome b$_5$.
Figure 41B:
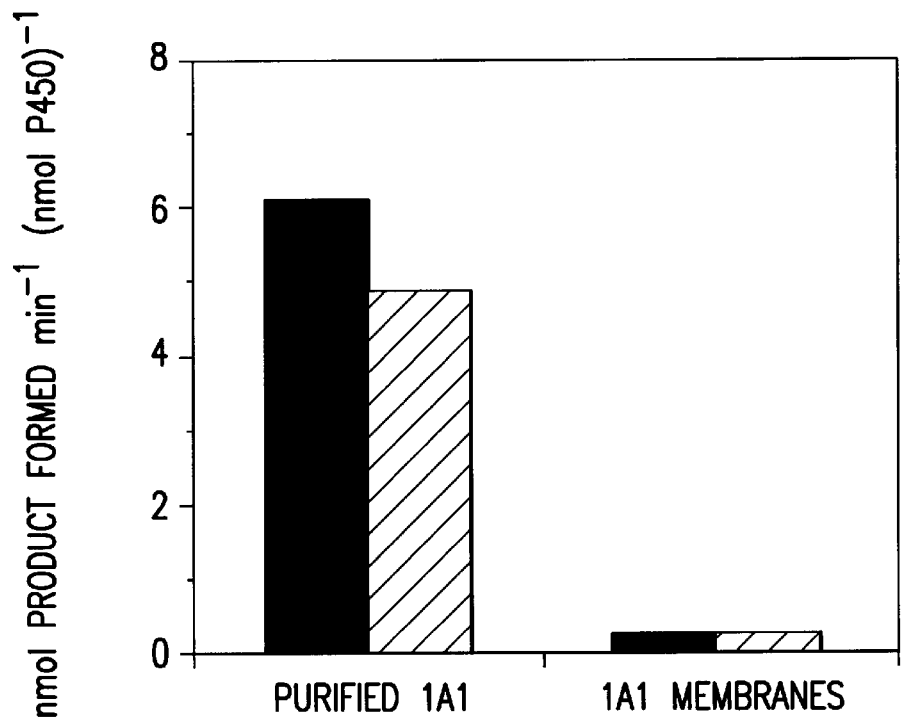
Figure 42A:
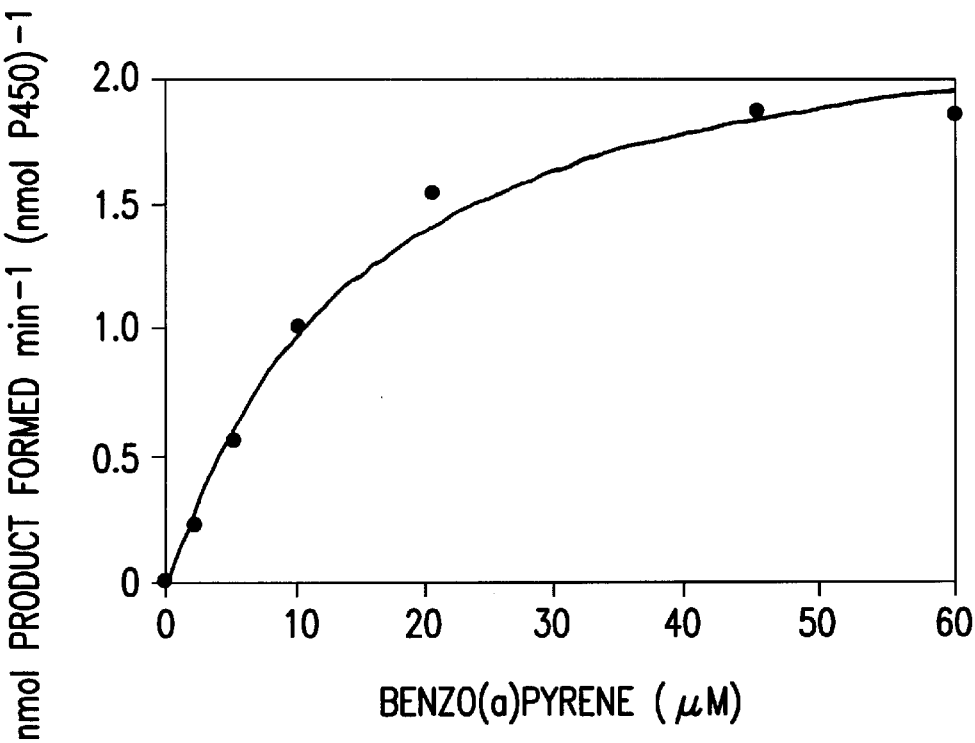
FIG. 42. Substrate concentration-dependent benzo(a) pyrene 3-hydroxylation (A) and 7-ethoxyresorufin O-deethylation (B) in a P450 1A1 reconstutited system. Benzo(a)pyrene 3-hydroxylation were assayed with 25 nM P450 1A1 and 50 nM NADPH-cytochrome P450 reductase. 7-Ethoxyresorufin O-deethylation were assayed with 5 nM P450 1A1 and 10 nM NADPH-cytochrome P450 reductase.
Figure 42B:
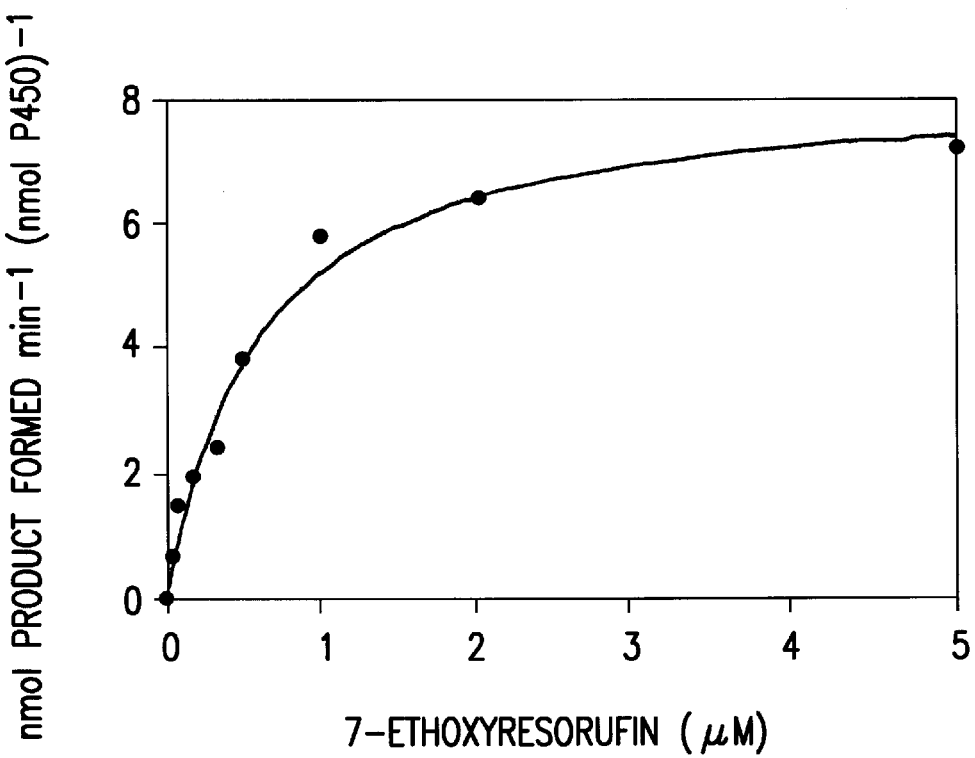

Catalytic activities. The purified P450 1A1 protein was examined for catalytic activities in a conventional reconstitution system containing rabbit NADPH-P450 reductase and L-α-1,2-dilauroyl-sn-glycero-3-phosphocholine. P450 1A1 catalyzed benzo(a)pyrene 3-hydroxylation and 7-ethoxyresorufin O-deethylation at rates of 1.7 and 6.2 nmol product formed $min^{-1}$ (nmol P450)$^{-1}$, respectively (FIGS. 41A,B). The 7-ethoxyresorufin O-deethylation activity of recombinant human P450 1A1 is ~10 fold higher than that of recombinant human P450 1A2 (Sandhu et al., 1993b), consistent with the pattern in the respective rat proteins (61). P450 1A1 only manifested a small fraction of its activities in *E. coli* membranes (FIGS. 41A,B). The lower activities of recombinant human P450 1A1 in *E. coli* membranes are consistent with our observations with other recombinant P450 enzymes. Some purified P450 enzymes are highly dependent upon cytochrome $b_5$. Addition of cytochrome $b_5$ (at a 1:1 ratio to P450) to the P450 1A1 reconstituted system slightly increased the benzo(a)pyrene 3-hydroxylation activity but slightly decreased the 7-ethoxyresorufin O-deethylation activity (FIG. 41). The kinetic parameters were obtained by varying the benzo(a)pyrene and 7-ethoxyresorufin concentrations in the P450 1A1 reconstituted system (FIGS. 42A,B). The apparent $K_m$ values were 15 and 0.58 $\mu M$, and apparent $V_{max}$ values were 2.5 and 8.3 nmol product formed $min^{-1}$ (nmol P450)$^{-1}$, respectively, for benzo(a)pyrene 3-hydroxylation and 7-ethoxyresorufin O-deethylation.

Conclusions. We report the successful expression of a slightly modified human P450 1A1 in *E. coli* and purification of an active form for the first time. Some changes in the 5' terminus were required for efficient expression in this system, and seemingly relatively small changes had dramatic effects on expression levels. It is certainly possible that further changes in the 5' terminus or vector may produce improved expression levels. We cannot conclusively state that the enzyme's properties are not influenced by the 5' modifications. However, a major effect seems unlikely since the isolated enzyme has a considerable level of catalytic activity. The isolated protein is mainly in the high spin iron configuration and very active in catalyzing benzo(a)pyrene 3-hydroxylation and 7-ethoxyresorufin O-deethylation. As in the case of some other human P450s expressed in *E. coli*, we found that the catalytic activity was considerably higher with the purified enzyme than in the membranes. The high yield purification with simple ion exchange steps should be useful in further examination of its catalytic activities and in the generation of antibodies for use as biochemical reagents, which are lacking at the present time.

TABLE I

Calculated Potential Free Energy for RNA Secondary Structure Formation (Base Region −26 to +27) with Respect to Start Codon and P450 1A1 Yields in E. coli Membranes[a]

| Construct[b] | Secondary structure formation potential, $\Delta G°$ (kcal mol$^{-1}$)c | Relative apoprotein production[d] | P450 produced, nmol (liter culture)$^{-1e}$ |
|---|---|---|---|
| 1 | −6.9 | <2 | <2 |
| 11 | −9.4 | 7 | <2 |
| 14 | −4.8 to −5.0 | 53 | 14 |
| 15 | −3.8 | 13 | <2 |
| 16 | −5.6 | 34 | 15 |
| 17 | −5.1 | 100 | 25 |

[a]All trials were at 30° C. for 24 h in E. coli DH5α cells with 1.0 mM IPTG.
[b]See FIG. 37.
[c](40–42)
[d]Estimated by densitometry of immunoblots developed with rabbit anti-rat P450 1A1 (data not shown), expressed in relative units.
[e]Measured in membranes as described by Omura and Sato, 1964.

TABLE II

Purification of P450 1A1 from E. coli Membrane Fraction

| Purification step | Protein (mg)[a] | P450 (nmol) | Specific content (nmol/mg protein)[a] | Yield (%) |
|---|---|---|---|---|
| Solubilized membranes | 4500 | 150 | 0.03 | 100 |
| DEAE (void) | 694 | 125 | 0.18 | 83 |
| CM (gradient) | 7.3 | 77 | 10.6 | 51 |

[a]These values should be considered nominal because of the assay method.

TABLE III

Spectral Characteristics of Purified Recombinant Human P450 1A1[a]

| Form of P450 1A1 | Wavelength maximum (nm)[b] | $\epsilon$ (mM$^{-1}$ cm$^{-1}$) |
|---|---|---|
| $Fe^{3+}$ | 391 | c |
|  | 644 | c |
| $Fe^{2+}$ | 407 | 90.7 |
|  | 540 | 17.6 |
| $Fe^{2+}$•CO | 445 | 129 |
|  | 549 | 16.4 |
| $Fe^{2+}$•CO vs $Fe^{2+}$ (difference) | 445 | 91.0[d] |

Spectra were recorded in 0.10 M potassium phosphate buffer (pH 7.4) containing 1.0 mM EDTA and 20% glycerol (v/v).
[b]Determined using the peak finder program of the Aminco DW2/OLIS system.
[c]Not calculated because of the presence of a mixture of high and low spin ferric P450 (FIG. 40).
[d]Assumed in making calculations (Omura and Sato, 1964, Omura and Sato, 1967).

TABLE IV

N-Terminal Amino Acid Sequence of P450 1A1 Purified from E. coli

| Cycle/position of DNA | Expected from cDNA | Found | pmol recovered[a] |
|---|---|---|---|
| 1 | M | — | — |
| 2 | A | A | 26 |
| 3 | F | F | 19 |
| 4 | P | P | 15 |
| 5 | I | I | 15 |
| 6 | S | S | 13 |
| 7 | M | M | 10 |
| 8 | S | S | 12 |
| 9 | A | A | 15 |
| 10 | T | T | 12 |
| 11 | E | E | 9 |
| 12 | F | F | 12 |
| 13 | L | L | 16 |
| 14 | L | L | 19 |
| 15 | A | A | 17 |
| 16 | S | S | 10 |
| 17 | V | V | 11 |
| 18 | I | I | 12 |
| 19 | F | F | 11 |
| 20 | C | X | — |
| 21 | L | L | 17 |

[a]A nominal amount of 100 pmol of purified P450 1A1 was used for the NaDodSO$_4$-polyacrylamide gel electrophoresis and transfer.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of purifying a recombinant cytochrome P450 protein from a host cell culture comprising the steps of:
   a. fractionating the host cells to prepare their membranes;
   b. adding a non-ionic detergent in a concentration of between 0.8% to 2% (w/v) and in a detergent to protein ratio of between 4:1 to 10:1 to the membranes;
   c. adding an ionic detergent in a concentration of between 0.4% to 0.8% (w/v) and in a detergent to protein ratio of between 2:1 to 4:1 to the membranes;
   d. centrifuging the membrane detergent mixture to remove insoluble materials; and,
   e. purifying the protein in the following order:
      i) through a diethylaminoethyl-beaded column;
      ii) through a carboxymethyl-beaded column; and
      iii) through a hydroxylapatite column.

2. The method of claim 1, wherein the protein is selected from the group consisting of cytochrome P450s 2C10, 2E1 and 1A1.

3. The method of claim 1, wherein the non-ionic detergent is in a concentration of about 1.25% (w/v) and in a detergent to protein ratio of about 6:1.

4. The method of claim 1, wherein the ionic detergent is in a concentration of about 0.6% (w/v) and in a detergent to protein ratio of about 3:1.

5. The method of claim 1, wherein the non-ionic detergent is selected from the group consisting of TRITON N-101, EMULGEN-911, EMULGEN-913, TERGITOL-NP10, and LUBROL-PX.

6. The method of claim 1, wherein the ionic detergent is sodium cholate.

7. The method of claim 1, further comprising the step of adding a strong inhibitory ligand before adding the detergents to the fractionated cells.

8. The method of claim 7, wherein the protein is selected from the group consisting of P450 1A2 and 1A1, and the inhibitory ligand is α-naphthoflavone (7,8-benzoflavone).

9. The method of claim 1, wherein the protein is human cytochrome P450 3A4, and further comprising the final step of preincubating the purified protein with glutathione.

* * * * *

SEQUENCE LISTING ( 1 ) GENERAL INFORMATION:

( i i i ) NUMBER OF SEQUENCES: 68

( 2 ) INFORMATION FOR SEQ ID NO:1:

( i ) SEQUENCE CHARACTERISTICS:
        ( A ) LENGTH: 1482 base pairs
        ( B ) TYPE: nucleic acid
        ( C ) STRANDEDNESS: single
        ( D ) TOPOLOGY: linear ( i i ) MOLECULE TYPE: DNA (genomic)

(  x  i  ) SEQUENCE DESCRIPTION: SEQ ID NO:1:

| | | | | | | |
|---|---|---|---|---|---|---|
| ATGTCTGCCC | TCGGAGTGAC | CGTGGCCCTG | CTGGTGTGGG | CGGCCTTCCT | CCTGCTGGTG | 60 |
| TCCATGTGGA | GGCAGGTGCA | CAGCAGCTGG | AATCTGCCCC | CAGGTCCTTT | CCCGCTTCCC | 120 |
| ATCATCGGGA | ACCTCTTCCA | GTTGGAATTG | AAGAATATTC | CCAAGTCCTT | CACCCGGTTG | 180 |
| GCCCAGCGCT | TCGGGCCGGT | GTTCACGCTG | TACGTGGGCT | CGCAGCGCAT | GGTGGTGATG | 240 |
| CACGGCTACA | AGGCGGTGAA | GGAAGCGCTG | CTGGACTACA | AGGACGAGTT | CTCGGGCAGA | 300 |
| GGCGACCTCC | CCGCGTTCCA | TGCGCACAGG | GACAGGGGAA | TCATTTTTAA | TAATGGACCT | 360 |
| ACCTGGAAGG | ACATCCGGCG | GTTTTCCCTG | ACCACCCTCC | GGAACTATGG | GATGGGGAAA | 420 |
| CAGGGCAATG | AGAGCCGGAT | CCAGAGGGAG | GCCCACTTCC | TGCTGGAAGC | ACTCAGGAAG | 480 |
| ACCCAAGGCC | AGCCTTTCGA | CCCCACCTTC | CTCATCGGCT | GCGCGCCCTG | CAACGTCATA | 540 |
| GCCGACATCC | TCTTCCGCAA | GCATTTTGAC | TACAATGATG | AGAAGTTTCT | AAGGCTGATG | 600 |
| TATTTGTTTA | ATGAGAACTT | CCACCTACTC | AGCACTCCCT | GGCTCCAGCT | TTACAATAAT | 660 |
| TTTCCCAGCT | TTCTACACTA | CTTGCCTGGA | AGCCACAGAA | AAGTCATAAA | AAATGTGGCT | 720 |
| GAAGTAAAAG | AGTATGTGTC | TGAAAGGGTG | AAGGAGCACC | ATCAATCTCT | GGACCCCAAC | 780 |
| TGTCCCCGGG | ACCTCACCGA | CTGCCTGCTC | GTGGAAATGG | AGAAGGAAAA | GCACAGTGCA | 840 |
| GAGCGCTTGT | ACACAATGGA | CGGTATCACC | GTGACTGTGG | CCGACCTGTT | CTTTGCGGGG | 900 |
| ACAGAGACCA | CCAGCACAAC | TCTGAGATAT | GGGCTCCTGA | TTCTCATGAA | ATACCCTGAG | 960 |
| ATCGAAGAGA | AGCTCCATGA | AGAAATTGAC | AGGGTGATTG | GGCCAAGCCG | AATCCCTGCC | 1020 |
| ATCAAGGATA | GGCAAGAGAT | GCCCTACATG | GATGCTGTGG | TGCATGAGAT | TCAGCGGTTC | 1080 |
| ATCACCCTCG | TGCCCTCCAA | CCTGCCCCAT | GAAGCAACCC | GAGACACCAT | TTTCAGAGGA | 1140 |
| TACCTCATCC | CCAAGGGCAC | AGTCGTAGTG | CCAACTCTGG | ACTCTGTTTT | GTATGACAAC | 1200 |
| CAAGAATTTC | CTGATCCAGA | AAAGTTTAAG | CCAGAACACT | TCCTGAATGA | AAATGGAAAG | 1260 |
| TTCAAGTACA | GTGACTATTT | CAAGCCATTT | TCCACAGGAA | AACGAGTGTG | TGCTGGAGAA | 1320 |
| GGCCTGGCTC | GCATGGAGTT | GTTTCTTTTG | TTGTGTGCCA | TTTTGCAGCA | TTTTAATTTG | 1380 |
| AAGCCTCTCG | TTGACCCAAA | GGATATCGAC | CTCAGCCCTA | TACATATTGG | GTTTGGCTGT | 1440 |
| ATCCCACCAC | GTTACAAACT | CTGTGTCATT | CCCCGCTCAT | GA | | 1482 |

( 2 ) INFORMATION FOR SEQ ID NO:2:

( i ) SEQUENCE CHARACTERISTICS:
        ( A ) LENGTH: 1419 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO (  x  ) SEQUENCE DESCRIPTION: SEQ ID NO:2:

| | | | | | | |
|---|---|---|---|---|---|---|
| ATGGCTCGTC | AAGTTCATTC | TTCTTGGAAT | CTGCCCCCAG | GTCCTTTCCC | GCTTCCCATC | 60 |
| ATCGGGAACC | TCTTCCAGTT | GGAATTGAAG | AATATTCCCA | GTCCTTCAC | CCGGTTGGCC | 120 |
| CAGCGCTTCG | GGCCGGTGTT | CACGCTGTAC | GTGGGCTCGC | AGCGCATGGT | GGTGATGCAC | 180 |
| GGCTACAAGG | CGGTGAAGGA | AGCGCTGCTG | GACTACAAGG | ACGAGTTCTC | GGGCAGAGGC | 240 |
| GACCTCCCCG | CGTTCCATGC | GCACAGGGAC | AGGGGAATCA | TTTTTAATAA | TGGACCTACC | 300 |
| TGGAAGGACA | TCCGGCGGTT | TTCCCTGACC | ACCCTCCGGA | ACTATGGGAT | GGGGAAACAG | 360 |

| | | | | | | |
|---|---|---|---|---|---|---|
| GGCAATGAGA | GCCGGATCCA | GAGGGAGGCC | CACTTCCTGC | TGGAAGCACT | CAGGAAGACC | 420 |
| CAAGGCCAGC | CTTTCGACCC | CACCTTCCTC | ATCGGCTGCG | CGCCCTGCAA | CGTCATAGCC | 480 |
| GACATCCTCT | TCCGCAAGCA | TTTTGACTAC | AATGATGAGA | AGTTTCTAAG | GCTGATGTAT | 540 |
| TTGTTTAATG | AGAACTTCCA | CCTACTCAGC | ACTCCTGGC | TCCAGCTTTA | CAATAATTTT | 600 |
| CCCAGCTTTC | TACACTACTT | GCCTGGAAGC | CACAGAAAAG | TCATAAAAAA | TGTGGCTGAA | 660 |
| GTAAAGAGT | ATGTGTCTGA | AAGGGTGAAG | GAGCACCATC | AATCTCTGGA | CCCCAACTGT | 720 |
| CCCCGGGACC | TCACCGACTG | CCTGCTCGTG | GAAATGGAGA | AGGAAAAGCA | CAGTGCAGAG | 780 |
| CGCTTGTACA | CAATGGACGG | TATCACCGTG | ACTGTGGCCG | ACCTGTTCTT | TGCGGGGACA | 840 |
| GAGACCACCA | GCACAACTCT | GAGATATGGG | CTCCTGATTC | TCATGAAATA | CCCTGAGATC | 900 |
| GAAGAGAAGC | TCCATGAAGA | AATTGACAGG | GTGATTGGGC | CAAGCCGAAT | CCCTGCCATC | 960 |
| AAGGATAGGC | AAGAGATGCC | CTACATGGAT | GCTGTGGTGC | ATGAGATTCA | GCGGTTCATC | 1020 |
| ACCCTCGTGC | CCTCCAACCT | GCCCCATGAA | GCAACCCGAG | ACACCATTTT | CAGAGGATAC | 1080 |
| CTCATCCCCA | AGGGCACAGT | CGTAGTGCCA | ACTCTGGACT | CTGTTTGTA | TGACAACCAA | 1140 |
| GAATTTCCTG | ATCCAGAAAA | GTTTAAGCCA | GAACACTTCC | TGAATGAAAA | TGGAAAGTTC | 1200 |
| AAGTACAGTG | ACTATTTCAA | GCCATTTTCC | ACAGGAAAAC | GAGTGTGTGC | TGGAGAAGGC | 1260 |
| CTGGCTCGCA | TGGAGTTGTT | TCTTTTGTTG | TGTGCCATTT | TGCAGCATTT | TAATTTGAAG | 1320 |
| CCTCTCGTTG | ACCCAAAGGA | TATCGACCTC | AGCCCTATAC | ATATTGGGTT | TGGCTGTATC | 1380 |
| CCACCACGTT | ACAAACTCTG | TGTCATTCCC | CGCTCATGA | | | 1419 |

( 2 ) INFORMATION FOR SEQ ID NO:3:

( i ) SEQUENCE CHARACTERISTICS:
        ( A ) LENGTH: 1591 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

| | | | | | | |
|---|---|---|---|---|---|---|
| ATGGATAGCC | TAGTGGTCCT | TGTGCTCTGT | CTCTCATGTT | TGCTTCTCCT | TTCACTCTGG | 60 |
| AGACAGAGCT | CTGGGAGAGG | AAAACTCCCT | CCTGGCCCCA | CTCCTCTCCC | AGTGATTGGA | 120 |
| AATATCCTAC | AGATAGGTAT | TAAGGACATC | AGCAAATCCT | TAACCAATCT | CTCAAAGGTC | 180 |
| TATGGCCCTG | TGTTCACTCT | GTATTTGGC | CTGAAACCCA | TAGTGGTGCT | GCATGGATAT | 240 |
| GAAGCAGTGA | AGGAAGCCCT | GATTGATCTT | GGAGAGGAGT | TTTCTGGAAG | AGGCATTTTC | 300 |
| CCACTGGCTG | AAAGAGCTAA | CAGAGGATTT | GGAATTGTTT | TCAGCAATGG | AAAGAAATGG | 360 |
| AAGGAGATCC | GGCGTTTCTC | CCTCATGACG | CTGCGGAATT | TGGGATGGG | AAGAGGAGC | 420 |
| ATTGAGGACC | GTGTTCAAGA | GGAAGCCCGC | TGCCTTGTGG | AGGAGTTGAG | AAAAACCAAG | 480 |
| GCCTCACCCT | GTGATCCAC | TTTCATCCTG | GGCTGTGCTC | CCTGCAATGT | GATCTGCTCC | 540 |
| ATTATTTTCC | ATAAACGTTT | TGATTATAAA | GATCAGCAAT | TTCTTAACTT | AATGGAAAAG | 600 |
| TTGAATGAAA | ACATCAAGAT | TTTGAGCAGC | CCCTGGATCC | AGATCTGCAA | TAATTTTTCT | 660 |
| CCTATCATTG | ATTACTTCCC | GGGAACTCAC | AACAAATTAC | TTAAAAACGT | TGCTTTTATG | 720 |
| AAAAGTTATA | TTTTGGAAAA | AGTAAAAGAA | CACCAAGAAT | CAATGGACAT | GAACAACCCT | 780 |

| | | | | | | |
|---|---|---|---|---|---|---|
| CAGGACTTTA | TTGATTGCTT | CCTGATGAAA | ATGGAGAAGG | AAAAGCACAA | CCAACCATCA | 840 |
| GAATTTACTA | TTGAAAGCTT | GGAAAACACT | GCAGTTGACT | TGTTTGGAGC | TGGGACAGAG | 900 |
| ACGACAAGCA | CAACCCTGAG | ATATGCTCTC | CTTCTCCTGC | TGAAGCACCC | AGAGGTCACA | 960 |
| GCTAAAGTCC | AGGAAGAGAT | TGAACGTGTG | ATTGGCAGAA | ACCGGAGCCC | CTGCATGCAA | 1020 |
| GACAGGAGCC | ACATGCCCTA | CACAGATGCT | GTGGTGCACG | AGGTCCAGAG | ATGCATTGAC | 1080 |
| CTTCTCCCCA | CCAGCCTGCC | CCATGCAGTG | ACCTGTGACA | TTAAATTCAG | AAACTATCTC | 1140 |
| ATTCCCAAGG | GCACAACCAT | ATTAATTTCC | CTGACTTCTG | TGCTACATGA | CAACAAAGAA | 1200 |
| TTTCCCAACC | CAGAGATGTT | TGACCCTCAT | CACTTTCTGG | ATGAAGGTGA | CAATTTTAAG | 1260 |
| AAAAGTAAAT | ACTTCATGCC | TTTCTCAGCA | GGAAAACGGA | TTTGTGTGGG | AGAAGCCCTG | 1320 |
| GCCGGCATGG | AGCTGTTTTT | ATTCCTGACC | TCCATTTTAC | AGAACTTTAA | CCTGAAATCT | 1380 |
| CTGGTTGACC | CAAAGAACCT | TGACACCACT | CCAGTTGTCA | ATGGATTTGC | CTCTGTGCCG | 1440 |
| CCCTTCTACC | AGCTGTGCTT | CATTCCTGTC | TGAAGAAGAG | CAGATGGCCT | GGCTGCTGCT | 1500 |
| CAGTCCCTGC | AGCTCTCTTT | CCTCTGGGGC | GATTATCCAT | CTTTGCTACA | TTACAGAAAT | 1560 |
| GGAGATGCTG | CTGAGATGAG | AAAGGGAATT | C | | | 1591 |

( 2 ) INFORMATION FOR SEQ ID NO:4:

( i ) SEQUENCE CHARACTERISTICS:
        ( A ) LENGTH: 1419 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

| | | | | | | |
|---|---|---|---|---|---|---|
| ATGGCTCGAC | AATCTTCTGG | ACGAGGAAAA | CTCCCTCCTG | GCCCCACTCC | TCTCCCAGTG | 60 |
| ATTGGAAATA | TCCTACAGAT | AGGTATTAAG | GACATCAGCA | AATCCTTAAC | CAATCTCTCA | 120 |
| AAGGTCTATG | GCCCTGTGTT | CACTCTGTAT | TTTGGCCTGA | AACCCATAGT | GGTGCTGCAT | 180 |
| GGATATGAAG | CAGTGAAGGA | AGCCCTGATT | GATCTTGGAG | AGGAGTTTTC | TGGAAGAGGC | 240 |
| ATTTTCCCAC | TGGCTGAAAG | AGCTAACAGA | GGATTTGGAA | TTGTTTTCAG | CAATGGAAAG | 300 |
| AAATGGAAGG | AGATCCGGCG | TTTCTCCCTC | ATGACGCTGC | GGAATTTTGG | GATGGGGAAG | 360 |
| AGGAGCATTG | AGGACCGTGT | TCAAGAGGAA | GCCCGCTGCC | TTGTGGAGGA | GTTGAGAAAA | 420 |
| ACCAAGGCCT | CACCCTGTGA | TCCCACTTTC | ATCCTGGGCT | GTGCTCCCTG | CAATGTGATC | 480 |
| TGCTCCATTA | TTTTCCATAA | ACGTTTTGAT | TATAAAGATC | AGCAATTTCT | TAACTTAATG | 540 |
| GAAAAGTTGA | ATGAAAACAT | CAAGATTTTG | AGCAGCCCCT | GGATCCAGAT | CTGCAATAAT | 600 |
| TTTTCTCCTA | TCATTGATTA | CTTCCCGGGA | ACTCACAACA | AATTACTTAA | AAACGTTGCT | 660 |
| TTTATGAAAA | GTTATATTTT | GGAAAAGTA | AAGAACACC | AAGAATCAAT | GGACATGAAC | 720 |
| AACCCTCAGG | ACTTTATTGA | TTGCTTCCTG | ATGAAAATGG | AGAAGGAAAA | GCACAACCAA | 780 |
| CCATCAGAAT | TTACTATTGA | AAGCTTGGAA | AACACTGCAG | TTGACTTGTT | TGGAGCTGGG | 840 |
| ACAGAGACGA | CAAGCACAAC | CCTGAGATAT | GCTCTCCTTC | TCCTGCTGAA | GCACCCAGAG | 900 |
| GTCACAGCTA | AAGTCCAGGA | AGAGATTGAA | CGTGTGATTG | CAGAAACCG | GAGCCCCTGC | 960 |
| ATGCAAGACA | GGAGCCACAT | GCCCTACACA | GATGCTGTGG | TGCACGAGGT | CCAGAGATGC | 1020 |
| ATTGACCTTC | TCCCCACCAG | CCTGCCCCAT | GCAGTGACCT | GTGACATTAA | ATTCAGAAAC | 1080 |

| TATCTCATTC | CCAAGGGCAC | AACCATATTA | ATTTCCCTGA | CTTCTGTGCT | ACATGACAAC | 1140 |
| AAAGAATTTC | CCAACCCAGA | GATGTTTGAC | CCTCATCACT | TTCTGGATGA | AGGTGACAAT | 1200 |
| TTTAAGAAAA | GTAAATACTT | CATGCCTTTC | TCAGCAGGAA | AACGGATTTG | TGTGGGAGAA | 1260 |
| GCCCTGGCCG | GCATGGAGCT | GTTTTTATTC | CTGACCTCCA | TTTTACAGAA | CTTTAACCTG | 1320 |
| AAATCTCTGG | TTGACCCAAA | GAACCTTGAC | ACCACTCCAG | TTGTCAATGG | ATTTGCCTCT | 1380 |
| GTGCCGCCCT | TCTACCAGCT | GTGCTTCATT | CCTGTCTGA  |            |            | 1419 |

( 2 ) INFORMATION FOR SEQ ID NO:5:

( i ) SEQUENCE CHARACTERISTICS:
        ( A ) LENGTH: 512 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:5:

```
Met Ala Phe Pro Ile Ser Met Ser Ala Thr Glu Phe Leu Leu Ala Ser
  1               5                  10                  15

Val Ile Phe Cys Leu Val Phe Trp Val Met Arg Ala Ser Arg Pro Gln
                 20                  25                  30

Val Pro Lys Gly Leu Lys Asn Pro Pro Gly Pro Trp Gly Trp Pro Leu
             35                  40                  45

Ile Gly His Met Leu Thr Leu Gly Lys Asn Pro His Leu Ala Leu Ser
         50                  55                  60

Arg Met Ser Gln Gln Tyr Gly Asp Val Leu Gln Ile Arg Ile Gly Thr
 65                  70                  75                  80

Pro Val Val Val Leu Ser Gly Leu Asp Thr Ile Arg Gln Ala Leu Val
                 85                  90                  95

Arg Gln Gly Asp Asp Phe Lys Gly Arg Pro Asp Leu Tyr Thr Phe Thr
                100                 105                 110

Leu Ile Ser Asn Gly Gln Ser Met Ser Phe Ser Pro Asp Ser Gly Pro
             115                 120                 125

Val Trp Ala Ala Arg Arg Arg Leu Ala Gln Asn Gly Leu Lys Ser Phe
         130                 135                 140

Ser Ile Ala Ser Asp Pro Ala Ser Ser Thr Ser Cys Tyr Leu Glu Glu
145                 150                 155                 160

His Val Ser Lys Glu Ala Glu Val Leu Ile Ser Thr Leu Gln Glu Leu
                165                 170                 175

Met Ala Gly Pro Gly His Phe Asn Pro Tyr Arg Tyr Val Val Val Ser
             180                 185                 190

Val Thr Asn Val Ile Cys Ala Ile Cys Phe Gly Arg Arg Tyr Asp His
         195                 200                 205

Asn His Gln Glu Leu Leu Ser Leu Val Asn Leu Asn Asn Phe Gly
     210                 215                 220

Glu Val Val Gly Ser Gly Asn Pro Ala Glu Phe Ile Pro Ile Leu Arg
225                 230                 235                 240

Tyr Leu Pro Asn Pro Ser Leu Asn Ala Phe Lys Asp Leu Asn Glu Lys
                245                 250                 255

Phe Tyr Ser Phe Met Gln Lys Met Val Lys Glu His Tyr Lys Thr Phe
             260                 265                 270
```

|     |     |     |     |     |     |     |     |     |     |     |     |     |     |     |
| --- | --- | --- | --- | --- | --- | --- | --- | --- | --- | --- | --- | --- | --- | --- |
| Glu | Lys | Gly<br>275 | His | Ile | Arg | Asp | Ile<br>280 | Thr | Asp | Ser | Leu | Ile<br>285 | Glu | His | Cys |
| Gln | Glu<br>290 | Lys | Gln | Leu | Asp | Glu<br>295 | Asn | Ala | Asn | Val | Gln<br>300 | Leu | Ser | Asp | Glu |
| Lys<br>305 | Ile | Ile | Asn | Ile | Val<br>310 | Leu | Asp | Leu | Phe | Gly<br>315 | Ala | Gly | Phe | Asp | Thr<br>320 |
| Val | Thr | Thr | Ala | Ile<br>325 | Ser | Trp | Ser | Leu | Met<br>330 | Tyr | Leu | Val | Met | Asn<br>335 | Pro |
| Arg | Val | Gln | Arg<br>340 | Lys | Ile | Gln | Glu | Glu<br>345 | Leu | Asp | Thr | Val | Ile<br>350 | Gly | Arg |
| Ser | Arg | Arg<br>355 | Pro | Arg | Leu | Ser | Asp<br>360 | Arg | Ser | His | Leu | Pro<br>365 | Tyr | Met | Glu |
| Ala | Phe<br>370 | Ile | Leu | Glu | Thr | Phe<br>375 | Arg | His | Ser | Ser | Phe<br>380 | Val | Pro | Phe | Thr |
| Ile<br>385 | Pro | His | Ser | Thr | Thr<br>390 | Arg | Asp | Thr | Ser | Leu<br>395 | Lys | Gly | Phe | Tyr | Ile<br>400 |
| Pro | Lys | Gly | Arg | Cys<br>405 | Val | Phe | Val | Asn | Gln<br>410 | Trp | Gln | Ile | Asn | His<br>415 | Asp |
| Gln | Lys | Leu | Trp<br>420 | Val | Asn | Pro | Ser | Glu<br>425 | Phe | Leu | Pro | Glu | Arg<br>430 | Phe | Leu |
| Thr | Pro | Asp<br>435 | Gly | Ala | Ile | Asp | Lys<br>440 | Val | Leu | Ser | Glu | Lys<br>445 | Val | Ile | Ile |
| Phe | Gly<br>450 | Met | Gly | Lys | Arg | Lys<br>455 | Cys | Ile | Gly | Glu | Thr<br>460 | Val | Ala | Arg | Trp |
| Glu<br>465 | Val | Phe | Leu | Phe | Leu<br>470 | Ala | Ile | Leu | Leu | Gln<br>475 | Arg | Val | Glu | Phe | Ser<br>480 |
| Val | Pro | Leu | Gly | Val<br>485 | Lys | Val | Asp | Met | Thr<br>490 | Pro | Ile | Tyr | Gly | Leu<br>495 | Thr |
| Met | Lys | His | Ala<br>500 | Cys | Cys | Glu | His | Phe<br>505 | Gln | Met | Gln | Leu | Arg<br>510 | Ser | Glx |

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO:6:

| Met | Ala | Leu | Leu | Leu | Ala | Val | Phe | Leu |
| --- | --- | --- | --- | --- | --- | --- | --- | --- |
| 1   |     |     |     | 5   |     |     |     |     |

( 2 ) INFORMATION FOR SEQ ID NO:7:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:7:

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
            20                  25                  30

Phe Lys Lys
        35

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:8:

Met Ala Tyr Gly Thr His Ser His Gly Leu Phe Lys Lys
1               5                   10

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:9:

Met Ala Leu Leu Leu Ala Val Phe Lys Lys
1               5                   10

( 2 ) INFORMATION FOR SEQ ID NO:10:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:10:

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
            20                  25                  30

Phe Lys Lys
        35

( 2 ) INFORMATION FOR SEQ ID NO:11:

(i) SEQUENCE CHARACTERISTICS:
    (A) LENGTH: 25 amino acids
    (B) TYPE: amino acid
    (C) STRANDEDNESS: single
    (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:11:

```
Met Ala Leu Leu Leu Ala Val Phe Leu Val Leu Leu Tyr Leu Tyr Gly
 1               5                  10                  15
Thr His Ser His Gly Leu Phe Lys Lys
             20              25
```

(2) INFORMATION FOR SEQ ID NO:12:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

TTAGGAGGTC ATATGGCTCT GTTATTAGCA GTTTTCTGG TGCTCCTC    48

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

GAGGTGTGGG CCCTGGAATT CCAAGCTTCT TAAAAA    36

(2) INFORMATION FOR SEQ ID NO:14:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:14:

```
Met Asp Ser Leu Val Val Leu Val Leu Cys Leu Ser Cys Leu Leu Leu
 1               5                  10                  15
Leu Ser Leu Trp Arg Gln Ser Ser Gly Arg Gly Lys Leu Pro Pro Gly
```

|  |  |  |  |
|---|---|---|---|
| 20 | | 25 | 30 |

Pro Thr Pro Leu Pro Val Ile Gly
    35                40

( 2 ) INFORMATION FOR SEQ ID NO:15:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:15:

Met Ala Leu Leu Leu Ala Val Phe Leu Cys Leu Ser Cys Leu Leu Leu
1               5                   10                  15

Leu Ser Leu Trp Arg Gln Ser Ser Gly Arg Gly Lys Leu Pro Pro Gly
            20                  25                  30

Pro Thr Pro Leu Pro Val Ile Gly
        35              40

( 2 ) INFORMATION FOR SEQ ID NO:16:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:16:

Met Ala Leu Leu Leu Ala Val Phe Leu Pro Val Ile Gly
1               5                   10

( 2 ) INFORMATION FOR SEQ ID NO:17:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:17:

Met Ala Leu Leu Leu Ala Val Phe Val Leu Cys Leu Ser Cys Leu Leu
1               5                   10                  15

Leu Leu Ser Leu Trp Arg Gln Ser Ser Gly Arg Gly Lys Leu Pro Pro
            20                  25                  30

Gly Pro Thr Pro Leu Pro Val Ile Gly
            35              40

( 2 ) INFORMATION FOR SEQ ID NO:18:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:18:

```
Met  Ala  Arg  Gln  Ser  Ser  Gly  Arg  Gly  Lys  Leu  Pro  Pro  Gly  Pro  Thr
1                   5                        10                       15
Pro  Leu  Pro  Val  Ile  Gly
              20
```

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:19:

ATGGATAGCC TAGTGGTCCT TGTG        24

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

ATGGCTCTGT TATTAGCAGT TTTT        24

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:21:

ATGGCTCGAC AATCTTCTGG ACGA        24

( 2 ) INFORMATION FOR SEQ ID NO:22:

( i ) SEQUENCE CHARACTERISTICS:
   ( A ) LENGTH: 39 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

CATATGGCTC TGTTATTAGC AGTTTTTGTG CTCTGTCTC    39

( 2 ) INFORMATION FOR SEQ ID NO:23:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

CATATGGCTC GACAATCTTC TGGACGAGGA AAACTCCCT    39

( 2 ) INFORMATION FOR SEQ ID NO:24:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

ATGGATAGAC AGAGCTCTGG GAGA    24

( 2 ) INFORMATION FOR SEQ ID NO:25:

( i ) SEQUENCE CHARACTERISTICS:
      ( A ) LENGTH: 40 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:25:

```
Met Ala Leu Ser Gln Ser Val Pro Phe Ser Ala Thr Glu Leu Leu Leu
 1               5                  10                  15

Ala Ser Ala Ile Phe Cys Leu Val Phe Trp Val Leu Lys Gly Leu Arg
             20                  25                  30

Pro Arg Val Pro Lys Gly Leu Lys
             35                  40
```

( 2 ) INFORMATION FOR SEQ ID NO:26:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:26:

```
Met  Ala  Leu  Leu  Leu  Ala  Val  Phe  Phe  Ser  Ala  Thr  Glu  Leu  Leu  Leu
1                   5                        10                      15
Ala  Ser  Ala  Ile  Phe  Cys  Leu  Val  Phe  Trp  Val  Leu  Lys  Gly  Leu  Arg
               20                       25                      30
Pro  Arg  Val  Pro  Lys  Gly  Leu  Lys
               35                  40
```

( 2 ) INFORMATION FOR SEQ ID NO:27:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:27:

```
Met  Ala  Leu  Leu  Leu  Ala  Val  Phe  Lys  Gly  Leu  Arg  Pro  Arg  Val  Pro
1                   5                        10                      15
Lys  Gly  Leu  Lys
               20
```

( 2 ) INFORMATION FOR SEQ ID NO:28:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:28:

```
Met  Ala  Leu  Leu  Leu  Ala  Val  Phe  Leu  Phe  Cys  Leu  Val  Phe  Trp  Val
1                   5                        10                      15
Leu  Lys  Gly  Leu  Arg  Pro  Arg  Val  Pro  Lys  Gly  Leu  Lys
               20                       25
```

( 2 ) INFORMATION FOR SEQ ID NO:29:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear (  i  i  ) MOLECULE TYPE: peptide ( i i i ) HYPOTHETICAL: NO ( v ) FRAGMENT TYPE: N-terminal ( x i ) SEQUENCE DESCRIPTION: SEQ ID NO:29:

```
Met  Ala  Lys  Gly  Leu  Arg  Pro  Arg  Val  Pro  Lys  Gly  Leu  Lys
 1             5                        10
```

( 2 ) INFORMATION FOR SEQ ID NO:30:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:30:

ATGGCACTTC TCCTGGCCTC TGCCATC                                                  27

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:31:

ATGGCTCTGT TATTAGCAGT TTTTCTG                                                  27

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:32:

ATGGCTAAGG GTTTGAGGCC TCGG                                                      24

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:33:

ATGGCTAAAG GATTACGACC ACGA 24

( 2 ) INFORMATION FOR SEQ ID NO:34:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:34:

ATGGCTCTGT TATTAGCAGT TTTTCTG 27

( 2 ) INFORMATION FOR SEQ ID NO:35:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:35:

ATGGCTAAAG GATTACGACC ACGA 24

( 2 ) INFORMATION FOR SEQ ID NO:36:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:36:

CAGCGGCCAT ATGTCTGCCC TCGCA 25

( 2 ) INFORMATION FOR SEQ ID NO:37:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO

-continued ( x i ) SEQUENCE DESCRIPTION: SEQ ID NO:37:

ATCCTGAACT CAAACAATTT GAAAGCTTGT TTGAAAAGCG                                  40

( 2 ) INFORMATION FOR SEQ ID NO:38:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:38:

CATCCCATAG TTCCGGAGGG TGGTCAG                                                27

( 2 ) INFORMATION FOR SEQ ID NO:39:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:39:

Met Ser Ala Leu Gly Val Thr Val Ala Leu Leu Val Trp Ala Ala Phe
1               5                   10                  15

Leu Leu Leu Val Ser Met Trp Arg Gln Val His Ser Ser
                20              25

( 2 ) INFORMATION FOR SEQ ID NO:40:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:40:

Met Trp Arg Gln Val His Ser Ser
1               5

( 2 ) INFORMATION FOR SEQ ID NO:41:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:41:

Met Ala Leu Leu Leu Ala Val Phe Leu Leu Leu Val Ser Met Trp Arg
1               5                   10                  15

Gln Val His Ser Ser
            20

( 2 ) INFORMATION FOR SEQ ID NO:42:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:42:

Met Ser Ala Leu Gly Val Thr Val Ala Leu Leu Val Trp Ala Ala Phe
1               5                   10                  15

Leu Leu Leu Val Ser Met Trp Arg Gln Val His Ser Ser
            20                  25

( 2 ) INFORMATION FOR SEQ ID NO:43:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:43:

Met Trp Arg Gln Val His Ser Ser
1               5

( 2 ) INFORMATION FOR SEQ ID NO:44:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:44:

Met Ala Ala Leu Gly Val Thr Val Ala Leu Leu Val Trp Ala Ala Phe
1               5                   10                  15

Leu Leu Leu Val Ser Met Trp Arg Gln Val His Ser Ser
            20                  25

( 2 ) INFORMATION FOR SEQ ID NO:45:

( i ) SEQUENCE CHARACTERISTICS:
        ( A ) LENGTH: 8 amino acids ( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:45:

Met Ala Arg Gln Val His Ser Ser
1               5

( 2 ) INFORMATION FOR SEQ ID NO:46:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:46:

CCAGCGGCCA TATGTCTGCC CTCGGA 26

( 2 ) INFORMATION FOR SEQ ID NO:47:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:47:

CTGCTGGTGC ATATGTGGAG GCA 23

( 2 ) INFORMATION FOR SEQ ID NO:48:

( i ) SEQUENCE CHARACTERISTICS:
( A ) LENGTH: 63 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:48:

GGAGGTCATA TGGCTCTGTT ATTAGCAGTT TTTCTGCTGC TGGTGTCCAT GTGGCGCCAG 60

GTG 63

( 2 ) INFORMATION FOR SEQ ID NO:49:

( i ) SEQUENCE CHARACTERISTICS:
( A ) LENGTH: 41 base pairs
( B ) TYPE: nucleic acid (C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:49:

TTAGGAGGTC ATATGTCTGC TTTAGGATAA CTGTTGCTCT G　　　　　　41

(2) INFORMATION FOR SEQ ID NO:50:

(i) SEQUENCE CHARACTERISTICS:
(A) LENGTH: 48 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:50:

TTAGGAGGTC ATATGTGGCG TCAAGTTCAT TCTTCTTGGA ATCTGCCC　　　　48

(2) INFORMATION FOR SEQ ID NO:51:

(i) SEQUENCE CHARACTERISTICS:
(A) LENGTH: 42 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:51:

TTAGGAGGTC ATATGGCTGC TTTAGGAGTA ACTGTTGCTC TG　　　　　　42

(2) INFORMATION FOR SEQ ID NO:52:

(i) SEQUENCE CHARACTERISTICS:
(A) LENGTH: 48 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:52:

TTAGGAGGTC ATATGGCTCG TCAAGTTCAT TCTTCTTGGA ATCTGCCC　　　　48

(2) INFORMATION FOR SEQ ID NO:53:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: DNA (genomic)

(iii) HYPOTHETICAL: NO (iv) ANTI-SENSE: NO (xi) SEQUENCE DESCRIPTION: SEQ ID NO:53:

GGCTGGATCC ATCGATGCTT AGGAGGT    27

(2) INFORMATION FOR SEQ ID NO:54:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:54:

CCGACCTAGG TAGCTACGAA TCCTCCACTA G    31

(2) INFORMATION FOR SEQ ID NO:55:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:55:

TAGGATCCTG CCTGCCA    17

(2) INFORMATION FOR SEQ ID NO:56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:56:

CCTAGGACGG ACGGTAT    17

(2) INFORMATION FOR SEQ ID NO:57:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO ( x i ) SEQUENCE DESCRIPTION: SEQ ID NO:57:

TATGGCTTCA AGACCTCAGG TCCCCAAAGG CCTGAAGAAT CCACCAGGGC         50

( 2 ) INFORMATION FOR SEQ ID NO:58:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:58:

ACCGAAGTTC TGGAGTCCAG GGGTTTCCGG ACTTCTTAGG TGGTCCCGGT AC         52

( 2 ) INFORMATION FOR SEQ ID NO:59:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:59:

GCCAGCCCCA TGGCCCTGGT GGAT         24

( 2 ) INFORMATION FOR SEQ ID NO:60:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:60:

TTAGGAGGTC ATATGGCTCT GTTATTAGCA GTTTTTTGTC TGGTATTC         48

( 2 ) INFORMATION FOR SEQ ID NO:61:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:61:

TTAGGAGGTC ATATGTTGTT TCCAATTTCA ATGTCAGCAA CG         42

( 2 ) INFORMATION FOR SEQ ID NO:62:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:62:

TTAGGAGGTC ATATGGCTTC ACGTCCACAA GTACCAAAAG GC                    42

( 2 ) INFORMATION FOR SEQ ID NO:63:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:63:

TTAGGAGGTC ATATGGCTTT TCCAATTTCA ATGTCAGCAA CG                    42

( 2 ) INFORMATION FOR SEQ ID NO:64:

( i ) SEQUENCE CHARACTERISTICS:
      ( A ) LENGTH: 33 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:64:

Met  Leu  Phe  Pro  Ile  Ser  Met  Ser  Ala  Thr  Glu  Phe  Leu  Leu  Ala  Ser
1                   5                        10                       15

Val  Ile  Phe  Cys  Leu  Val  Phe  Trp  Val  Met  Arg  Ala  Ser  Arg  Pro  Gln
                    20                       25                       30

Val ( 2 ) INFORMATION FOR SEQ ID NO:65:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:65:

```
         Met Ala Ser Arg Pro Gln Val
         1               5
```

( 2 ) INFORMATION FOR SEQ ID NO:66:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:66:

```
         Met Ala Leu Leu Leu Ala Val Phe Cys Leu Val Phe Trp Val Met Arg
         1               5                   10                  15
         Ala Ser Arg Pro Gln Val
                     20
```

( 2 ) INFORMATION FOR SEQ ID NO:67:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:67:

```
         Met Leu Phe Pro Ile Ser Met Ser Ala Thr Glu Phe Leu Leu Ala Ser
         1               5                   10                  15
         Val Ile Phe Cys Leu Val Phe Trp Val Met Arg Ala Ser Arg Pro Gln
                         20                  25                  30
         Val
```

( 2 ) INFORMATION FOR SEQ ID NO:68:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:68:

```
         Met Ala Phe Pro Ile Ser Met Ser Ala Thr Glu Phe Leu Leu Ala Ser
         1               5                   10                  15
         Val Ile Phe Cys Leu Val Phe Trp Val Met Arg Ala Ser Arg Pro Gln
                         20                  25                  30
         Val
```